United States Patent
Laco et al.

(10) Patent No.: US 10,865,384 B2
(45) Date of Patent: Dec. 15, 2020

(54) 2,4,5-TRI-SUBSTITUTED AZOLE-BASED CASEIN KINASE 1 INHIBITORS AS INDUCERS FOR CARDIOMYOGENESIS

(71) Applicants: AGENCY FOR SCIENCE, TECHNOLOGY AND RESEARCH, Singapore (SG); NATIONAL UNIVERSITY OF SINGAPORE, Singapore (SG)

(72) Inventors: Filip Laco, Singapore (SG); Joo Leng Low, Singapore (SG); Steve Oh, Singapore (SG); Christina Li Lin Chai, Singapore (SG); Qixing Zhong, Singapore (SG)

(73) Assignees: Agency for Science, Technology and Research, Singapore (SG); National University of Singapore, Singapore (SG)

( * ) Notice: Subject to any disclaimer, the term of this patent is extended or adjusted under 35 U.S.C. 154(b) by 11 days.

(21) Appl. No.: 15/117,127

(22) PCT Filed: Feb. 6, 2015

(86) PCT No.: PCT/SG2015/050015
§ 371 (c)(1),
(2) Date: Aug. 5, 2016

(87) PCT Pub. No.: WO2015/119579
PCT Pub. Date: Aug. 13, 2015

(65) Prior Publication Data
US 2017/0166867 A1 Jun. 15, 2017

(30) Foreign Application Priority Data
Feb. 7, 2014 (SG) ................. 2014009815

(51) Int. Cl.
| | |
|---|---|
| *C12N 5/077* | (2010.01) |
| *C07D 401/04* | (2006.01) |
| *C07D 405/04* | (2006.01) |
| *A61K 31/4439* | (2006.01) |
| *A61K 31/506* | (2006.01) |

(Continued)

(52) U.S. Cl.
CPC ........ *C12N 5/0657* (2013.01); *A61K 31/4178* (2013.01); *A61K 31/4439* (2013.01); *A61K 31/506* (2013.01); *C07D 401/04* (2013.01); *C07D 405/04* (2013.01); *C07D 405/14* (2013.01); *C07D 413/04* (2013.01); *C12N 2501/727* (2013.01); *C12N 2501/999* (2013.01); *C12N 2506/02* (2013.01); *C12N 2506/45* (2013.01)

(58) Field of Classification Search
CPC .. C07D 401/04; C07D 405/04; C07D 413/04; C07D 405/14
See application file for complete search history.

(56) References Cited

U.S. PATENT DOCUMENTS

| | | |
|---|---|---|
| 5,777,097 A | 7/1998 | Lee et al. |
| 6,288,062 B1 | 9/2001 | Adams et al. |

(Continued)

FOREIGN PATENT DOCUMENTS

| | | |
|---|---|---|
| CA | 2777632 A1 | 5/2011 |
| CN | 102686580 A | 9/2012 |

(Continued)

OTHER PUBLICATIONS

STN; Registry No. 208641-66-1, Jul. 19, 1998 (Year: 1998).*

(Continued)

*Primary Examiner* — Umamaheswari Ramachandran
(74) *Attorney, Agent, or Firm* — Womble Bond Dickinson (US) LLP

(57) ABSTRACT

This invention relates to a method for inducing or enhancing the differentiation of pluripotent stem cells into cardiomyocyte via casein kinase 1 inhibition said method comprising culturing the stem cells in the presence of a medium comprising a casein kinase 1 inhibitor of the formula (I) or (II) or a stereoisomer, tautomer, or a salt thereof wherein $R^1$, $R^2$ and $R^3$ independently from another represent hydrogen, optionally substituted alkyl, alkenyl, alkynyl, heterocyclyl, heteroaryl or aryl; X represents $NR^4$, O or S; and $R^4$ represents hydrogen, optionally substituted alkyl, alkenyl, alkynyl, heterocyclyl, heteroaryl or aryl. The method can be used in the late phase of stem cell differentiation and in the compounds of formula (I) or (II) in combination with other small molecules can lead to especially high differentiation of stem cells into cardiomyocytes. The invention further relates to novel compounds which can be used in the method of the invention and kits for stem cell differentiation.

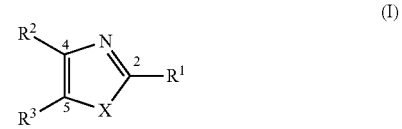

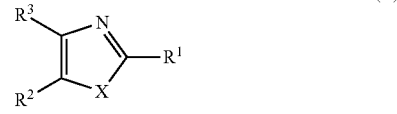

3 Claims, 22 Drawing Sheets

(51) Int. Cl.
*C07D 413/04* (2006.01)
*A61K 31/4178* (2006.01)
*C07D 405/14* (2006.01)

(56) References Cited

U.S. PATENT DOCUMENTS

| | | | |
|---|---|---|---|
| 8,318,489 | B2 | 11/2012 | Davidson et al. |
| 8,518,944 | B2 | 8/2013 | Subramanyam et al. |
| 2005/0203155 | A1 | 9/2005 | Salassidis et al. |
| 2007/0204351 | A1 | 8/2007 | Davidson et al. |
| 2008/0187494 | A1 | 8/2008 | Davidson et al. |
| 2009/0202498 | A1 | 8/2009 | Davidson et al. |
| 2011/0098272 | A1 | 4/2011 | Subramanyam et al. |
| 2013/0189785 | A1 | 7/2013 | Palecek et al. |
| 2013/0244262 | A1 | 9/2013 | Yamashita et al. |

FOREIGN PATENT DOCUMENTS

| | | |
|---|---|---|
| DE | 69433501 T2 | 11/2004 |
| EP | 1306377 A2 | 5/2003 |
| EP | 0727998 B1 | 1/2004 |
| EP | 2493876 B1 | 9/2012 |
| WO | WO 96/13626 A1 | 6/1996 |
| WO | WO 98/22108 A1 | 5/1998 |
| WO | WO 03/024447 A1 | 3/2003 |
| WO | WO2003024447 A1 | 3/2003 |
| WO | WO 2004/005264 A2 | 1/2004 |
| WO | WO2004005264 A2 | 1/2004 |
| WO | WO2007030870 | 3/2007 |
| WO | WO2007070964 | 6/2007 |
| WO | WO2011051858 A1 | 5/2011 |
| WO | WO 2012/067256 A1 | 5/2012 |
| WO | WO 2012/084678 A1 | 6/2012 |
| WO | WO 2013/055297 A1 | 4/2013 |
| WO | WO 2013/056072 A1 | 4/2013 |

OTHER PUBLICATIONS

Patani et al. (Chem Rev 1996, 96, 3147-3196). (Year: 1996).*
Silverman (The Organic Chemistry of Drug Design and Drug Action, 1992, p. 15-22). (Year: 1992).*
PCT Notification of Transmittal of the International Search Report and the Written Opinion of the International Searching Authority, or the Declaration for PCT Counterpart Application No. PCT/SG2015/050015, 13 pp., (dated Jun. 15, 2015).
PCT Notification Concerning Transmittal of International Preliminary Report on Patentability (Chapter I of the Patent Cooperation Treaty) for PCT Counterpart Application No. PCT/SG2015/050015, 9 pp., (Aug. 18, 2016).
Aouadi, Myriam, et al., "p38 Mitogen-Activated Protein Kinase Activity Commits Embryonic Stem Cells to Either Neurogenesis or Cardiomyogenesis", Stem Cells, vol. 24, pp. 1399-1406, (2005).
Baan, Bart, et al., "The Role of c-Jun N-Terminal Kinase, p38, and Extracellular Signal-Regulated Kinase in Insulin-Induced Thr69 and Thr71 Phosphorylation of Activating Transcription Factor 2", Molecular Endocrinology, vol. 20, No. 8, pp. 1786-1795, (Aug. 2006).
Barruet, Emilie, et al., "p38 Mitogen-Activated Protein Kinase Controls Two Successive Steps During the Early Mesodermal Commitment of Embryonic Stem Cells", Stem Cells and Development, vol. 20, No. 7, pp. 1233-1246, (2011).
Bibian, Mathieu, et al., "Development of Highly Selective Casein Kinase 1δ/ε (CK1δ/1ε) Inhibitors with Potent Antiproliferative Properties", Bioorganic & Medicinal Chemistry Letters, vol. 23, pp. 4374-4390, (2013).
Bilodeau, Mark T., et al., "Solid-Supported Synthesis of Imidazoles: A Strategy for Direct Resin-Attachment to the imidazole Core", J. Org. Chem., vol. 63, pp. 2800-2801, (1996).
Caspi, Oren, et al,. "Regenerating the Heart Using Human Embryonic Stem Cells—from Cell to Bedside", IMAJ, vol. 8, pp. 208-214, (Mar. 2005).

Chen, Baozhi, et al., "Small Molecule-Mediated Disruption of Wnt-Dependent Signalling in Tissue Regeneration and Cancer", Nat. Chem. Biol., vol. 5, No. 2, pp. 100-107, (Feb. 2009).
Cheong, Jit Kong, et al., "IC261 Induces Cell Cycte Arrest and Apoptosis of Human Cancer Cells via CK1δ/ε and Wnt/β-Caterin Independent Inhibition of Mitotic Spindle Formation", Oncogena, vol. 30, pp. 2558-2569, (2011).
Cheong, Jit Kong, et al., "Casein Kinase 1: Complexity in the Family", The International Journal of Biochemistry & Cell Biology, vol. 43, pp. 465-469, (2011).
Covey, Tracy M., et al., "PORCN Moonlights in a Wnt-independent Pathway That Regulates Cancer Cell Proliferation", PloS ONE, vol. 7, No. 4, e34532, pp. 1-11, (Apr. 2012).
Cuenda, Ana, et al., "SB 203580 is a Specific Inhibitor of a MAP Kinase Homologue which is Stimulated by Cellular Stresses and Interleukin-1", FEBS Letters, vol. 364, No. 2, pp. 229-233, (1995).
Davis, Mindy I, et al., "Comprehensive Analysis of Kinase Inhibitor Selectivity", Nature Biotechnology, vol. 29, No. 11, pp. 1046-1051, (Nov. 2011).
Del Valle-Perez, Beatriz, et al., "Coordinated Action of CK1 Isoforms in Canonical Wnt Signaling", Molecular and Cellular Biology, vol. 31, No. 14, pp. 2877-2888, (Jul. 2011).
Elliott, David A, et al. ,NKX2-5 (eGFP/w) hESCs for isolation of human cardiac progenitors and cardiomyocytes,Nature Methods, vol. 8,pp. 1037-1040, Dec. 2011.
Foldynova-Trantirkova, Silvie, et al., "Breast Cancer-Specific Mutations in CK1ε Inhibit Wnt/β-Catenin and Activate the Wnt/Rac1/JNK and NFAT Pathways to Decrease Cell Adhesion and Promote Cell Migration", Breast Cancer Research, vol. 12, R30, pp. 1-14, (2010).
Gadue, Paul, et al., "Mnt and TGF-β Signaling are Required for the Induction of an In Vitro Model of Primitive Streak Formation using Embryonic Stem Cells", PNAS, vol. 103, No. 45, pp. 16806-16811, (Nov. 7, 2006).
Gaur, Meenakshi, et al., "Timed Inhibition of p36MAPK Directs Accelerated Differentiation of Human Embryonic Stem Cells into Cardiomyocytes", Cytotherapy, vol. 12, No. 6, pp. 807-817, (Oct. 2010).
Gessert, Susanne, et al., "The Multiple Phases and Faces of Wnt Signaling During Cardiac Differentiation and Development", Circulation Research, vol. 107, pp. 186-199, (2010).
Gonzalez, Rodolfo, et al., "Stepwise Chemically Induced Cardiomyocyte Specification of Human Embryonic Stem Cells", Angewandte Chemie International Edition, vol. 50, No. 47, pp. 11181-11185, (Nov. 18, 2011).
Graichen, Ralph, et al., "Enhanced Cardiomyogenesis of Human Embryonic Stem Cells by a Small Molecular Inhibitor of p38 MAPK", Differentiation, vol. 76, No. 4, pp. 357-370, (Apr. 2008).
Greer, Yoshimi Endo, et al., "Casein Kinase 1 Delta Functions at the Centrosome to Mediate Wnt-3a—Dependent Neurite Outgrowth", J. Cell Biol., vol. 192, No. 6, pp. 993-1004, (2011).
Han, Jiahuai, et al., "Regulation of MEF2 by p38 MAPK and Its Implication in Cardiomyocyte Biology", Trends in Cardiovascular Medicine, vol. 10, No. 1, pp. 19-22, (Jan. 2000).
Hazzalin, Catherine A., et al., "p38/RK is Essential for Stress-Induced Nuclear Responses: JNK/SAPKs and c-Jun/ATF-2 Phosphorylation are Insufficient", Current Biology, vol. 6, No. 8, pp. 1028-1031, (1996).
Hudson, James, et al., "Primitive Cardiac Cells from Human Embryonic Stem Cells", Stem Cells and Development, vol. 21, No. 9, pp. 1513-1523, (Jun. 2012).
Jung, Yong-Sam, et al., "KR-31378 Protects Cardiac H9c2 Cells from Chemical Hypoxia-Induced Cell Death via Inhibition of JNK/p38 MAPK Activation", Japanese Journal of Physiology, vol. 54, pp. 575-583, (2004).
Karaman, Mazen W., et al., "A Quantitative Analysis of Kinase Inhibitor Selectivity", Nature Biotechnology, vol. 26, No. 1, pp. 127-132, (Jan. 2008).
Karthikeyan, C., et al., "Quantitative Structure Activity Relationships of Some Selective Inhibitors of Glucagon Receptor: A Hansch Approach", Asian Journal of Biochemistry, vol. 1, No. 4, pp. 307-315, (2006).

(56) References Cited

OTHER PUBLICATIONS

Kempf, Henning, et al., "Distinct Regluation of Mitogen-Activated Protein Kinase Activities is Coupled with Enhanced Cardiac Differentiation of Human Embryonic Stem Cells", Stem Cell Research, vol. 7, pp. 198-209, (2011).
Knippschild, Uwe, et al., "The Casein Kinase 1 Family: Participation in Multiple Cellular Processes in Eukarycies", Cellular Signalling, vol. 17, pp. 675-689, (2005).
Koyanagi, Masamichi, et al., "Non-canonical Wnt Signaling Enhances Differentiation of Human Circulating Progenitor Cells to Cardiomyogenic Cells", The Journal of Biological Chemistry, vol. 280, No. 17, pp. 16838-16842, (Apr. 29, 2005).
Laco, Filip, et al., "Cardiomyocyte Differentiation of Pluripotent Stem Cells with SB203580 Analogues Correlates with Wnt Pathway CK1 Inhibition Independent of p38 MAPK Signaling", Journal of Molecular and Celllular Cardiology, vol. 80, pp. 56-70, (2015).
Lam, Albert O., et al., "Rapid and Efficient Differentiation of Human Pluripotent Stem Cells into Intermediate Mesoderm That Forms Tubles Expressing Kidney Proximal Tubular Markers", J. Am. Soc. Nephrol., vol. 25, pp. 1-15, (2014).
Lanier, Marion, et al., "Wnt Inhibition Correlates with Human Embryonic Stem Cell Cardiomyogenesis: A Structure Activity Relationship Study Based on Inhibitors for the Wnt Response", J. Med. Chem., vol. 55, No. 2, pp. 697-708, (Jan. 26, 2012).
Lee, Jae Wook, et al., "A Small Molecular Modulates Circadian Rhythms through Phosphorylation of the Period Protein", Angew. Chem. Int. Ed., vol. 50, pp. 10608-10611, (2011)
Lee, Se-Yeon, et al., "The Promotion of Cardiogenic Differentiation of hMSCs by Targeting Epidermal Growth Factor Receptor using microRNA-133a", Biomaterials, vol. 34, No. 1, pp. 92-99, (Jan. 2013).
Leroux, Frédéric, et al., "The Abnormal Behavior of an Atropisomar: 3.3'-Dibromo-1,1'-difluoro-2,2'-binaphthyl Reacting with Alkyllithium Compounds", European Journal of Organic Chemistry, vol. 2005, No. 23, pp. 5049-5054, (Dec. 2005).
Low, Joo-Leng, et al., "Tri-Substituted Imidazole Analoguss of SB203580 as Inducers for Cardiomyogenesis of Human Embryonic Stem Cells", Bioorganic & Medicinal Chemistry Letters, vol. 23, No. 11, pp. 3300-3303, (2013).
Minami, Itsunari, et al., "A Small Molecule that Promotes Cardiac Differentiation of Human Pluripotent Stem Cells under Defined, Cytokine- and Xeno-Irse Conditions", Cell Reports, vol. 2, pp. 1448-1450, (Nov. 29, 2012).
Monzen, Koshiro, et al., "Smads, TAK1, and Their Common Target ATF-2 Play a Critical Role in Cardiomyocte Differentiation", The Journal of Cell Biology, vol. 153, No. 4, pp. 687-698, (May 14, 2001).
Mummery, Christine L., et al., "Differentiation of Human Embryonic Stem Cells and Induced Pluripotent Stem Cells to Cardiomyocytes: A Methods Overviw", Circulation Research, vol. 111, pp. 344-358. (2012).
Naito, Atsuhiko T., et al., "Developmental Stage-Specific Biphasic Roles of Wnt/β-catenin Signaling in Cardiomyogenesis and Hematopoiesis", PNAS, vol. 103, No. 52, pp. 19812-19817, (Dec. 26, 2006).
Niehrs, Christof, et al., "Regulation of Lrp6 Phosphorylation", Cellular and Molecular Life Sciences, vol. 67, No. 15, pp. 2551-2562, (Aug. 2010).
Oeztuerk-Winder, Feride, et al., "The Many Faces of p38 Mitogen-Activated Protein Kinase in Progenitor/Stem Cell Differentiation", Biochem. J., vol. 445, pp. 1-10, (2012).
Rena, Graham, et al., "D4476, A Cell-Permeant Inhibitor of CK1, Suppresses the Site-Specific Phosphorylation and Nuclear Exclusion of FOXO1a", EMBO Reports, vol. 5, No. 1, pp. 60-65, (2004).
Schmittgen, Thomas D., et al., "Analyzing Real-Time PCR Data by the Comparative C; Method", Nature Protocols, vol. 3, No. 6, pp. 1101-1108, (2008).

Shanware, Naval P., et al., "Non-specific In Vivo Inhibition of CK1 by the Pyridinyl Imidazole p38 Inhibitiors SB 203580 and SB 202190", BMB Reports, vol. 42, No. 3, pp. 142-147, (2009).
Sudo, Tatsuhiko, et al., "p38 Mitogen-Activated Protein Kinase Plays a Key Role in Regulating MAPKAPK2 Expression", Biochemical and Biophysical Research Communications, vol. 337, No. 2, pp. 415-421, (Nov. 18, 2005).
Thomson, James A., et al., "Embryonic Stem Cell Lines Derived from Human Blastocysts", Science, vol. 282, No. 5391, pp. 1145-1147, (Nov. 6, 1998).
Ting, Sherwin, et al., "Nutrient Supplemented Serum-Free Medium Increases Cardiomyogenesis Efficiency of Human Pluripotent Stem Cells", World Journal of Stem Cells, vol. 5, No. 3, pp. 86-97, (Jul. 26, 2013).
Ting, Sherwin, et al., "Time-Resolved Video Analysis and Management System for Monitoring Cardiomyocyte Differentiation Processes and Toxicology Assays", Biotechnology Journal, vol. 8, No. 5, pp. 675-683, (May 2014).
Tran, Thanh H., et al., "Wnt3a-Induced Mesoderm Formation and Cardiomyogenesis in Human Embryonic Stem Cells", Stem Cells, vol. 27, No. 8, pp. 1869-1876, (Aug. 2009).
Ueno, Shuichi, et al., "Biphasic Role for Wnt/β-Catenin Signaling in Cardiac Specification in Zebrafish and Embryonic Stem Cells", PNAS, vol. 104, No. 23, pp. 9685-9690, (Jun. 5, 2007).
Verkaar, Folkert, et al., "Inhibition of Wnt/β-Catenin Signaling by p38 MAP Kinase Inhibitors Is Explained by Cross-Reactivity with Casein Kinase 1σ/ε", Chemistry & Biology, vol. 18, pp. 485-494, (Apr. 22, 2011).
Walton, Kevin M., et al., "Selective Inhibition of Casein Kinase 1g Minimally Alters Circadian Clock Period", The Journal of Pharmacology and Experimental Therapeutics, vol. 330, No. 2, pp. 430-439, (2009).
Wang, Hanmin, et al., "Cardiac Induction of Embryonic Stem Cells by a Small Molecule Inhibitor of Wnt/β-Catenin Signaling", ACS Chem. Biol., vol. 6, No. 2, pp. 192-197, (Feb. 18, 2011).
Wang, Jingcai, et al., "Distinct Signaling Properties of Mitogen-activated Protein Kinase Kinases 4 (MKK4) and 7 (MKK7) in Embryonic Stem Cell (ESC) Differentiation", The Journal of Biological Chemistry, vol. 287, No. 4, pp. 2787-2797, (Jan. 20, 2012).
Willems, Erik, et al., "Small Molecule Inhibitors of the Wnt Pathway Potently Promote Cardiomyocytes from Human Embryonic Stem Cell Derived Mesoderm", Circulation Research, vol. 109, No. 4, pp. 360-364, (2011).
Zarghi, Afshin, et al., "Design and Synthesis of New 1,3-benzthiazinan-4-one Derivatives as Selective Cyclooxygenase (COX-2) Inhibitors", Bioorganic & Medicinal Chemistry, vol. 17, pp. 5369-5373, (2009).
Zhang, Lei, et al., "Regulation of Wingless Signaling by the CK1 Family in *Drosophilia* Limb Development", Developmental Biology, vol. 299, pp. 221-237, (2005).
Zhu, Wei-Zhong, et al., "Neuregulin/ErbB Signaling Regulates Cardiac Subtype Specification in Differentiating Human Embryonic Stem Stells", Circuation Research, vol. 107, pp. 776-786, (2010).
Barrett, et al., "Oxazole Synthesis with Minimal Purification: Synthesis and Application of a ROMPgel Tosmic Reagent", Organic Letters, Dec. 22, 2000, vol. 3, pp. 271-273.
Briggs, et al., "Synthesis of Biologically Active Amines via Rhodium-Bisphosphite-Catalyzed Hydroaminomethylation", Organic Letters, Sep. 27, 2005, vol. 7, pp. 4795-4798.
Meanwell, "Improving Drug Candidates by design: A Focus on Physicochemical Properties As a Means of Improving Compound Disposition and Safety", Chemical Research in Toxicology, Jul. 26, 2011, vol. 24, pp. 1420-1456.
Peifer, et al., "3,4-Diaryl-isoxazoles and -imidazoles as Potent Dual Inhibitors of p38α Mitogen Activated Protein Kinase and Casein Kinase 1σ", Journal of Medicinal Chemistry, vol. 52, Dec. 10, 2009, pp. 7618-7630.

\* cited by examiner

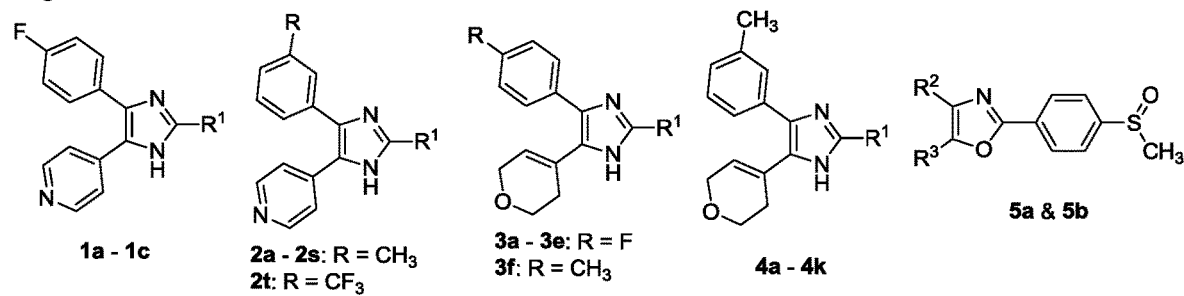

[Fig. 2]
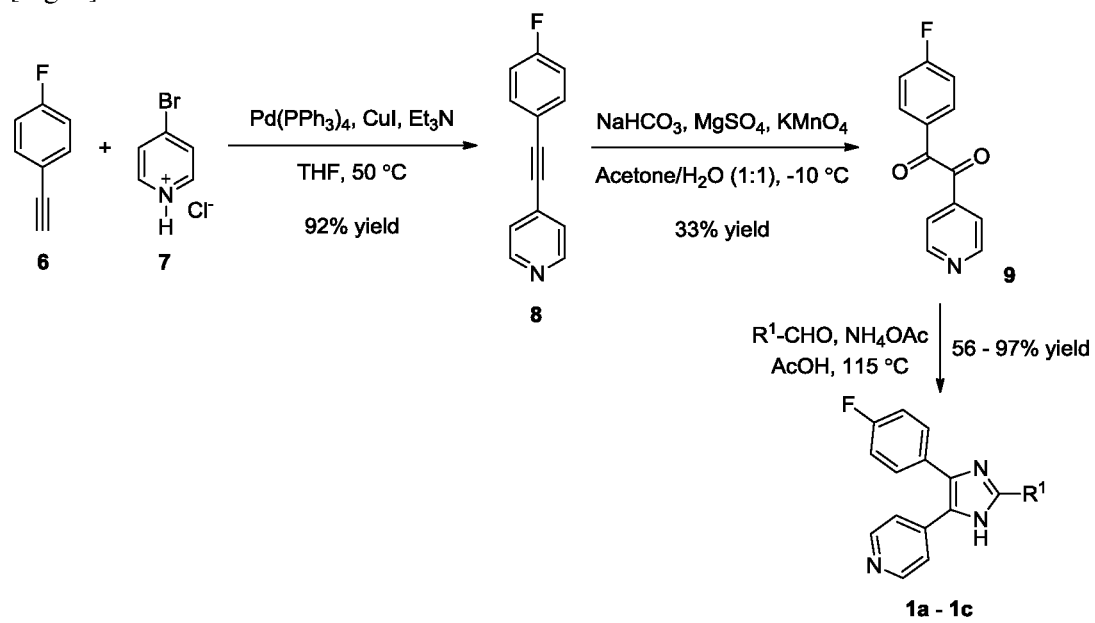

[Fig. 3]
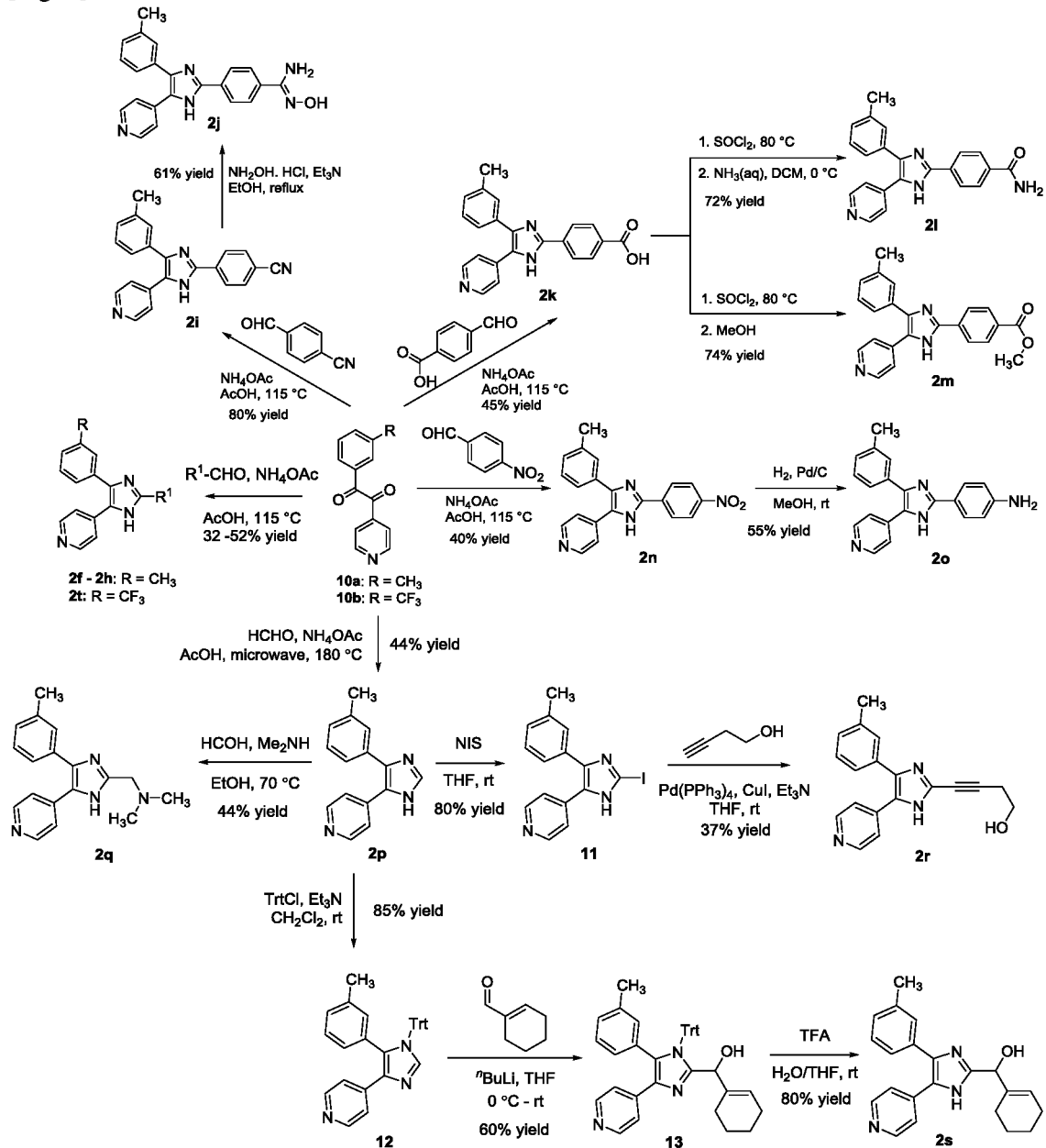

[Fig. 4]
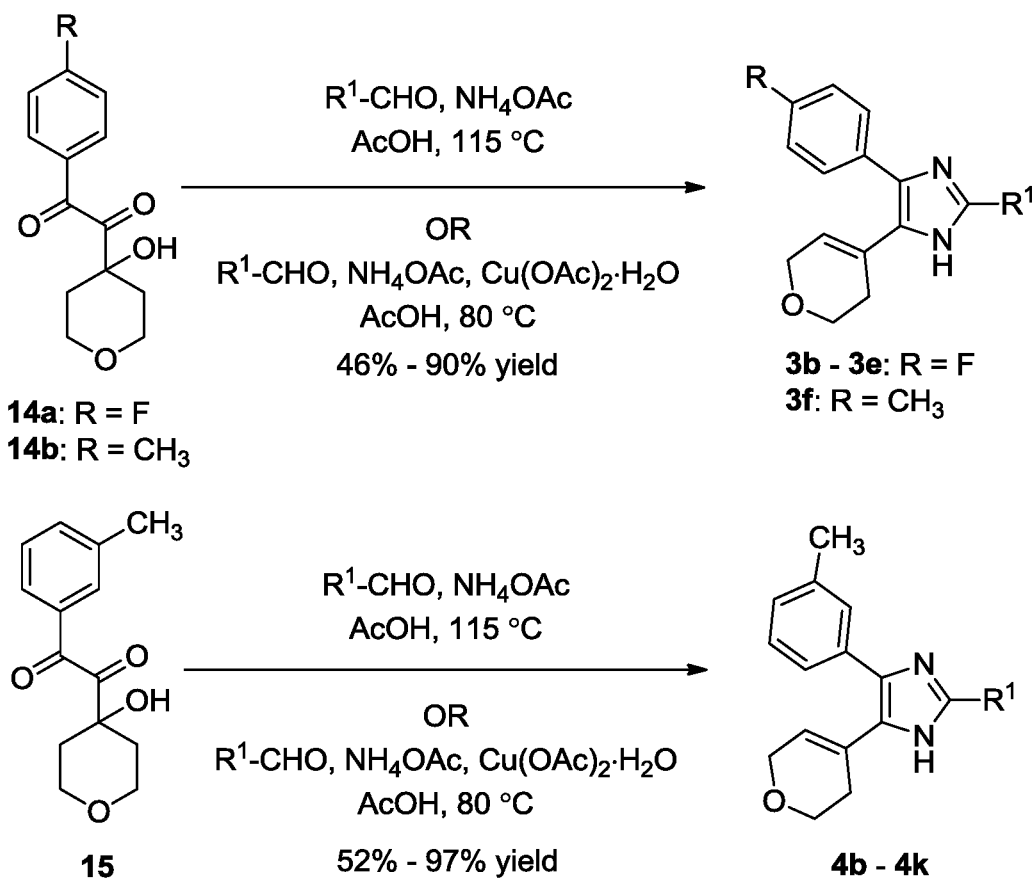

[Fig. 5]
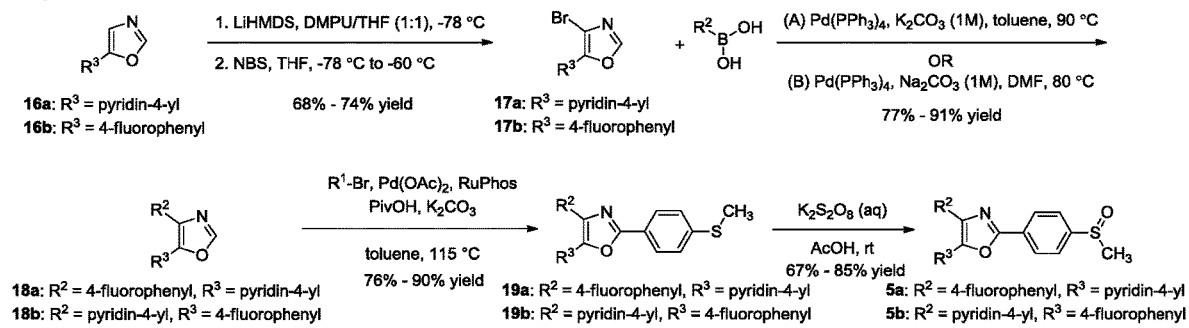

[Fig. 6a]
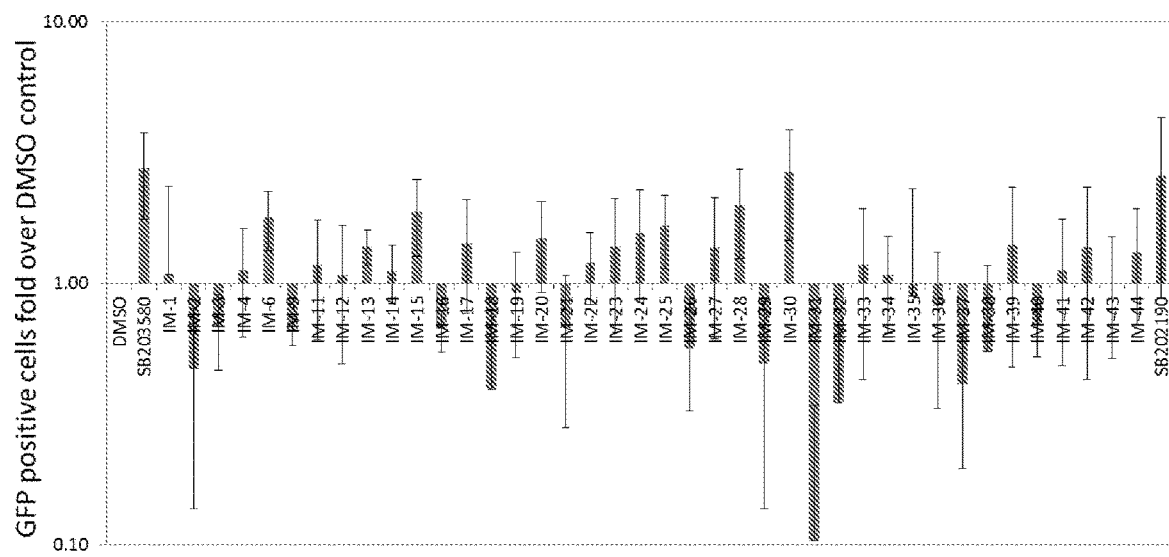

[Fig. 6b]
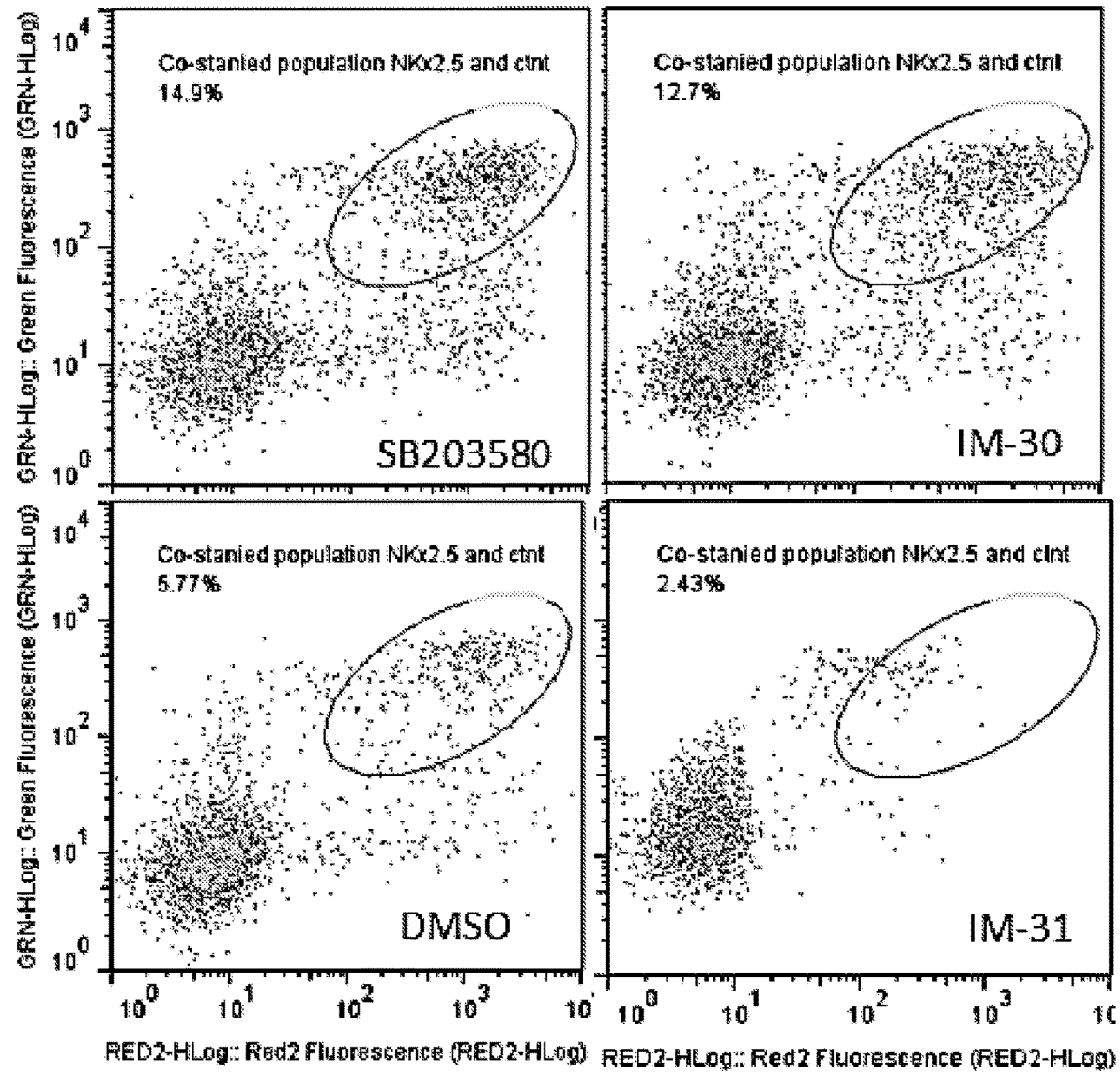

[Fig. 6c]
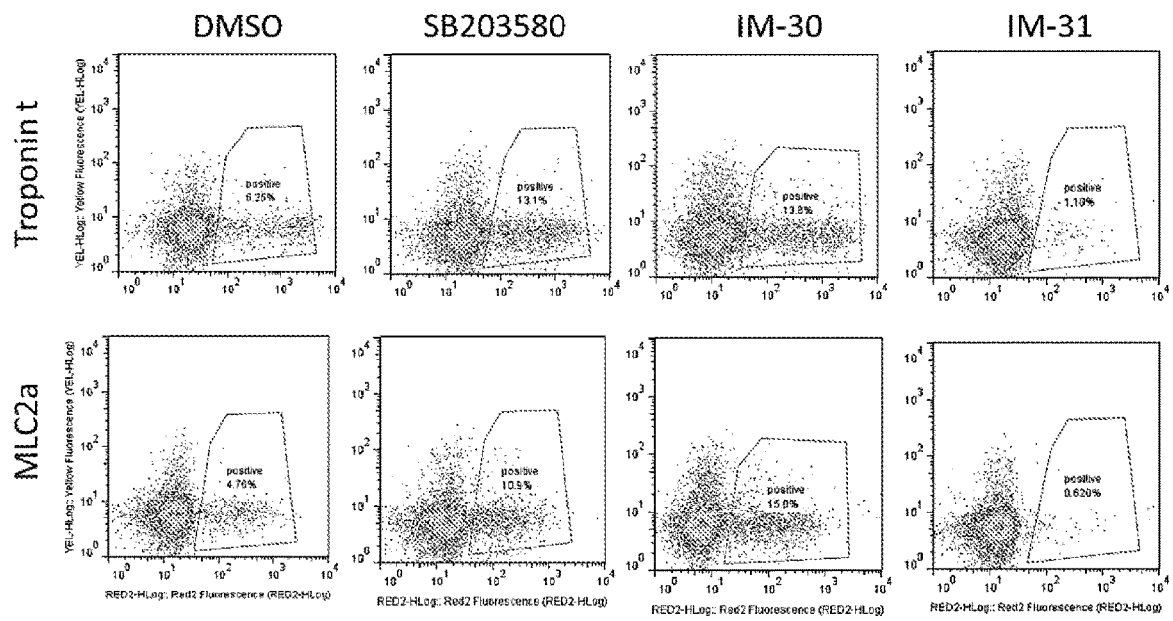

[Fig. 6d]
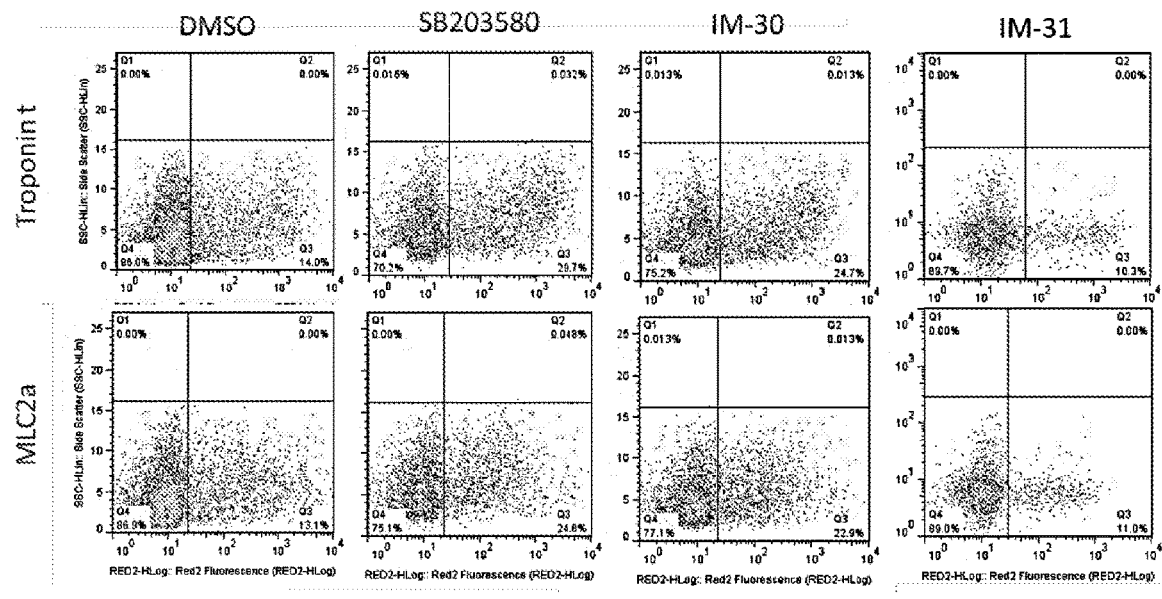

[Fig. 6e]
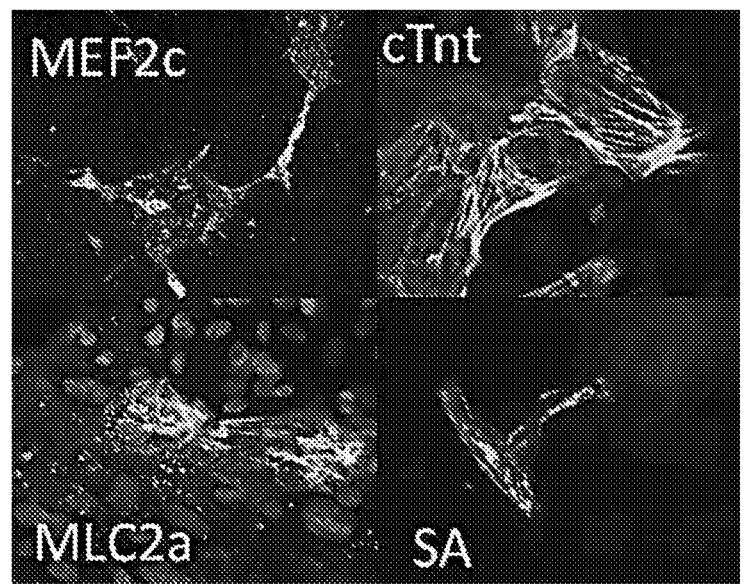

[Fig. 6f]
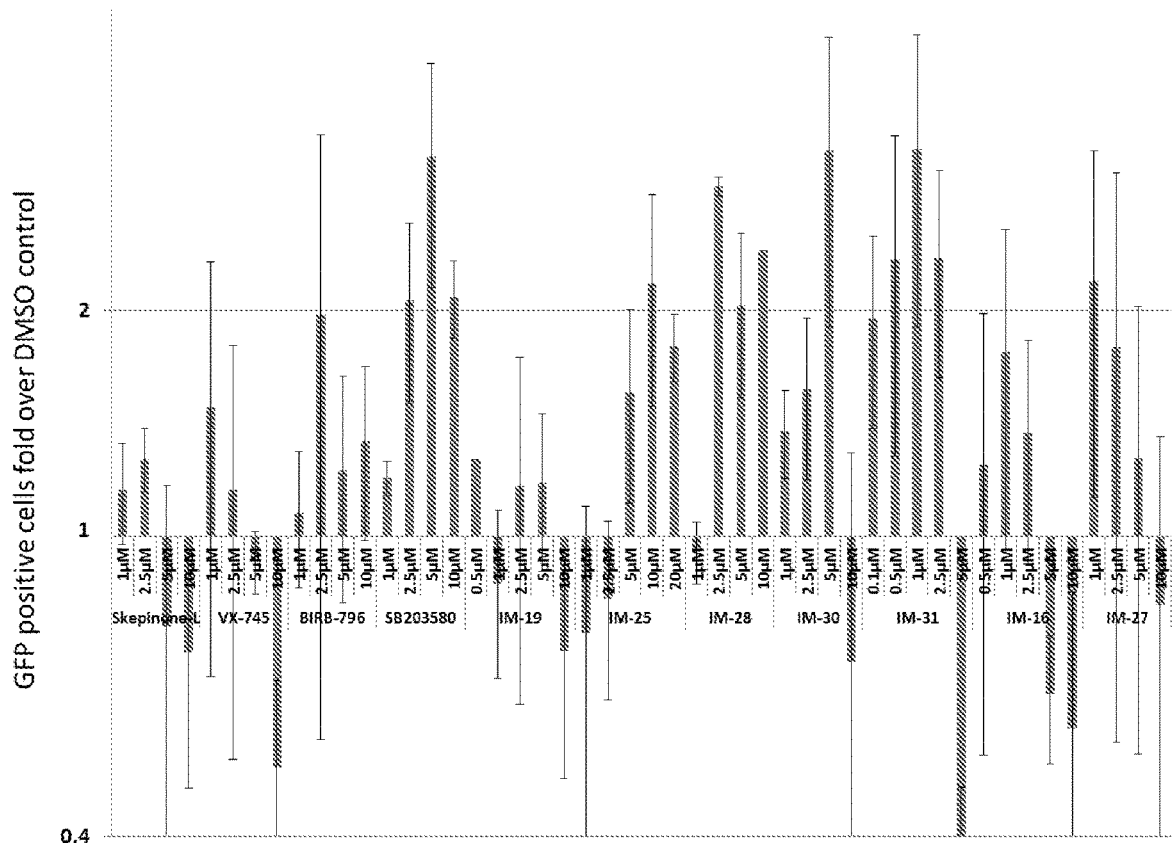

[Fig. 6g]
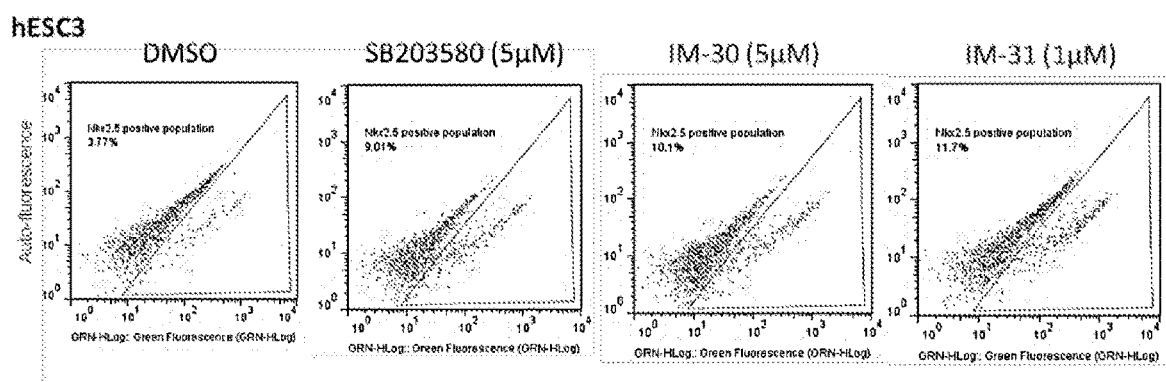

[Fig. 6h]
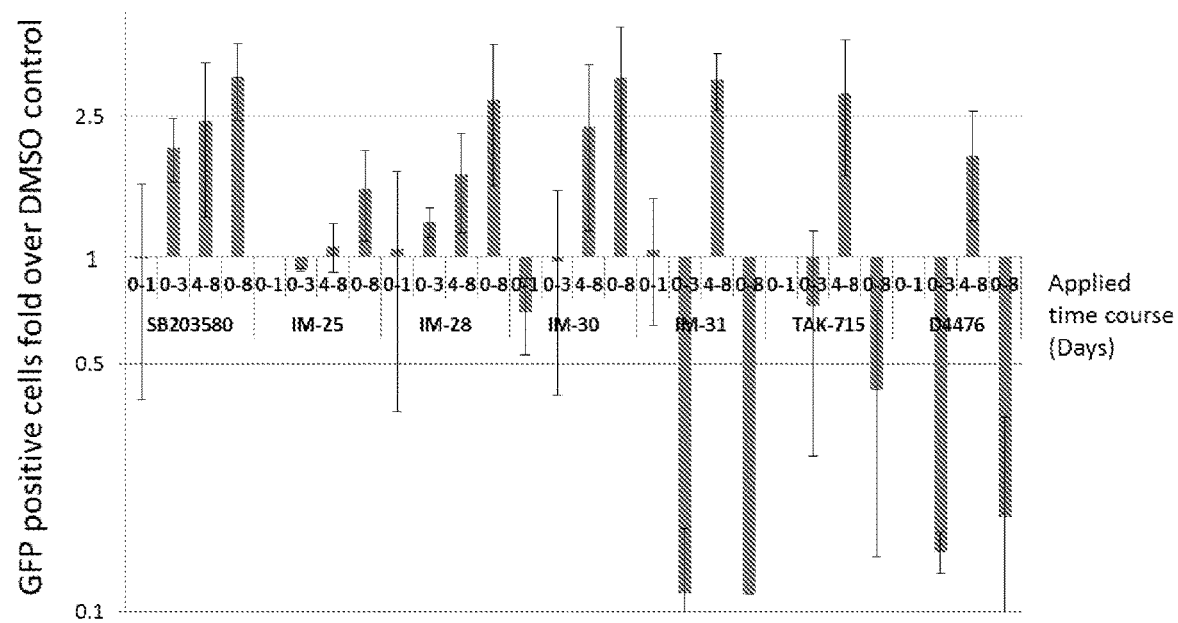

[Fig. 7a]
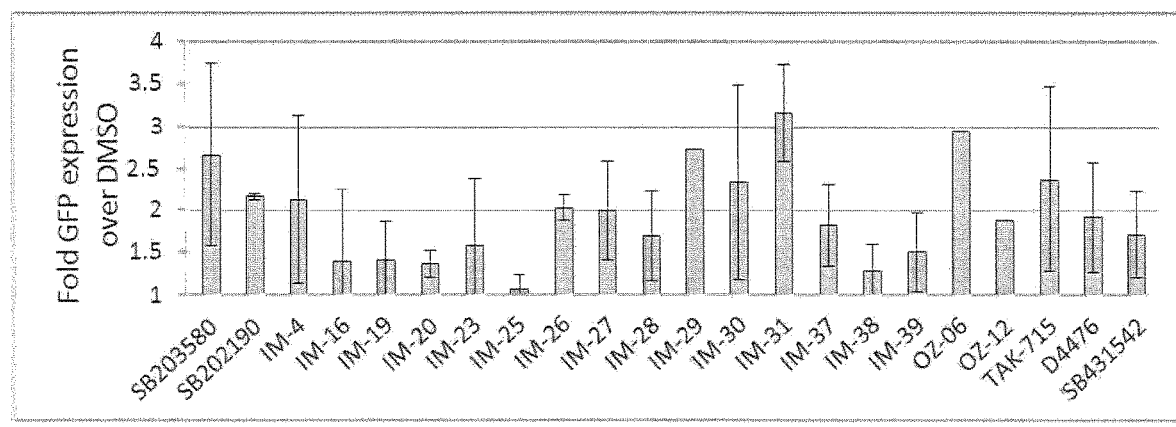

[Fig. 7b]
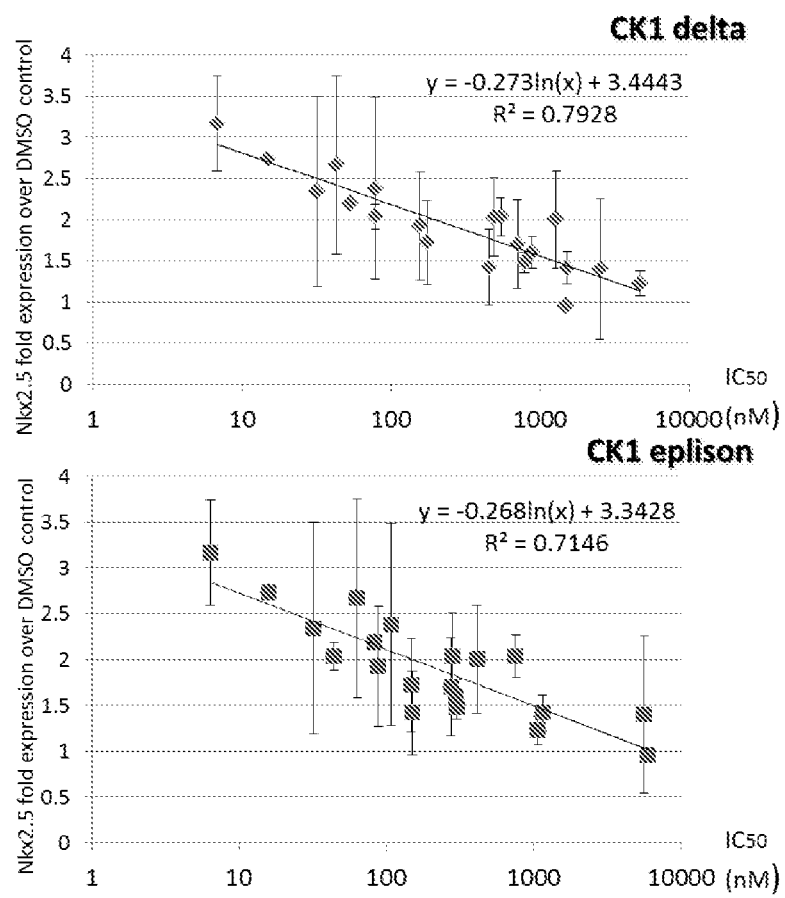

[Fig. 8a]
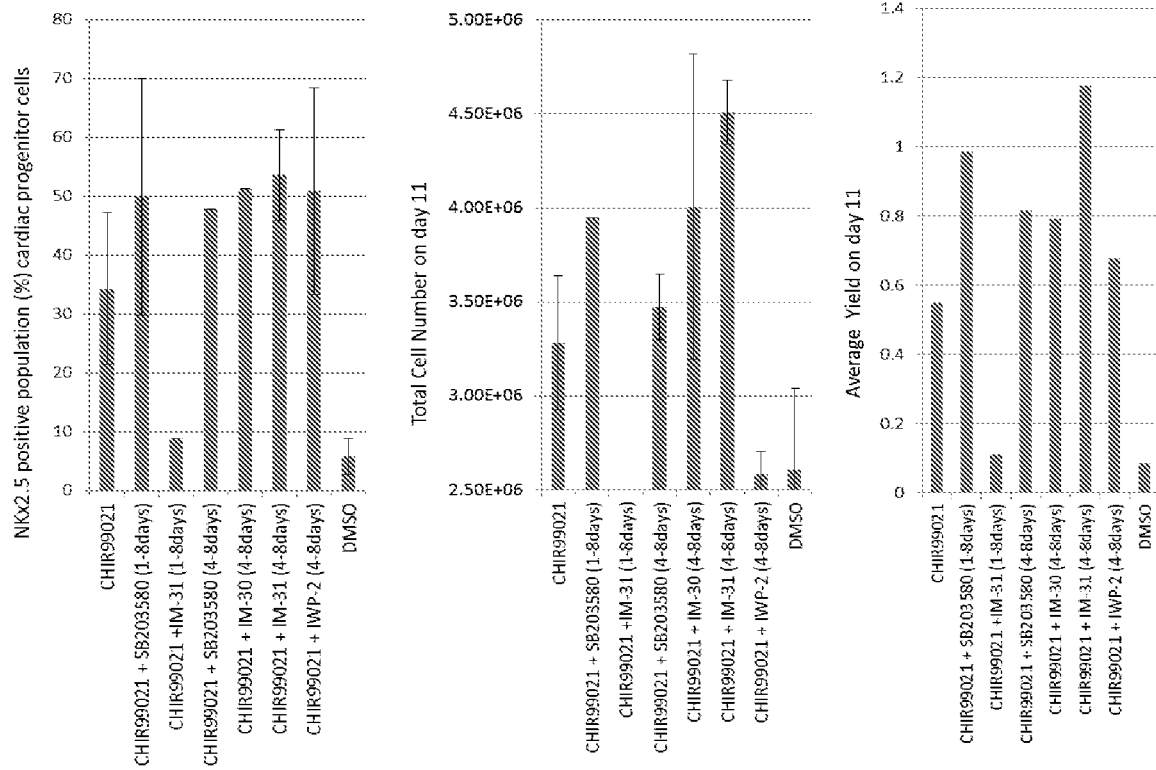

[Fig. 8b]
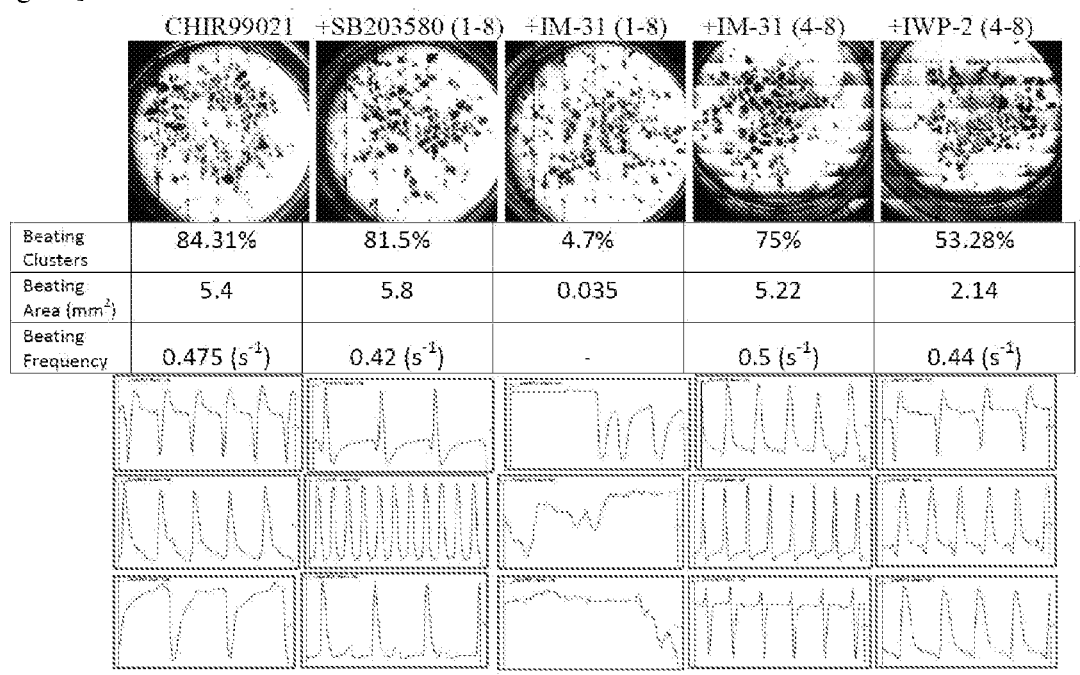

[Fig. 9]
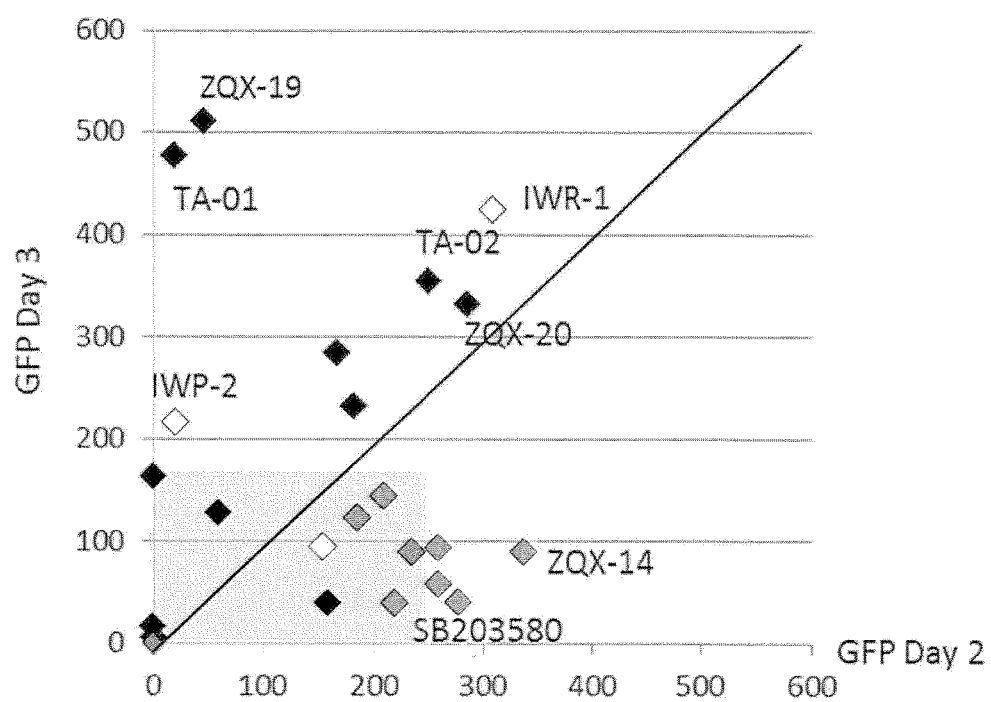

[Fig. 10]
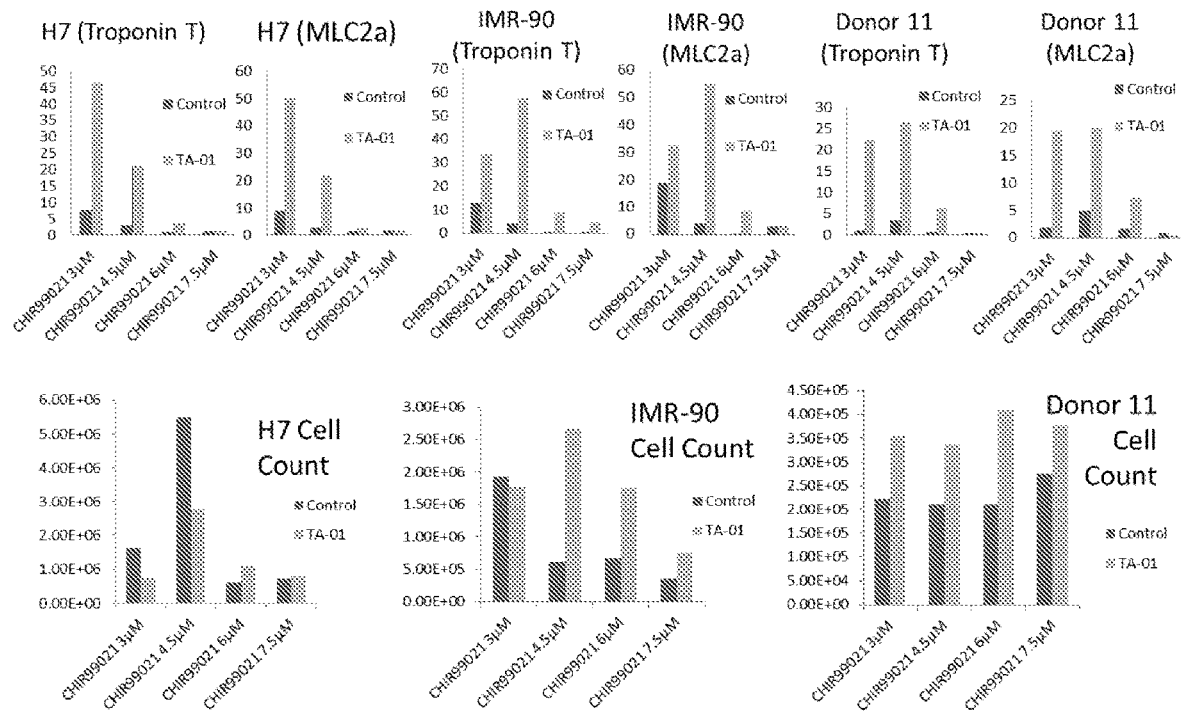

[Fig. 11a]
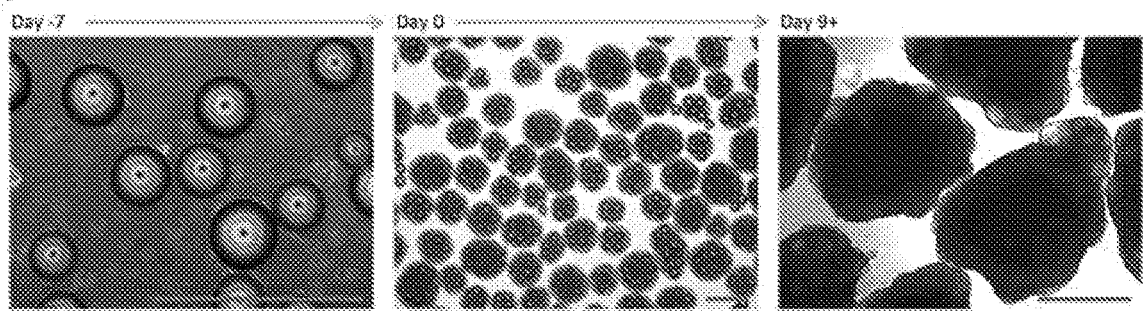

[Fig. 11b]
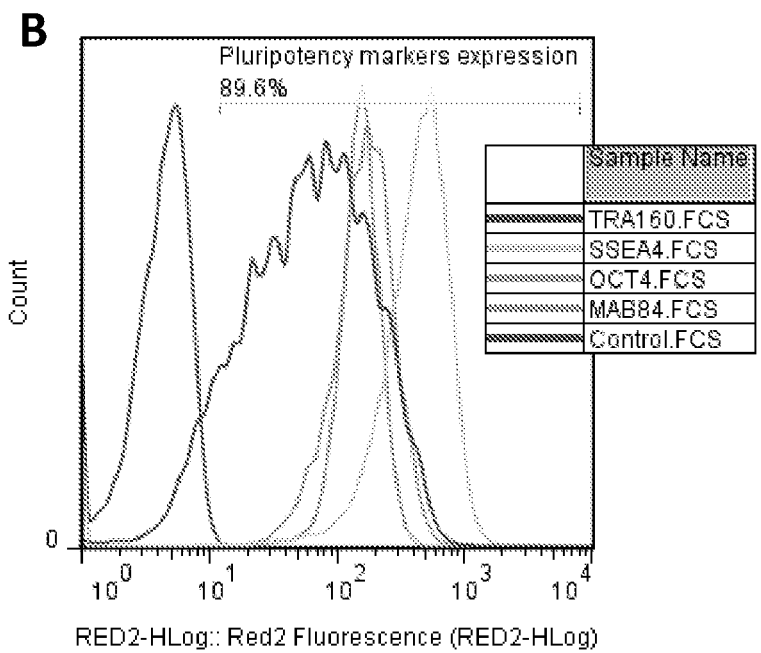

[Fig. 11c]
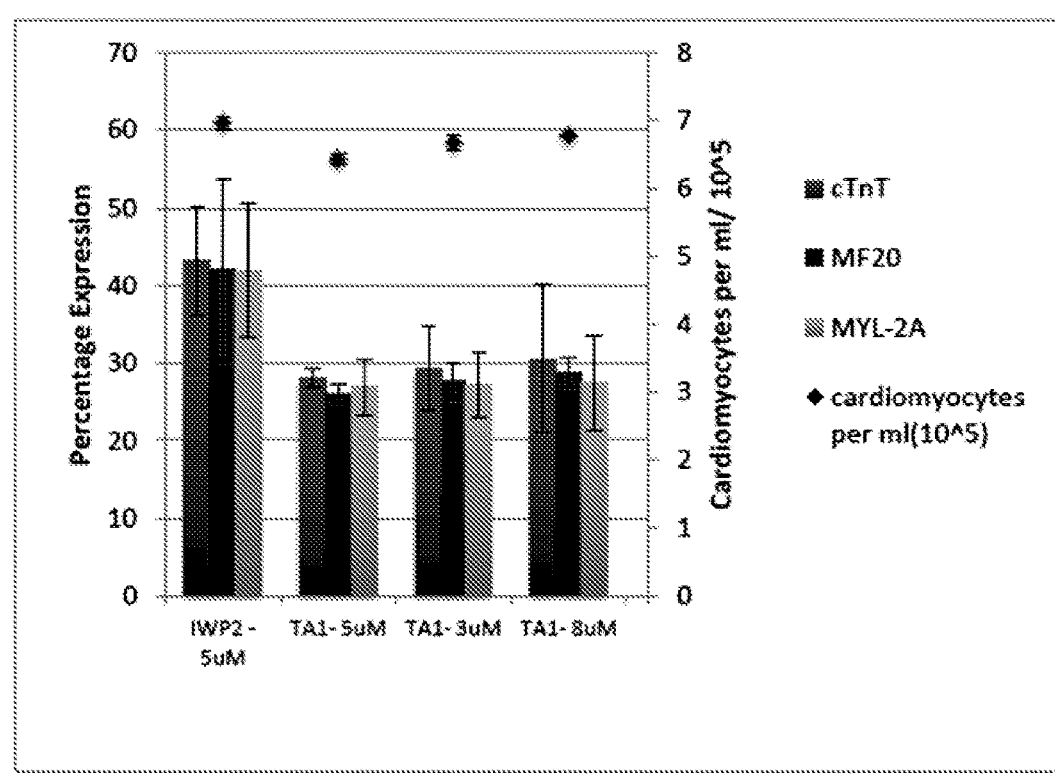

2,4,5-TRI-SUBSTITUTED AZOLE-BASED CASEIN KINASE 1 INHIBITORS AS INDUCERS FOR CARDIOMYOGENESIS

CROSS-REFERENCE TO RELATED APPLICATIONS

This patent application is a U.S. National Phase Application under 35 U.S.C. § 371 of International Application No. PCT/SG2015/050015, filed Feb. 6, 2015, entitled 2,4,5-TRI-SUBSTITUTED AZOLE-BASED CASEIN KINASE 1 INHIBITORS AS INDUCERS FOR CARDIOMYOGENESIS, which claims priority to Singapore Patent Application No. 2014009815, filed Feb. 7, 2014.

TECHNICAL FIELD

The present invention generally relates to the method for inducing or enhancing the differentiation of pluripotent stem cells into cardiomyocytes via casein kinase 1 inhibition said method comprising culturing the stem cells in the presence of a medium comprising a casein kinase 1 inhibitor which is a 2,4,5-tri-substituted azole compound. The present invention also relates to new 2,4,5-tri-substituted azoles and the use of 2,4,5-tri-substituted azoles in the above methods.

BACKGROUND ART

In regenerative medicine significant progress has been made in stem cell therapy. Heart diseases which are associated with the degeneration of cardiomyocytes may be treated via the use of stem cells. Such stem cells, especially human embryonic stem cells (hESCs), need to be differentiated into cardiomyocytes. For such differentiation the use of small molecules has been found to be a particularly advantageous way to support the differentiation process. Such small molecules can be synthesized easily, are reversible with respect to effect on cells, and can be administered temporarily. One suitable molecule that has been reported is SB203580 (cf. WO2013056072 A1, US20130189785) which is used as a p38α MAPK inhibitor in the differentiation pathway.

It has been further found that a preferred method to generate cardiomyocytes is to inhibit the canonical Wnt pathway at certain time points during the differentiation process. Although there are many potent inhibitors which can inhibit parts of the Wnt pathway, research thus far indicates that only inhibition of porcine and tankyrase within the canonical Wnt pathway was effective in generating cardiomyocytes. This limits the number of suitable small molecules which can be utilized for cardiomyocyte differentiation.

Furthermore there is a need for more efficient methods to generate cardiomyocytes via the embryonic body (EB) suspension culture method which can be scaled in bioreactors for future stem cells therapy, research and pharmacological drug testing. All applications demand cardiomyocytes of high quality (i.e. functionality based on parameters such as beat count, beating area, and beating frequency) and in high quantity. There is still a need to overcome difficulties associated with low efficiency (<10%) and the poor yields of conventional cardiomyocyte differentiation protocols via EBs.

There is therefore a need to address the Wnt pathway in a different way utilizing other time points and/or new small molecules to provide a method that overcomes, or at least ameliorates, one or more of the disadvantages described above.

SUMMARY OF INVENTION

According to a first aspect, there is provided a method for inducing or enhancing the differentiation of pluripotent stem cells into cardiomyocyte via casein kinase 1 inhibition said method comprising culturing the stem cells in the presence of a medium comprising a casein kinase 1 inhibitor of the formula (I) or (II) or a stereoisomer, tautomer, or a salt thereof:

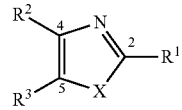
[Formula (I)]

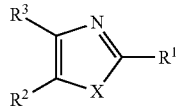
[Formula (II)]

wherein $R^1$, $R^2$ and $R^3$ independently from another represent hydrogen, optionally substituted alkyl, alkenyl, alkynyl, heterocyclyl, heteroaryl or aryl;
X represents $NR^4$, O or S; and
$R^4$ represents hydrogen, optionally substituted alkyl, alkenyl, alkynyl, heterocyclyl, heteroaryl or aryl.

Advantageously the use of small molecules that inhibit Wnt pathway during cardiomyocyte differentiation of pluripotent stem cells via casein kinase 1 (CK1 or CK 1) inhibition leads to improved differentiation. Differentiation of cardiomyocytes via inhibition of CK1 can be used on human induced pluripotent stem cells and human embryonic stem cells after EB formation, preferably from day 2 onwards. The small molecules according to the invention target CK 1 epsilon and CK 1 delta to give 10-20% cardiomyocytes when applied as the sole inhibitor which is significantly better compared to other inhibition pathway methods. In the method of the invention not only the Wnt pathway, but also the stress pathway, is addressed. This double inhibition of Wnt and cell stress pathways according to the inventive method is unique. Wnt pathway inhibition is known to inhibit growth in cells. Many protocols compensate for this effect with highly expensive differentiation medium supplements (e.g. B27) that provides several growth factors to compensate for growth inhibition and boost cell growth. Such compensation is not needed with the use of selected small molecules according to the inventive method.

According to the invention the compounds of formula (I), (Ia), (Ia)' and (II), especially IM-31 and ZQX-19, can therefore be used in methods to promote cell growth and survival.

According to a second aspect of the invention the casein kinase 1 inhibitor is added about 3 to 4 days after the mesoderm has been established. This allows the use of small molecules which specifically address the CK1 inhibition of the Wnt pathway at this later stage. Advantageously, small molecules of formula (I) or (II) then even show an action which is not present when they are used earlier (day 0-2). The late application window also improves the results on differentiation as shown by higher percentages of cardiomyocytes obtained. A set time frame between days 3 to 8 allows a wider range of compounds to be tested using the method of the invention without changing the concentration of the small molecules added. This is a great advantage, which can reduce the number of experiments to one concentration and one time course in order to investigate the correlations between a compound's in vitro effect on target protein(s) and its cardiomyogenic activity. Moreover the effect of the compounds of formula (I) or (II) on cardiomyogenesis in the days 4 to 8 time course indicates a preferred new late stage application time slot.

According to a third aspect of the invention there is provided a method wherein the compound CHIR99021 is added to the embryoid bodies after the mesoderm has been established.

Advantageously this results in even higher yields of cardiomyocytes of over 50%.

According to a fourth aspect of the invention there is provided novel compounds. Such compounds include compounds of the formula (I) or (II) or a stereoisomer, tautomer, or salt thereof:

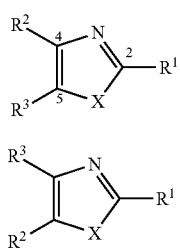

[Formula (I)]

[Formula (II)]

wherein $R^1$ represents fluorine substituted monovalent and divalent, single, polynuclear, conjugated and fused residues of aromatic hydrocarbons having from 6 to 10 carbon atoms; $R^2$ represents fluorine substituted aromatic hydrocarbons having 6 carbon atoms;
$R^3$ represents saturated 5 to 6 ring membered heterocycloalkyl having 1 to 3 hetero atoms selected from N or O, or an aromatic radical having 5 to 6 ring atoms wherein 1 to 3 atoms are heteroatoms selected from O and N; and
X represents NH or O.

Advantageously these novel group of compounds and the other compounds described in the specification have been proven to be especially well suited to use in the method of the invention and to achieve the abovementioned benefits of improved differentiation.

According to a fifth aspect of the invention there is provided a kit for use in stem cell differentiation to cardiomyocytes via inhibition of casein kinase 1 comprising a compound of the formula (I) or (II), or a stereoisomer, tautomer, or a salt thereof:

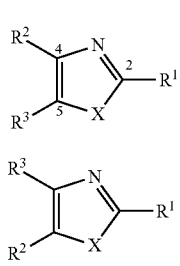

[Formula (I)]

[Formula (II)]

wherein $R^1$, $R^2$ and $R^3$ independently from another represent hydrogen, optionally substituted alkyl, alkenyl, alkynyl, heterocyclyl, heteroaryl or aryl;
X represents $NR^4$, O or S; and
$R^4$ represents hydrogen, optionally substituted alkyl, alkenyl, alkynyl, heterocyclyl, heteroaryl or aryl.

Definitions

The following words and terms used herein shall have the meaning indicated:

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations or any two or more of said steps or features.

As used herein, the term "alkyl group" includes within its meaning monovalent ("alkyl") and divalent ("alkylene") straight chain or branched chain saturated aliphatic groups having from 1 to 10 carbon atoms, eg, 1, 2, 3, 4, 5, 6, 7, 8, 9, or 10 carbon atoms. For example, the term alkyl includes, but is not limited to, methyl, ethyl, 1-propyl, isopropyl, 1-butyl, 2-butyl, isobutyl, tert-butyl, amyl, 1,2-dimethylpropyl, 1,1-dimethylpropyl, pentyl, isopentyl, hexyl, 4-methylpentyl, 1-methylpentyl, 2-methylpentyl, 3-methylpentyl, 2,2-dimethylbutyl, 3,3-dimethylbutyl, 1,2-dimethylbutyl, 1,3-dimethylbutyl, 1,2,2-trimethylpropyl, 1,1,2-trimethylpropyl, 2-ethylpentyl, 3-ethylpentyl, heptyl, 1-methylhexyl, 2,2-dimethylpentyl, 3,3-dimethylpentyl, 4,4-dimethylpentyl, 1,2-dimethylpentyl, 1,3-dimethylpentyl, 1,4-dimethylpentyl, 1,2,3-trimethylbutyl, 1,1,2-trimethylbutyl, 1,1,3-trimethylbutyl, 5-methylheptyl, 1-methylheptyl, octyl, nonyl, decyl, and the like.

The term "alkenyl group" includes within its meaning monovalent ("alkenyl") and divalent ("alkenylene") straight or branched chain unsaturated aliphatic hydrocarbon groups having from 2 to 10 carbon atoms, e.g., 2, 3, 4, 5, 6, 7, 8, 9, or 10 carbon atoms and having at least one double bond, of either E, Z, cis or trans stereochemistry where applicable, anywhere in the alkyl chain. Examples of alkenyl groups include but are not limited to ethenyl, vinyl, allyl, 1-methylvinyl, 1-propenyl, 2-propenyl, 2-methyl-1-propenyl, 2-methyl-1-propenyl, 1-butenyl, 2-butenyl, 3-butentyl, 1,3-butadienyl, 1-pentenyl, 2-pententyl, 3-pentenyl, 4-pentenyl, 1,3-pentadienyl, 2,4-pentadienyl, 1,4-pentadienyl, 3-methyl-2-butenyl, 1-hexenyl, 2-hexenyl, 3-hexenyl, 1,3-hexadienyl, 1,4-hexadienyl, 2-methylpentenyl, 1-heptenyl, 2-heptentyl, 3-heptenyl, 1-octenyl, 1-nonenyl, 1-decenyl, and the like.

The term "alkynyl group" as used herein includes within its meaning monovalent ("alkynyl") and divalent ("alkynylene") straight or branched chain unsaturated aliphatic hydrocarbon groups having from 2 to 10 carbon atoms and having at least one triple bond anywhere in the carbon chain. Examples of alkynyl groups include but are not limited to ethynyl, 1-propynyl, 1-butynyl, 2-butynyl, 1-methyl-2-butynyl, 3-methyl-1-butynyl, 1-pentynyl, 1-hexynyl, methylpentynyl, 1-heptynyl, 2-heptynyl, 1-octynyl, 2-octynyl, 1-nonyl, 1-decynyl, and the like.

The term "cycloalkyl" as used herein refers to cyclic saturated aliphatic groups and includes within its meaning monovalent ("cycloalkyl"), and divalent ("cycloalkylene"), saturated, monocyclic, bicyclic, polycyclic or fused polycyclic hydrocarbon radicals having from 3 to 10 carbon atoms, e.g., 3, 4, 5, 6, 7, 8, 9, or 10 carbon atoms. Examples of cycloalkyl groups include but are not limited to cyclopropyl, 2-methylcyclopropyl, cyclobutyl, cyclopentyl, 2-methylcyclopentyl, 3-methylcyclopentyl, cyclohexyl, and the like.

"Heterocyclyl" or "heterocyclic" refer to a saturated or unsaturated group having a single ring or multiple condensed rings, from 1 to 10 carbon atoms and from 1 to 4 hetero atoms selected from the group consisting of nitrogen, sulfur or oxygen within the ring wherein, in fused ring systems, one or more the rings can be cycloalkyl, aryl or heteroaryl provided that the point of attachment is through the heterocyclic ring. Examples of heterocyclyls include, but are not limited to pyridinyl, pyrrolyl, indolyl, thienyl, furyl, benzothienyl, benzofuranyl, imidazolyl, benzoimidazolyl, pyrazolyl, thiazolyl, benzothiazolyl, isothiazolyl, oxazolyl, isoxazolyl, pyrazinyl, pyrimidinyl, pyridazinyl, isoindolyl, purinyl, quinolyl, isoquinolyl, dihydroquinolinyl, 2,3-dihydro-1H-indolyl, quinoxalinyl, benzodioxolyl, indanyl, indenyl, triazolyl, azetidinyl, indolizinyl, dihydroindolyl, indazolyl, quinolizinyl, phthalazinyl, naphthylpyridinyl, quinazolinyl, cinnolinyl, pteridinyl, carbazolyl, carbolinyl, phenanthridinyl, acridinyl, phenanthrolinyl, phenazinyl, phenoxazinyl, phenothiazinyl, imidazolidinyl, imidazolinyl, piperidinyl, piperazinyl, indolinyl, phthalimidyl, 1,2,3,4-tetrahydro-isoquinolinyl, 4,5,6,7-tetrahydrobenzo[b]thiophenyl, thiazolidinyl, morpholinyl, thiomorpholinyl (also referred to as thiamorpholinyl), piperidinyl, pyrrolidinyl, pyrrolinyl, pyrazolinyl, pyrazolidinyl and tetrahydrofuranyl.

The term "aryl" as used herein refers to monovalent ("aryl") and divalent ("arylene") single, polynuclear, conjugated and fused residues of aromatic hydrocarbons having from 6 to 10 carbon atoms. Examples of such groups include phenyl, biphenyl, naphthyl, phenanthrenyl, and the like.

The term "heteroaromatic group" and variants such as "heteroaryl" or "heteroarylene" as used herein, includes within its meaning monovalent ("heteroaryl") and divalent ("heteroarylene"), single, polynuclear, conjugated and fused aromatic radicals having 6 to 20 atoms wherein 1 to 6 atoms are heteroatoms selected from O, N, NH and S. Examples of such groups include pyridyl, 2,2'-bipyridyl, phenanthrolinyl, quinolinyl, thiophenyl, and the like.

The term "aromatic radical" may refer to aryl or heteroaryl radicals unless otherwise specified.

The term "halogen" or variants such as "halide" or "halo" as used herein refers to fluorine, chlorine, bromine and iodine.

The term "heteroatom" or variants such as "hetero-" as used herein refers to O, N, NH and S.

The term "aralkyl" as used herein, includes within its meaning ("aryl") and divalent ("arylene"), single, polynuclear, conjugated and fused aromatic hydrocarbon radicals attached to divalent, saturated, straight and branched chain $C_1$-$C_6$-alkylene radicals.

The term "heteroaralkyl" as used herein, includes within its meaning monovalent ("heteroaryl") and divalent ("heteroarylene"), single, polynuclear, conjugated and fused aromatic hydrocarbon radicals attached to divalent saturated, straight and branched chain $C_1$-$C_6$-alkylene radicals.

Preferably the aryl or arylene in the aralkyl has 6 or 10 carbon atoms. Preferably the heteroaryl or heteroarylene in the heteroaralkyl forms a five or six membered ring having 1 to 3 hetero atoms selected from N, S or O.

The term "optionally substituted" as used herein means the group to which this term refers may be unsubstituted, or may be substituted with one or more groups independently selected from $C_1$-$C_6$-alkyl, $C_2$-$C_6$-alkenyl, $C_2$-$C_6$-alkynyl, thio-$C_1$-$C_6$-alkyl, $C_3$-$C_8$-cycloalkyl, $C_3$-$C_8$-cycloalkenyl, five to six membered heterocycloalkyl, halo, —COOH, —CONH$_2$, $C_1$-$C_6$-carboxyl, halo-$C_1$-$C_6$-alkyl, halo-$C_2$-$C_6$-alkynyl, hydroxyl, $C_1$-$C_6$-alkoxy, thio-$C_1$-$C_6$-alkoxy, $C_2$-$C_6$-alkenyloxy, halo-$C_1$-$C_6$-alkoxy, halo-$C_2$-$C_6$-alkenyloxy, nitro, amino, nitro-$C_1$-$C_6$-alkyl, nitro-$C_2$-$C_6$-alkenyl, nitro-$C_2$-$C_6$-alkynyl, five to six ring membered nitro-heterocyclyl, $C_1$-$C_6$-alkylamino, di-$C_1$-$C_6$-alkylamino, $C_2$-$C_6$-alkenylamine, $C_2$-$C_6$-alkynylamino, $C_1$-$C_6$-acyl, $C_2$-$C_6$-alkenoyl, $C_2$-$C_6$-alkynoyl, $C_1$-$C_6$-acylamino, di-$C_1$-$C_6$-acylamino, $C_1$-$C_6$-acyloxy, $C_1$-$C_6$-alkylsulfonyloxy, five to six ring membered heterocyloxy, five to six ring membered heterocycloamino, five to six ring membered haloheterocycloalkyl, $C_1$-$C_6$-alkylsulfenyl, $C_1$-$C_6$-alkylcarbonyloxy, $C_1$-$C_6$-alkylthio, $C_1$-$C_6$-acylthio, phosphorus-containing groups such as phosphono and phosphinyl, aryl having 6 to 10 carbon atoms, five to six ring membered heteroaryl, $C_1$-$C_4$-alkylaryl having 6 or 10 carbon atoms in the aryl, five to six ring membered $C_1$-$C_6$-alkylheteroaryl, cyano, cyanate, isocyanate, —C(O)NH($C_1$-$C_6$-alkyl), and —C(O)N($C_1$-$C_6$-alkyl)$_2$. If the term "optionally substituted" is used it refers to all substituents listed after this term, e.g. "optionally substituted methyl or ethyl" means "optionally substituted methyl" or optionally substituted ethyl". The term "substituted" as used herein means the group to which this term refers may be is substituted with one or more groups which are independently selected from the list of substituents mentioned.

The present invention includes within its scope all isomeric forms of the compounds disclosed herein, including all tautomers, diastereomeric isomers, racemates and enantiomers, unless the stereochemistry is fixed in the formula drawing. Thus, the formulas should be understood to include, for example, E, Z, cis, trans, (R), (S), (L), (D), (+), and/or (−) forms of the compounds, as appropriate in each case, unless the stereochemistry is fixed in the formula drawing. Tautomers can be especially mentioned.

Unless specified otherwise, the terms "comprising" and "comprise", and grammatical variants thereof, are intended to represent "open" or "inclusive" language such that they include recited elements but also permit inclusion of additional, unrecited elements.

As used herein, the term "about", in the context of concentrations of components of the formulations, typically means +/−5% of the stated value, more typically +/−4% of the stated value, more typically +/−3% of the stated value, more typically, +/−2% of the stated value, even more typically +/−1% of the stated value, and even more typically +/−0.5% of the stated value.

Throughout this disclosure, certain embodiments may be disclosed in a range format. It should be understood that the description in range format is merely for convenience and brevity and should not be construed as an inflexible limitation on the scope of the disclosed ranges. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Certain embodiments may also be described broadly and generically herein. Each of the narrower species and subgeneric groupings falling within the generic disclosure also form part of the disclosure. This includes the generic description of the embodiments with a proviso or negative limitation removing any subject matter from the genus, regardless of whether or not the excised material is specifically recited herein.

DETAILED DISCLOSURE OF EMBODIMENTS

Non-limiting examples of the invention and a comparative example will be further described in greater detail by reference to specific examples, which should not be construed as in any way limiting the scope of the invention.

According to a first aspect, there is provided a method for inducing or enhancing the differentiation of pluripotent stem cells into cardiomyocyte via casein kinase 1 inhibition said method comprising culturing the stem cells in the presence of a medium comprising a casein kinase 1 inhibitor of the formula (I) or (II) or a stereoisomer, tautomer, or a salt thereof:

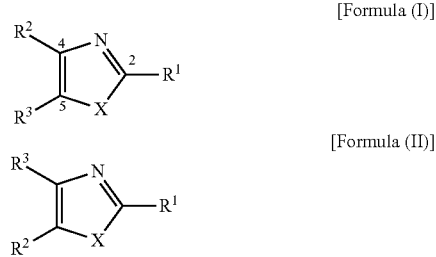

[Formula (I)]

[Formula (II)]

wherein $R^1$, $R^2$ and $R^3$ independently from another represent hydrogen, optionally substituted alkyl, alkenyl, alkynyl, heterocyclyl, heteroaryl or aryl;
X represents $NR^4$, O or S; and
$R^4$ represents hydrogen, optionally substituted alkyl, alkenyl, alkynyl, heterocyclyl, heteroaryl or aryl.

The casein kinase inhibitor is preferably selected from casein kinase 1δ (delta) inhibitors or casein kinase 1ε (epsilon) inhibitors. Therefore according to the method the canonical pathway of Wnt inhibition is addressed by CK 1δ and/or CK 1ε inhibition.

The inhibition of the Wnt pathway has been done in a mesoderm developmental stage of the stem cells. The small molecules in according to formula (I), (Ia), (Ia)' and (II) can work independently of those time course restrictions due to their mechanism of action on CK1. Compared to other protocols for generating cardiomyocytes, the usage of the presented small molecules is flexible.

The pluripotent stem cells in the method of the invention can be human induced pluripotent stem cells (hiPSCs) or human embryonic stem cells (hESCs). They can be harvested as embryonic bodies (EBs) according to known methods and used as such in the culture medium for differentiation according to the inventive method. The small molecules of formula (I), (Ia), (Ia)' and (II) are added according to specific time points as mentioned below. The 2,4,5-tri-substituted azoles for cardiac differentiation are robust across several embryonic-, and induced pluripotent stem cell lines.

The inventive method can be applied on different cell culture platforms. Cell culture platforms that can be especially mentioned are embryonic bodies and microcarriers. Microcarriers (MC) are tiny spheres or particles (typically 90-300 µm in diameter) used for culturing adherent cells in stirred-tank bioreactors. EBs are 3-dimensional cell aggregates that mimic some structure of the developing embryo and can differentiate into cells of all three germ layers. EBs are beneficiary in the initiation of lineage-specific differentiation towards many lineages such as cardiac.

The inventive method can be modified to have a harvesting step at the end about 10 to 12 days after the start of the differentiation.

The compounds of formula (I), (Ia), (Ia)' and (II) can be used in the typical concentration ranges of small molecules in such culture medium differentiation such as 0.5 to 20 µM, preferably 1 to 10 µM. However the compounds can also be effectively added at concentrations below 3 µM. A concentration range of 0.1 to 3 µM can be specifically mentioned. Preferred concentrations that still lead to very good differentiation results include 0.5 µM, 1 µM, 2 µM, 3 µM or 5 µM.

The cultivation temperature in the inventive methods during differentiation is usually about 37° C.

The medium for the cultivation of the stem cells can be a typical cultivation medium known in the art, such as basic serum free stem cell medium. Examples of suitable media and excipients are given in the examples. Such media include DMEM or RPMI with or without B27 supplements. The choice of the medium is however not critical.

The compound of formula (I), (Ia), (Ia)' and (II) can be used at different times during cell culturing, such as either from days 1-8, 2-6, 3-6 or from days 4-8 of the differentiation. Differentiation of cardiomyocytes via inhibition of CK1 can be used on human induced pluripotent stem cells and human embryonic stem cells after EB formation from day 2 onwards. Preferably the compound is added at day 1 to 8, 3 to 8 or 4 to 8 of the differentiation process after the mesoderm has been established.

The compound of formula (I), (Ia), (Ia)' and (II) can be used with several embryonic-, and induced pluripotent stem cell lines.

The compound of formula (I), (Ia), (Ia)' and (II) can be used on different 2D and 3D cell culture platforms such as embryoid bodies or microcarrier culture platforms known in the art.

According to a second aspect of the invention the casein kinase inhibitor is added about 3 to 4 days after the mesoderm has been established. Addition according to this embodiment is therefore during the late (post mesoderm) development of cardiomyocytes. This later addition of the inhibitor is only possible by using the inventive method which specifically addresses the CK 1 inhibition. Different differentiation results are obtained by later addition of the compound of formula (I), (Ia), (Ia)' and (II) then the usual addition on day 1-2 to 8. The reason is that in such preferred method only the CK 1 inhibition is used specifically. The method according to the invention is therefore suited to influence only the late (post mesoderm) development of cardiomyocytes (days 4 to 8 of differentiation). Such method has thus been unknown and leads to better differentiation rates.

In another embodiment of the method the casein kinase inhibitor is added from about day 3 to 8 after the mesoderm has been established. This means that the casein kinase inhibitor is present during this time after single addition or continuously added over the whole time.

From the embodiments it can be seen that the CK 1 inhibitor is present from day 3 to 8, or 4 to 8, during differentiation.

In formula (I) and (II), $R^1$, $R^2$, $R^3$ and $R^4$ and X have the following preferred definitions:
$R^1$, $R^2$, $R^3$ and $R^4$ preferably independently from another represent hydrogen, optionally substituted straight chain or branched chain saturated aliphatic groups having from 1 to 10 carbon atoms, optionally substituted straight or branched chain unsaturated aliphatic hydrocarbon groups having from 2 to 10 carbon atoms, optionally substituted straight or branched chain unsaturated aliphatic hydrocarbon groups having from 2 to 10 carbon atoms and having at least one triple bond anywhere in the carbon chain, optionally substituted, unsaturated or saturated 5 to 6 ring membered heterocycloalkyl having 1 to 3 hetero atoms selected from N, S, or O, optionally substituted heteroaromatic radicals having 5 to 6 ring atoms wherein 1 to 3 atoms are heteroatoms selected from O, N, NH and S or optionally substituted monovalent and divalent, single, polynuclear, conjugated and fused residues of aromatic hydrocarbons having from 6 to 10 carbon atoms, and the optional substituents are in each case independently selected from one or more groups independently selected from $C_1$-$C_6$-alkyl, $C_2$-$C_6$-alkenyl, $C_2$-$C_6$-alkynyl, thio-$C_1$-$C_6$-alkyl, $C_3$-$C_8$-cycloalkyl, $C_3$-$C_8$-cycloalkenyl, five to six membered heterocycloalkyl, halo, —COOH, —CONH$_2$, $C_1$-$C_6$-carboxyl, halo-$C_1$-$C_6$-alkyl, halo-$C_2$-$C_6$-alkynyl, hydroxyl, $C_1$-$C_6$-alkoxy, $C_1$-$C_6$-alkoxycarbonyl, thio-$C_1$-$C_6$-alkoxy, $C_2$-$C_6$-alkenyloxy, halo-$C_1$-$C_6$-alkoxy, halo-$C_2$-$C_6$-alkenyloxy, nitro, amino, N-hydroxy-imidamide, nitro-$C_1$-$C_6$-alkyl, nitro-$C_2$-$C_6$-alkenyl, nitro-$C_2$-$C_6$-alkynyl, five to six ring membered nitroheterocyclyl, $C_1$-$C_6$-alkylamino, di-$C_1$-$C_6$-alkylamino, $C_2$-$C_6$-alkenylamine, $C_2$-$C_6$-alkynylamino, $C_1$-$C_6$-acyl, $C_2$-$C_6$-alkenoyl, $C_2$-$C_6$-alkynoyl, $C_1$-$C_6$-acylamino, di-$C_1$-$C_6$-acylamino, $C_1$-$C_6$-acyloxy, $C_1$-$C_6$-alkylsulfonyloxy, five to six ring membered heterocycloxy, five to six ring membered heterocycloamino, five to six ring membered haloheterocycloalkyl, $C_1$-$C_6$-alkylsulfenyl, $C_1$-$C_6$-alkylsulfinyl, $C_1$-$C_6$-alkylsulfonyl, $C_1$-$C_6$-alkylsulfinylamino, $C_1$-$C_6$-alkylsulfonylamino, $C_1$-$C_6$-alkylcarbonyloxy, $C_1$-$C_6$-alkylthio, $C_1$-$C_6$-acylthio, phosphorus-containing groups such as phosphono and phosphinyl, aryl having 6 to 10 carbon atoms, five to six ring membered heteroaryl, $C_1$-$C_4$-alkylaryl having 6 or 10 carbon atoms in the aryl, five to six ring membered $C_1$-$C_6$-alkylheteroaryl, cyano, cyanate, isocyanate, —C(O)NH($C_1$-$C_6$-alkyl), or —C(O)N($C_1$-$C_6$-alkyl)$_2$ or two substituents forming an —O—$C_2$-$C_6$-alkyl-O— bridge.

$R^1$ preferably represents hydrogen, optionally substituted straight chain or branched chain saturated aliphatic groups having from 1 to 10 carbon atoms, optionally substituted straight or branched chain unsaturated aliphatic hydrocarbon groups having from 2 to 10 carbon atoms, optionally substituted straight or branched chain unsaturated aliphatic hydrocarbon groups having from 2 to 10 carbon atoms and having at least one triple bond anywhere in the carbon chain, or optionally substituted monovalent and divalent, single, polynuclear, conjugated and fused residues of aromatic hydrocarbons having from 6 to 10 carbon atoms. Optionally substituted aromatic hydrocarbons having from 6 to 10 carbon atoms can be especially mentioned.

$R^1$ more preferably represents halogen substituted monovalent and divalent, single, polynuclear, conjugated and fused residues of aromatic hydrocarbons having from 6 to 10 carbon atoms. In this regard "halogen substituted" means that the corresponding moiety is at least substituted by one halogen, but can optionally be additionally substituted by other substituents. Fluorine is a preferred halogen. In this regard "fluorine substituted" means that the corresponding moiety is at least substituted by one fluorine, but can optionally be additionally substituted by other substituents.

$R^1$ most preferably represents fluorine substituted aryl having 6 to 10 carbon atoms. In this regard "fluorine substituted" means that the corresponding moiety is at least substituted by one fluorine, but can optionally be additionally substituted by other substituents. $R^1$ then preferably represents fluorine substituted $C_6$ to $C_{10}$ aryl which is optionally additionally substituted by one or more substituents selected from amino, —COOH, hydroxyl, $C_1$-$C_4$-alkyl, $C_1$-$C_4$-alkoxy, $C_1$-$C_4$-alkoxycarbonyl, chlorine, bromine, iodine, nitro or a —O—$C_1$-$C_4$-alkyl-O— bridge. $R^2$ that represents a moiety that is only substituted by one or more fluorine atoms and no other substituents may however be specially mentioned.

$R^2$ preferably represents an optionally substituted aromatic radical having 6 atoms wherein 1 to 3 atoms are heteroatoms selected from O, N, NH and S or optionally substituted monovalent and divalent, single, polynuclear, conjugated and fused residues of aromatic hydrocarbons having from 6 to 10 carbon atoms.

$R^2$ more preferably represents halogen substituted aromatic hydrocarbons having 6 carbon atoms. In this regard "halogen substituted" means that the corresponding moiety is at least substituted by one halogen, but can optionally be additionally substituted by other substituents. Fluorine is a preferred halogen. In this regard "fluorine substituted" means that the corresponding moiety is at least substituted by one fluorine, but can optionally be additionally substituted by other substituents.

$R^2$ most preferably represents fluorine substituted phenyl. In this regard "fluorine substituted" means that the corresponding moiety is at least substituted by one fluorine, but can optionally be additionally substituted by other substituents. $R^2$ then preferably represents fluorine substituted phenyl which is optionally additionally substituted by one or more substituents selected from amino, —COOH, hydroxyl, $C_1$-$C_4$-alkyl, $C_1$-$C_4$-alkoxy, $C_1$-$C_4$-alkoxycarbonyl, chlorine, bromine, iodine or nitro. $R^2$ that represents a moiety that is only substituted by one or more fluorine atoms and no other substituents may however be specially mentioned.

$R^3$ more preferably represents optionally substituted, unsaturated or saturated 5 to 6 ring membered heterocycloalkyl having 1 to 3 hetero atoms selected from N, S, or O, optionally substituted heteroaromatic radicals having 6 atoms wherein 1 to 3 atoms are heteroatoms selected from O, N, NH and S, or optionally substituted monovalent and divalent, single, polynuclear, conjugated and fused residues of aromatic hydrocarbons having from 6 to 10 carbon atoms.

$R^3$ most preferably represents pyridinyl or pyranyl.

X preferably represents NH or O. X most preferably represents NH.

In formula (I) or (II) compounds are preferred which are covered by the proviso that none or only one of $R^1$, $R^2$ or $R^3$ is hydrogen.

Among the compounds of formula (I) there are preferred the compounds for use in the method of the invention according to formula (I)' or a stereoisomer, tautomer, or a salt thereof:

[Formula (I)']

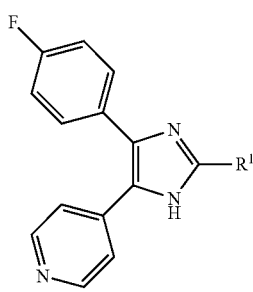

wherein $R^1$ represents phenyl or naphthyl which is substituted by amino, $C_1$-$C_4$-alkyl, $C_1$-$C_4$-alkoxy, halogen, nitro or a —O—$C_1$-$C_4$-alkyl-O— bridge.

Preferably the phenyl or naphthyl of $R^1$ is substituted by amino, methyl, ethyl, methoxy, ethoxy, fluorine, chlorine, bromine, iodine, nitro or a —O—(CH$_2$)—O bridge.

The following compounds are especially well suited to be used in the inventive method. Some of them are novel compounds which are also provided according to the invention, such as:

Compounds of the formula (I) or (II) or a stereoisomer, tautomer, or a salt thereof, wherein $R^1$ represents fluorine substituted monovalent and divalent, single, polynuclear, conjugated and fused residues of aromatic hydrocarbons having from 6 to 10 carbon atoms; $R^2$ represents fluorine substituted aromatic hydrocarbons having 6 carbon atoms; $R^3$ represents saturated 5 to 6 ring membered heterocycloalkyl having 1 to 3 hetero atoms selected from N or O, or an aromatic radical having 5 to 6 ring atoms wherein 1 to 3 atoms are heteroatoms selected from O and N; and X represents NH.

Among the compounds, compounds wherein $R^1$ represents fluorine substituted $C_6$ to $C_{10}$ aryl, $R^2$ represents fluorine substituted phenyl, $R^3$ represents pyridinyl or pyranyl; and X represents NH are preferred.

More preferred are the compounds and their tautomers listed in the following:

[Formula IIIa]

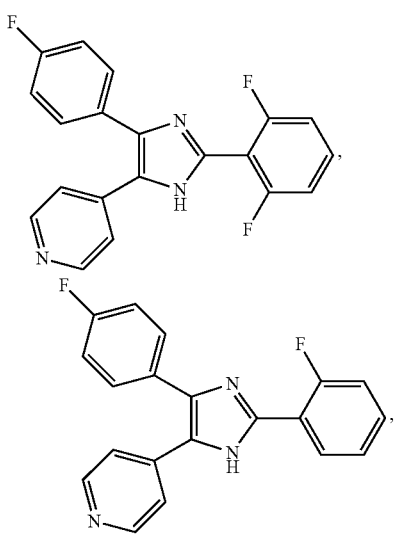

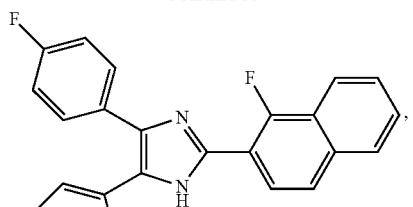

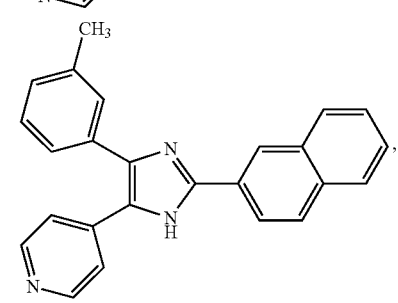

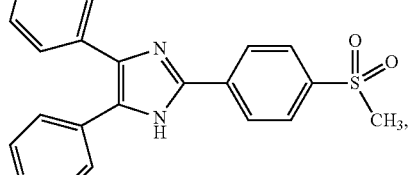

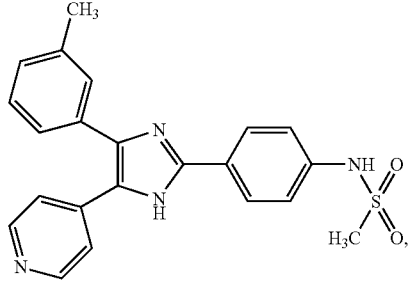

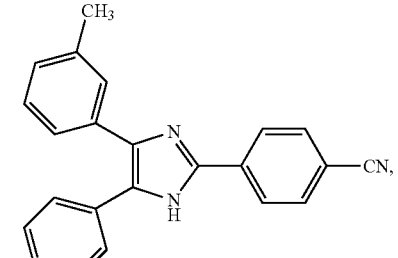

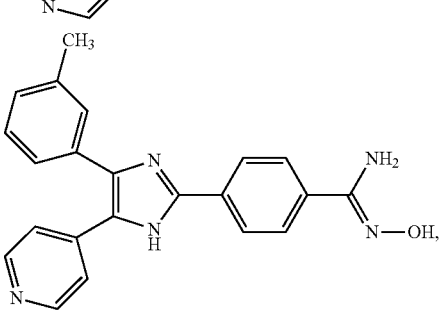

[Formula IIIb]
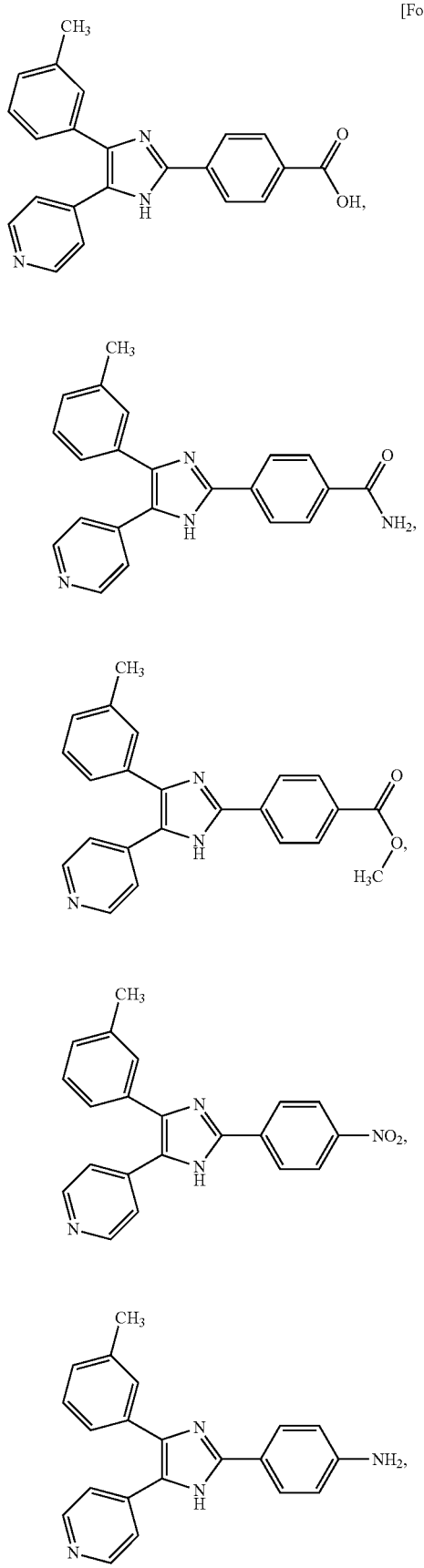
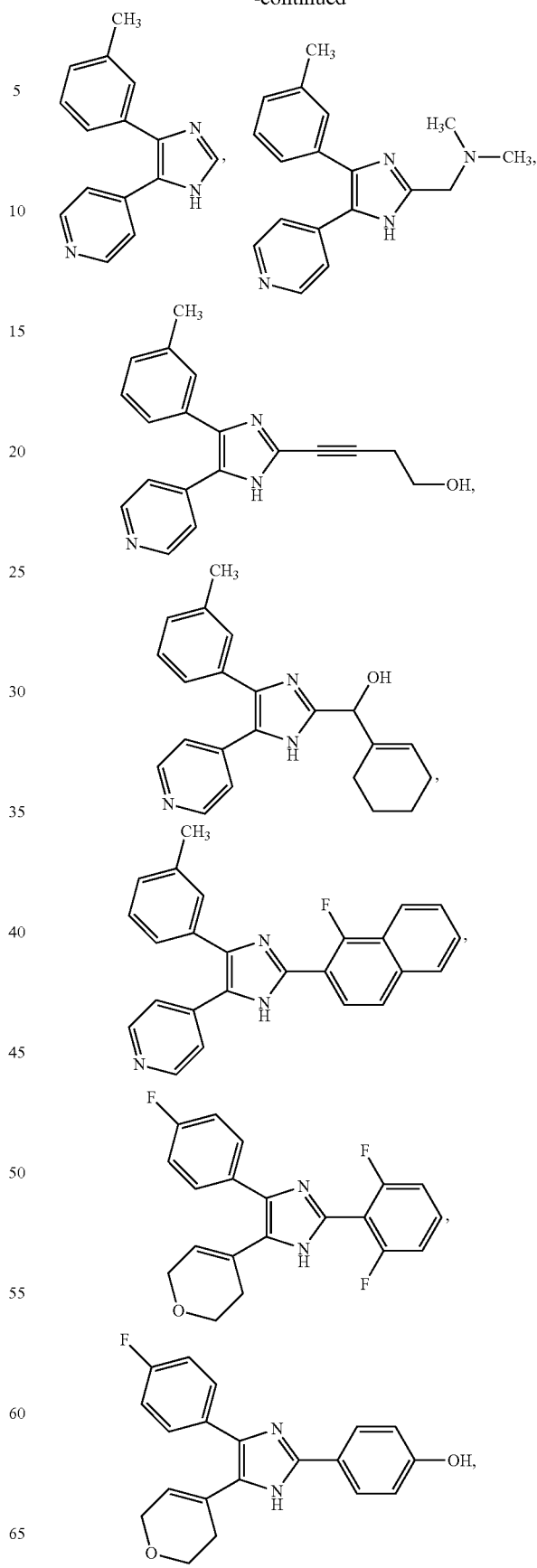

[Formula IIIc]
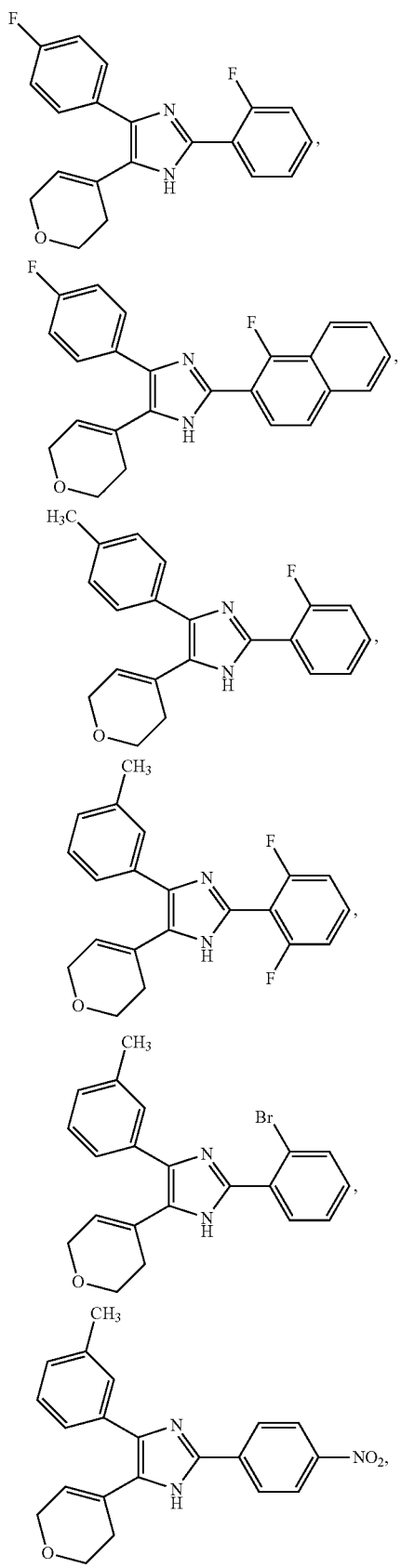
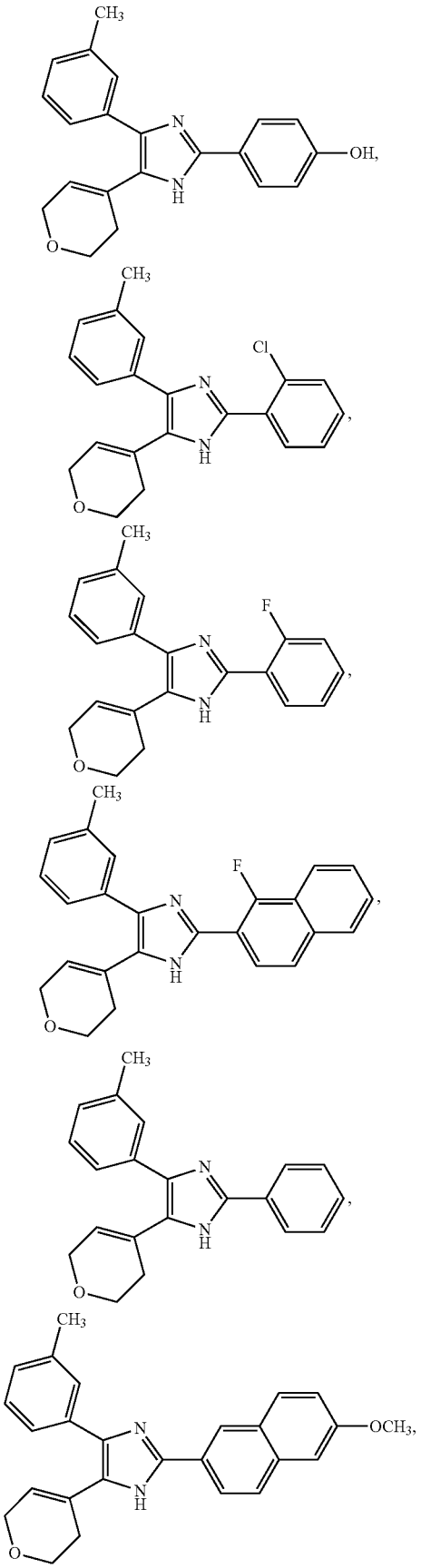

[Formula IIId]
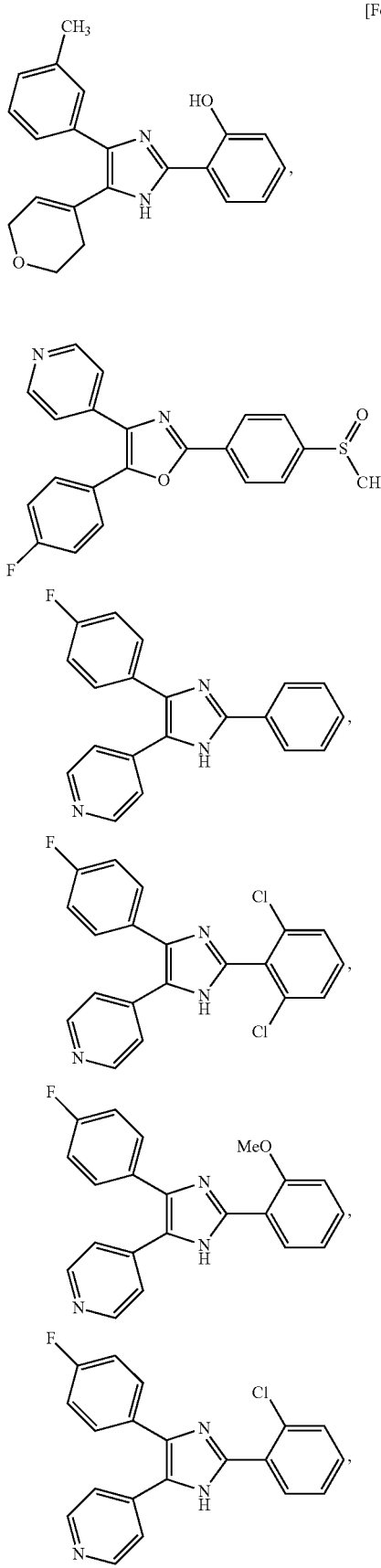
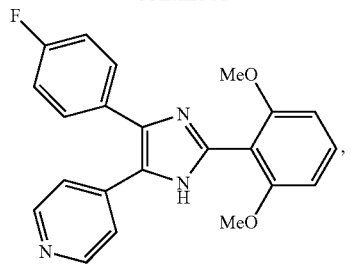

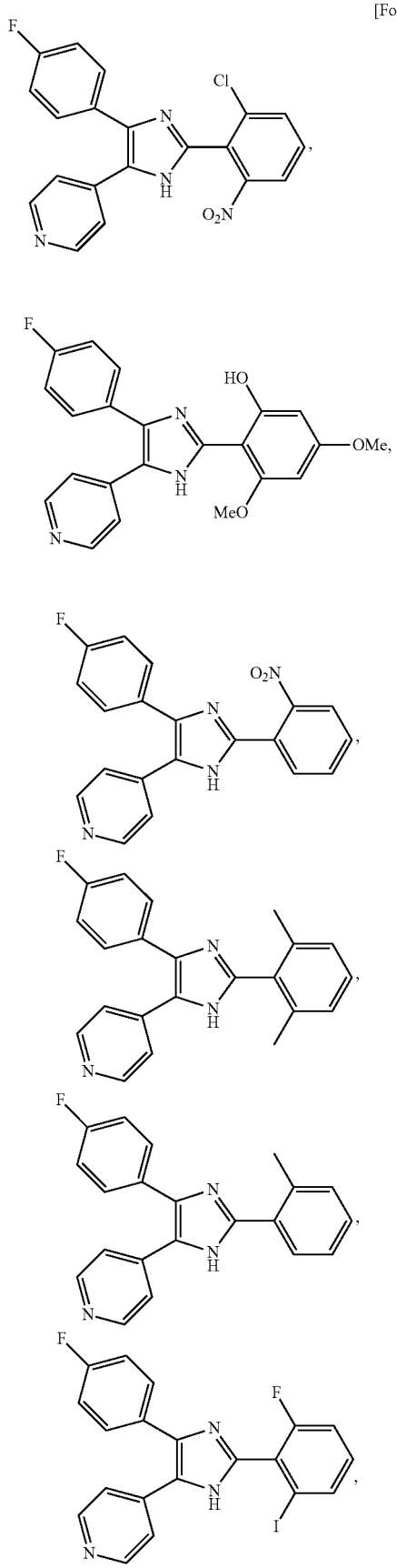

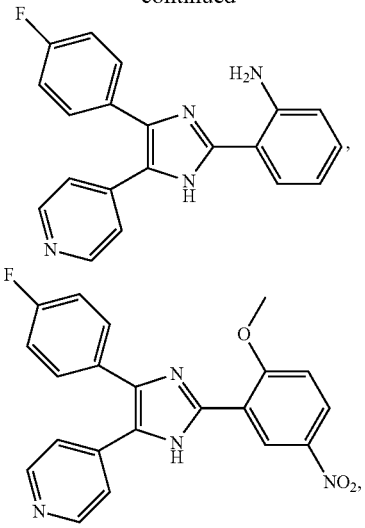

All of these compounds are novel except for 4-[4(5)-(4-fluorophenyl)-2-phenyl-1H-imidazol-5(4)-yl]pyridine (known from U.S. Pat. No. 5,777,097), 4-[2-(2-methoxyphenyl)-4(5)-(4-fluorophenyl)-1H-imidazol-5(4)-yl]pyridine, 4-[2-(2-chlorophenyl)-4(5)-(4-fluorophenyl)-1H-imidazol-5(4)-yl]pyridine, 4-[4(5)-(4-fluorophenyl)-2-(2-nitrophenyl)-1H-imidazol-5(4)-yl]pyridine (known from WO 2004/005264) and 4-[2-(2-bromophenyl)-4(5)-(4-fluorophenyl)-1H-imidazol-5(4)-yl]pyridine (known from WO 2003/024447).

The compound 1a (4-(2-(2,6-difluorophenyl)-4(5)-(4-fluorophenyl)-1H-imidazol-5(4)-yl)pyridine; IM-31, TA-01) or its tautomer can be mentioned as especially preferred and has the following formula (1a):

[Formula 1a]

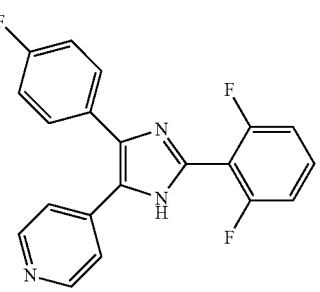

The compound 4-[2-(2-chloro-6-fluorophenyl)-5(4)-(4-fluorophenyl)-3H-imidazol-4(5)-yl]pyridine (ZQX-19) 1a or its tautomer can also be mentioned as especially preferred and has the following formula

[Formula 1b]

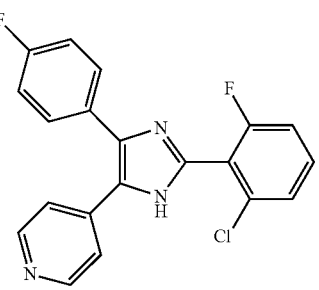

According to the invention it has been found that these compounds have an ability to work as a cardiomyocyte inducer as well as cardiac inhibitor, when applied at high concentration pre mesoderm. This indicated another usage of these compounds beyond cardiac differentiation.

According to the invention the compounds of formula (I), (Ia), (Ia)' and (II) can also be used as cardiac inhibitor at higher concentrations or pre-mesoderm.

Furthermore IM-31 can be used at a 5 times lower concentration than comparable 2,4,5-tri-substituted azole-based casein kinase 1 inhibitors to generate 10-20% cardiomyocytes. The compound is an outstanding compound of high technological significance not just for cardiomyocyte differentiation according to the method of the invention, but also in its ability to inhibit comparable kinase targets of SB203580 more efficiently. Using this compound, also as an example for other compounds according to the invention, a more efficient cardiomyocyte differentiation when compared to IWP-2 (see below) with a simple medium formulation has been achieved.

The compounds 4-(2-(2-fluorophenyl)-4(5)-(4-fluorophenyl)-1H-imidazol-5(4)-yl)pyridine IM-30 (TA-02), 4-[2-(2-chloro-6-fluorophenyl)-4(5)-(4-fluorophenyl)-1H-imidazol-5(4)-yl]pyridine (ZQX-19) and 4-[2-(2-fluoro-6-methoxyphenyl)-4(5)-(4-fluorophenyl)-1H-imidazol-5(4)-yl]pyridine (ZQX-20) are also stronger CK 1 inhibitors than SB203580 and show higher cardiomyocyte differentiation outputs at specific time course. These compounds are also specifically mentioned. It is of technological significance as higher cardiomyocyte yields can be achieved with small molecules such as IM-31 (TA-01), IM-30 (TA-02), ZQX-19 and ZQX-20. Especially with the presented embryoid body based protocol in suspension culture it is possible to scale up the production of cardiomyocytes to a magnitude of therapeutic significance. IM-31 (TA-01) and alternatively TA-01, ZQX-19 and ZQX-20 are able to induce higher cardio differentiation when applied at the specific time course described herein.

Further compounds that can be mentioned for use in the invention are: Compounds of formula (Ia), or a stereoisomer, tautomer, or a salt thereof:

[Formula (Ia)]

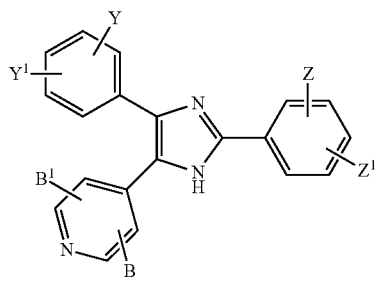

wherein B, B$^1$, Y, Y$^1$, Z and Z$^1$ are absent or each independently selected from $C_1$-$C_6$-alkyl, $C_2$-$C_6$-alkenyl, $C_2$-$C_6$-alkynyl, thio-$C_1$-$C_6$-alkyl, $C_3$-$C_8$-cycloalkyl, $C_3$-$C_8$-cycloalkenyl, five to six membered heterocycloalkyl, halo, —COOH, —CONH$_2$, $C_1$-$C_6$-carboxyl, halo-$C_1$-$C_6$-alkyl, halo-$C_2$-$C_6$-alkynyl, hydroxyl, $C_1$-$C_6$-alkoxy, thio-$C_1$-$C_6$-alkoxy, $C_2$-$C_6$-alkenyloxy, halo-$C_1$-$C_6$-alkoxy, halo-$C_2$-$C_6$-alkenyloxy, nitro, amino, N-hydroxy-imidamide, nitro-$C_1$-$C_6$-alkyl, nitro-$C_2$-$C_6$-alkenyl, nitro-$C_2$-$C_6$-alkynyl, five to six ring membered nitro-heterocyclyl, $C_1$-$C_6$-alkylamino, di-$C_1$-$C_6$-alkylamino, $C_2$-$C_6$-alkenylamine, $C_2$-$C_6$-alkynylamino, $C_1$-$C_6$-acyl, $C_2$-$C_6$-alkenoyl, $C_2$-$C_6$-alkynoyl, $C_1$-$C_6$-acylamino, di-$C_1$-$C_6$-acylamino, $C_1$-$C_6$-acyloxy, $C_1$-$C_6$-alkylsulfonyloxy, five to six ring membered heterocycloxy, five to six ring membered heterocycloamino, five to six ring membered haloheterocycloalkyl, $C_1$-$C_6$-alkylsulfenyl, $C_1$-$C_6$-alkylsulfinyl, $C_1$-$C_6$-alkylsulfonyl, $C_1$-$C_6$-alkylsulfinylamino, $C_1$-$C_6$-alkylsulfonylamino, $C_1$-$C_6$-alkylcarbonyloxy, $C_1$-$C_6$-alkylthio, $C_1$-$C_6$-acylthio, phosphorus-containing groups such as phosphono and phosphinyl, aryl having 6 to 10 carbon atoms, five to six ring membered heteroaryl, $C_1$-$C_4$-alkylaryl having 6 or 10 carbon atoms in the aryl, five to six ring membered $C_1$-$C_6$-alkylheteroaryl, cyano, cyanate, isocyanate, —C(O)NH($C_1$-$C_6$-alkyl), or —C(O)N($C_1$-$C_6$-alkyl)$_{22}$ or two substituents forming an —O—$C_2$-$C_6$-alkyl-O— bridge; provided that at least two of B, B$^1$, Y, Y$^1$, Z and Z1 are not absent.

The compounds of formula (Ia)' can also be used in the inventive method.

[Formula (Ia)']

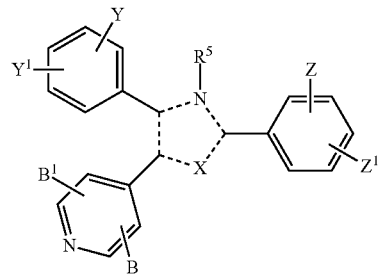

wherein B, B$^1$, Y, Y$^1$, Z and Z$^1$ are absent or each independently selected from $C_1$-$C_6$-alkyl, $C_2$-$C_6$-alkenyl, $C_2$-$C_6$-alkynyl, thio-$C_1$-$C_6$-alkyl, $C_3$-$C_8$-cycloalkyl, $C_3$-$C_8$-cycloalkenyl, five to six membered heterocycloalkyl, halo, —COOH, —CONH$_2$, $C_1$-$C_6$-carboxyl, halo-$C_1$-$C_6$-alkyl, halo-$C_2$-$C_6$-alkynyl, hydroxyl, $C_1$-$C_6$-alkoxy, thio-$C_1$-$C_6$-alkoxy, $C_2$-$C_6$-alkenyloxy, halo-$C_1$-$C_6$-alkoxy, halo-$C_2$-$C_6$-alkenyloxy, nitro, amino, N-hydroxy-imidamide, nitro-$C_1$-$C_6$-alkyl, nitro-$C_2$-$C_6$-alkenyl, nitro-$C_2$-$C_6$-alkynyl, five to six ring membered nitro-heterocyclyl, $C_1$-$C_6$-alkylamino, di-$C_1$-$C_6$-alkylamino, $C_2$-$C_6$-alkenylamine, $C_2$-$C_6$-alkynylamino, $C_1$-$C_6$-acyl, $C_2$-$C_6$-alkenoyl, $C_2$-$C_6$-alkynoyl, $C_1$-$C_6$-acylamino, di-$C_1$-$C_6$-acylamino, $C_1$-$C_6$-acyloxy, $C_1$-$C_6$-alkylsulfonyloxy, five to six ring membered heterocycloxy, five to six ring membered heterocycloamino, five to six ring membered haloheterocycloalkyl, $C_1$-$C_6$-alkylsulfenyl, $C_1$-$C_6$-alkylsulfinyl, $C_1$-$C_6$-alkylsulfonyl, $C_1$-$C_6$-alkylsulfinylamino, $C_1$-$C_6$-alkylsulfonylamino, $C_1$-$C_6$-alkylcarbonyloxy, $C_1$-$C_6$-alkylthio, $C_1$-$C_6$-acylthio, phosphorus-containing groups such as phosphono and phosphinyl, aryl having 6 to 10 carbon atoms, five to six ring membered heteroaryl, $C_1$-$C_4$-alkylaryl having 6 or 10 carbon atoms in the aryl, five to six ring membered $C_1$-$C_6$-alkylheteroaryl, cyano, cyanate, isocyanate, —C(O)NH($C_1$-$C_6$-alkyl), or —C(O)N($C_1$-$C_6$-alkyl)$_2$ or two substituents forming an —O—$C_2$-$C_6$-alkyl-O— bridge;

- - - represents a single bond or double bond;

X represents NR$^4$, O or S;

R$^4$ is absent or represents hydrogen, optionally substituted alkyl, alkenyl, alkynyl, heterocyclyl, heteroaryl or aryl;

R$^5$ is absent or represents hydrogen, optionally substituted alkyl, alkenyl, alkynyl, heterocyclyl, heteroaryl or aryl;

provided that one of $R^4$ or $R^5$ is absent and that at least two of B, $B^1$, Y, $Y^1$, Z and Z1 are not absent.

Compounds of formula (Ia) or (Ia)' wherein at least three of B, $B^1$, Y, $Y^1$, Z and $Z^1$ are not absent can be specifically mentioned as preferred.

The compounds of formula (I), (Ia), (Ia)' and (II) can be prepared as described in the detailed examples or by analogous methods known by the persons skilled in the art.

All these compounds can accordingly be used for inducing or enhancing the differentiation of pluripotent stem cells into cardiomyocytes.

According to a third aspect of the invention there is provided an additional embodiment of the method wherein the compound CHIR99021 is added to the embryoid bodies before the mesoderm has been established.

CHIR99021 is an aminopyrimidine derivative of the formula (IV) that is an extremely potent inhibitor of GSK3, inhibiting GSK3β ($IC_{50}$=6.7 nM) and GSK3α ($IC_{50}$=10 nM) and functions as a Wnt activator.

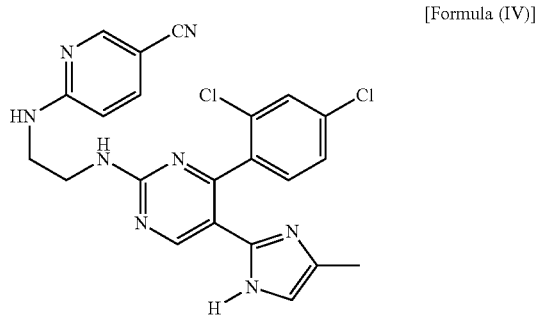 [SMILES: Cc1c[nH]c(-c2cnc(NCCNc3ccc(C#N)cn3)nc2-c2ccc(Cl)cc2Cl)n1]

[Formula (IV)]

According to a preferred embodiment CHIR99021 is added to the stem cell culture before the compounds of the CK 1 inhibitor (preferably on day 0-1 or earlier). Concentrations of CHIR99021 that can be used are in the range of about 0.1 to 20 μM or also 2 to 20 μM, preferably about 0.5 to 5 μM, most preferably about 3 to 7 μM. Such early exposure in the culture medium to CHIR99021 preferably last about 1 to 36 h, more preferably about 10 to 30 h and most preferably about 20 to 28 hours. The pretreatment with CHIR99021 at a high concentration of 3 to 7 μM for about 20 to 28 hours can be followed by a treatment at lower concentration of 0.5 to 2 μM is another embodiment. The CK 1 inhibitor can then be added thereafter (day 1 to 8 or, preferably, on day 3 to 8 or 4 to 8 of differentiation). The late addition on days 3 to 8 or 4 to 8 provides the best results with regard to differentiation obtainable according to this embodiment. The culture medium for the activation step with CHIR99021 can be one ordinarily known in the art, such as those disclosed in the examples.

The pre-treatment with a pre-mesoderm active small molecule, such as CHIR99021, as another step in the method according to the invention is therefore a preferred embodiment of the invention which leads to better yields and differentiation success. The CK 1 inhibitor of the formula (I), (Ia), (Ia)' or (II) is preferably applied at a concentration of 0.5 to 20 μM or 0.5 to 5 μM, preferably 1 to 3 μM, in this two-step protocol of the embodiment.

According to a fifth aspect of the invention there is provided a kit for use in stem cell differentiation to cardiomyocytes via casein kinase inhibition comprising a compound of the formula (I), (Ia), (Ia)' or (II), or a stereoisomer, tautomer, or a salt thereof, wherein $R^1$, $R^2$ and $R^3$ independently from another represent hydrogen, optionally substituted alkyl, alkenyl, alkynyl, heterocyclyl, heteroaryl or aryl; X represents $NR^4$, O or S; and $R^4$ represents hydrogen, optionally substituted alkyl, alkenyl, alkynyl, heterocyclyl, heteroaryl or aryl together with excipients. The compounds of formula (I), (Ia), (Ia)' and (II) can be formulated in compositions comprising as excipients diluents, solvents, which can be buffer solutions, or other aqueous and non-aqueous carriers.

One embodiment of the invention, provides a kit for use in stem cell differentiation to cardiomyocytes comprising a compound of formula (I) or (II), wherein $R^1$ represents halogen substituted monovalent and divalent, single, polynuclear, conjugated and fused residues of aromatic hydrocarbons having from 6 to 10 carbon atoms; $R^2$ represents halogen substituted aromatic hydrocarbons having 6 carbon atoms; $R^3$ represents saturated 5 to 6 ring membered heterocycloalkyl having 1 to 3 hetero atoms selected from N or O, or an aromatic radical having 5 to 6 ring atoms wherein 1 to 3 atoms are heteroatoms selected from O and N; and X represents NH, or a stereoisomer, tautomer, or a salt thereof together with excipients. Fluorine is preferred as halogen.

Another embodiment of the invention provides a kit for use in stem cell differentiation to cardiomyocytes comprising one of the above described individual compounds according to Formula's IIIa to IIIe, or a stereoisomer, tautomer, or a salt thereof together with excipients.

Additional excipients in the compositions may be adjuvants such as preservatives, wetting agents, emulsifying agents, and dispersing agents. Prevention of the action of micro-organisms may be ensured by the inclusion of various antibacterial and antifungal agents, for example, paraben, chlorobutanol, phenol sorbic acid, and the like. It may also be desirable to include isotonic agents such as sugars, sodium chloride, and the like. Prolonged usage ability of the composition may be brought about by the inclusion of agents that delay absorption such as aluminium monostearate and gelatin.

In such embodiment there is provided a kit comprising a container with a composition of the compound of the formula (I), (Ia), (Ia)' or (II), or a stereoisomer, tautomer, or a salt thereof, together with excipients. In such a kit or pack, a container having a unit dosage of the agent(s) may be found. The kits may include a composition comprising an effective agent either as concentrates, which may be diluted further prior to use or they can be provided at the concentration of use, where the vials may include one or more dosages. Conveniently, in the kits, single dosages can be provided in sterile vials and suitable sizes so that the scientist can employ the vials directly, where the vials will have the desired amount and concentration of agent(s). Vials with media, such as DMEM or RPMI with or without B27 supplements, can be part of the kit. Associated with such container(s) may be various written materials such as instructions for use. Such instructions for use can describe the use of the CK 1 inhibitors according to any of the inventive methods describes above. They can especially refer to an application of the CK1 inhibitor during 3 to 8 (or 4 to 8) of the differentiation or the late (post mesoderm) development of cardiomyocytes.

Most preferred is a kit which additionally comprises the compound CHIR99201. This kit can be used in the preferred embodiment of the inventive method mentioned above. Preferably CHIR99201 is added in a separate container in the kit, e.g. together with instructions when to apply it in relation to the CK 1 inhibitor. Preferably it describes a two step protocol of first applying the compound CHIR99201 and then applying the casein inhibitor of formula (I) or (II) during the late (post mesoderm) development of cardiomyocytes.

EXAMPLES

Example 1: Materials and Methods

In the examples described below, unless otherwise indicated, all temperatures in the following description are in degrees Celsius and all parts and percentages are by weight, unless indicated otherwise. Reagents useful for synthesizing compounds may be purchased from commercial suppliers, such as Sigma-Aldrich Pte Ltd, Life Technologies or others and used without further purification, unless otherwise indicated, or obtained or prepared according to techniques known in the art.

The identity of all compounds was assessed after purification by HRMS-ESI analyses on an Agilent 6200 series accurate-mass time-of-flight (TOF) LC/MS in electrospray ionization (ESI) positive mode.

All the 1D and 2D NMR experiments for $^1$H (400.13 MHz), nuclei were performed on a Bruker AVANCE-400 digital NMR spectrometer. NMR spectra are reported in ppm with reference to an internal tetramethylsilane standard (0.00 ppm for $^1$H) or solvent peak(s) of CDCl$_3$ (7.26 and 77.1 ppm) or CD$_3$OD (3.31 and 49.0 ppm), or DMSO-d$_6$ (2.50 and 39.5 ppm). Other NMR solvents were used as needed. When peak multiplicities are reported, the following abbreviations are used: s=singlet, d=doublet, t=triplet, q=quartet, m=multiplet, br=broadened, dd=doublet of doublets, dt=doublet of triplets, bs=broadened singlet. Coupling constants, when given, are reported in hertz.

LIST OF ABBREVIATIONS USED

| Names/terms | Abbreviations | Names/terms | Abbreviations |
| --- | --- | --- | --- |
| Acetate | OAc | Phenyl | Ph |
| Dimethyl sulfoxide | DMSO | Acetic acid | AcOH |
| Phosphate buffered saline | PBS | Nuclear Magnetic Resonance | NMR |
| Bovine serum albumine equivalent | BSA equiv | Ethyl Tetrahydrofuran | Et THF |
| High-performance liquid chromatography or high-pressure liquid chromatography | HPLC | Dichlormethane | DCM |
| high-resolution mass spectrometry | HRMS | Room temperature | rt |
| n-Butyllithium | $^n$BuLi | Lithium bis(trimethylsilyl)amide | LiHMDS |
| 1,3-Dimethyl-3,4,5,6-tetrahydro-2(1H)-pyrimidinone | DMPU | N-Bromosuccinimide | NBS |
| Dicyclohexyl(2',6'-diisopropoxy-2-biphenylyl)phosphine | RuPhos | Pivalic acid | PivOH |

Culture of HESCs hESC3 Nkx2.5$^{eGFP/w}$ (reporter cell line for cardiac differentiation kindly provided from David Elliot Lab. Melbourne Australia, see Nat Methods. 2011 Oct. 23; 8(12): 1037-40. doi: 10.1038/nmeth.1740, NKX2-5(eGFP/w) hESCs for isolation of human cardiac progenitors and cardiomyocytes, Elliott DA1, Braam S R, Koutsis K, Ng E S, Jenny R, Lagerqvist E L, Biben C, Hatzistavrou T, Hirst C E, Yu Q C, Skelton R J, Ward-van Oostwaard D, Lim S M, Khammy O, Li X, Hawes S M, Davis R P, Goulburn A L, Passier R, Prall O W, Haynes J M, Pouton C W, Kaye D M, Mummery C L, Elefanty A G, Stanley E G) was cultured on irradiated mouse embryonic fibroblasts derived from the progeny of 129X1/SvJ mice, in DMEM/F12 medium supplemented with 20% Knockout serum replacement (KSR), 1% nonessential amino acid solution, 50 U/ml penicillin, 50 µg/ml streptomycin, 2 mM L-glutamine, 0.1 mmol/L β-mercaptoethanol, and 10 ng/ml basic fibroblast growth factor, all procured from Life Technologies.

hESC7 (H7, see Science 6 Nov. 1998: Vol. 282 no. 5391 pp. 1145-1147; DOI: 10.1126/science.282.5391.1145; Report Embryonic Stem Cell Lines Derived from Human Blastocysts; James A. Thomson, Joseph Itskovitz-Eldor, Sander S. Shapiro, Michelle A. Waknitz, Jennifer J. Swiergiel, Vivienne S. Marshall, Jeffrey M. Jones) and hiPSC 00208 (derived in University of Tampere, kindly provided by Dr. Katriina Aalto-Setälä) were cultured on irradiated mouse embryonic fibroblasts derived from the progeny of 129X1/SvJ mice, in Knockout DMEM supplemented with 20% Knockout serum replacement (KSR), 1% nonessential amino acid solution, 50 U/ml penicillin, 50 µg/ml streptomycin, 2 mM L-glutamine, 0.1 mmol/L β-mercaptoethanol, and 100 ng/ml basic fibroblast growth factor, all procured from Life Technologies.

All media was refreshed daily and cultures were passaged every 4-5 days. Cultures were incubated at 37° C. in a humidified atmosphere with 5% CO$_2$.

Cardiomyocyte Differentiation and Analyses hESC and hiPSC were harvested in 100 µm clumps and seeded at 2.2×10$^6$ cells/well as EBs in ultra-low attachment 12-well plates (Nunc) in basic serum free stem cell (bSFS) medium: DMEM (Life Technologies) supplemented with 2 mM L-glutamine (Life Technologies), 0.182 mM sodium pyruvate (Life Technologies), 1% non-essential amino acids (Life Technologies), 0.1 mM 3-mercaptoethanol, 5.6 mg/L transferrin (Life Technologies), 20 µg/L sodium selenite (Sigma), 0.5% (w/vol) Bovine Serum Albumin (Life Technologies) and 0.25% (w/vol) Hysoy (Sheffield Bioscience). Cells were incubated for 24 h at 37° C. and 5% CO$_2$ to allow EB formation. The medium was refreshed thereafter and then every 2-3 days, cells were stimulated with the respective compounds (Table 1 and 2) in equal amounts of DMSO (1 µl DMSO/ml of media) (Sigma-Aldrich) at a specific time course.

EBs were harvested 11 days after differentiation induction and dissociated in a single suspension by incubation for 8-12 min in TrypLE (Invitrogen). Cell number and viability was evaluated with Nucleocount according to the manufacturer's protocol. The harvested single suspension cells were fixed and permeabilized (FIX&PERM, BD).

Cells were incubated with cardiac troponin T (dilution at 1:400, Pierce) and cardiac atrium antibody MLC2a (dilution 1:800, SYSY Synaptic Systems) antibodies for 30 min, and detected with an appropriate secondary antibody Alexa Fluor 647 (1:500, Life Technology) on flow cytometer Guava (Millipore) using Flowjo software.

Cyto-immunofluorescence was performed on 16 days old embryoid bodies (EBs). EBs were transferred on day 6 onto attachment plates to allow cells to grow out onto objective material. EBs and cells were fixed with 4% paraformaldehyde for 30 minutes at room temperature. Cells were incubated with cardiac troponin T (dilution at 1:200, Pierce), sarcomeric actinin (dilution at 1:200, Sigma-Aldrich), cardiac atrium antibody MLC2a (dilution 1:400, SYSY Synaptic Systems), and muscle mesoderm marker MEF2C (dilution 1:200, Cell Signaling) antibodies in 3% BSA-PBS with 0.2% Triton-X overnight. Appropriate secondary antibody Alexa Fluor 488 and 594 (1:500; Life Technologies) were used to detect the signal with an Olympus fluorescence microscope. Nuclear stains for cell detection were DAPI (R&D) and DracQ (Cell Signaling). Multilayer fluorescence images were combined with Image J.

Detailed Cardiomyocyte Differentiation Protocol and Flow Cytometer Analyses

Preparations: Stem cells were expanded on 10 centimeter culture dishes for 5-6 days to 80-90% confluence prior experiment. One standard culture dish provides enough material (approx. $28 \times 10^6$ cells) for one 12-well plate experiment.

1. Wash stem cells with PBS×1 (without Mg and Ca)
2. Submerge with PBS×1 (without Mg and Ca)
3. Remove feeder and non-colony like (differentiated) stem cells by aspirating with a sharp tip (20 μm tip)
4. Submerge in basic serum free stem cell differentiation media (bSFS) (6-8 ml)
5. Use a passaging tool (EZ passaging tool, Life Technology) for stem cells to cut in vertical and horizontal directions to obtain cell cluster squares of similar dimensions of about 50-100 μm
6. Separate floating clusters meshes very carefully to minimize cell death by pipetting up and down with a serological pipette.
7. Leave stem cells clusters to sediment in petri dish for 5-10 min
8. Aspirate at least ⅔ of the volume to remove floating feeder cells and single stem cells, but not the stem cell clusters
9. Add 20 ml bSFS medium
10. Estimate viability and cell number
11. Seed between $2.2-2.5 \times 10^6$ cells/well (total cell count with minimum viability 75%) in ultralow attachment 12-well plates.
12. Adjust total volume per well to 2 ml. (Minimum media per well is 1.5 ml maximal 3 ml.)
13. Optional for high efficiency differentiation: Add CHIR99021 diluted in DMSO per well at 3 μM for hESC3, 4 μM for hESC7 and 2-3 μM for hiPSC for 24 h.
14. Disperse stem cell clumps evenly over the surface (don't let them cluster in the middle)
15. Place cell culture for overnight or 24 h under culture condition
16. Change bSFS medium (2-3 ml) and remove all small cluster below 150 micron as much as possible
17. Optional differentiation protocol for days 1-8 or 1-3: Add compounds dissolved in DMSO at 1 μl/ml at desired μM concentration (Table 1 and 2) to the cultures and mix well.
18. Disperse embryoid bodies evenly over the surface and leave cell culture for further 3 days under culture condition
19. Change bSFS medium (2-3 ml) and add compounds dissolved in DMSO at 1 μl/ml at desired μM concentration (Table 1 and 2) to the cultures
20. Refresh bSFS media with compounds every 2 days for the next 4 days
21. Refresh only bSFS media (3 ml) and culture for 3 more days
22. Analyze embryoid bodies (beat count, beat frequency, flow cytometry, cyto-immunofluorescence and cell count)

Evaluation of Cardiomyocyte Differentiation with Flow Cytometer

1. Transfer all embryoid bodies (EBs) from 12 well plates to a 1.5 ml Eppendorf tube on day 11/12 of experiment.
2. Spin cells down at 13000 rpm for 30 sec and aspirate supernatant
3. Wash cells once with PBS−/− (without calcium and magnesium)
4. Spin cells down at 13000 rpm for 30 sec and aspirate supernatant
5. Digest cells with 500 μL TrypLE (Life Technology)
6. Incubate at 37° C. water bath with shaking (tapping the eppendorf tube from time to time) for 8 min (max 15 min).
7. Add 500 μl culture medium to stop the digestion and pipette up and down to break down cell clusters to an homogeneous suspension
    a. Optional: Cell count
    b. Aliquot 95 μl to a new eppendorf tube
    c. Add 5 μl of solution 13 (Nucleocount) and mix well
    d. Load 10 μl of the solution into the glass probe
    e. Preform the read out (assay: single cell and viability) with Nucleocounter
8. Repeat washing step 2-4
9. Strain cells through a 20-40 um nylon mesh or mesh plate to remove cell clumps
    a. Optional: Fixation and cyto-immunofluorescence (cTnT and MLC2a)
    b. Fix cells with 100 μL BD cytofix/cytoperm (BD kit) for 20 min on ice
    c. Wash cell twice with 1× Perm/Wash buffer (BD kit)
    d. Resuspend cells in flow buffer (PBS 1% bovine serum albumin) with cTnT antibody 1:400 or MLC2a 1:800
    e. Incubate on ice in dark for 30 min
    f. Add 100 μL flow buffer and spin down at 13000 rpm for 30 sec
    g. Wash cells once again with flow buffer
    h. Resuspend cells with flow buffer with second antibody (Alexa Fluor-647 goat anti-mouse IgG1, 1:500)
    i. Incubate on ice in dark for 20 min
    j. Add 100 μL flow buffer and spin down at 13000 rpm for 30 sec
    k. Wash cells once again with flow buffer
10. Resuspend not more than 200,000 cells/ml in flow buffer (PBS 1% bovine serum albumin)
11. Transfer 250 μl in 96-well U-bottom plates (Greiner)

12. Preform read out fluorescence with the flow cytometer (Guava, Millipore)

Functional Assay of Developed Cardiomyocytes

Microscopic videos from the culture wells were captured via a camera mounted on a Nikon Eclipse Ti microscope platform and later analyzed to objectively identify and quantify beating aggregates in terms of frequency, amplitude, size, etc. In order to maintain cultures for long term, cultures on the platform were kept at 37° C. with 5% $CO_2$ via an on-stage incubator.

Alternative High Efficiency Cardiomyocyte Differentiation Methods (FIGS. 9 to 11)

Culture of HESCs for the Alternative Cardiomyocyte Differentiation Methods

Human embryonic stem cell (hESC) lines HES-3 (NKS2.5$^{eGFP/w}$ reporter cell line for cardiac differentiation kindly provided from David Elliot Lab. Melbourne Australia) and H7, as well as human induced pluripotent stem cell (IPS) lines IMR-90, Donor 11 (in-house IPS cell line) and IPS00208 (derived in University of Tampere, kindly provided by Dr. Katriina Aalto-Setil) were cultured on Geltrex® coated (Gletrex, Life Technologies) in E8 medium (Life technologies). All media was refreshed daily and cultures were passaged every 4-5 days. Cultures were incubated at 37° C. in a humidified atmosphere with 5% $CO_2$. Plates with a 50-70% confluence were used for experiments.

Differentiation in 96-U Bottom Ultra-Low Attachment Well Plates (FIG. 9)

Human embryonic stem cell (hESC) lines HES-3 (NKS2.5$^{eGFP/w}$ reporter cell line for cardiac differentiation kindly provided from David Elliot Lab. Melbourne Australia) were dissociated with TrypLE (Invitrogen) and seeded at $1.5 \times 10^4$ cells/well in ultra-low attachment 12-well plates (Nunc) in bSFS medium: DMEM or RPMI (Life Technologies) supplemented with 2 mM L-glutamine (Life Technologies), 0.182 mM sodium pyruvate (Life Technologies), 1% non-essential amino acids (Life Technologies), 0.1 mM β-mercaptoethanol, 5.6 mg/L transferrin (Life Technologies), 20 µg/L sodium selenite (Sigma), 0.5% (w/vol) Bovine Serum Albumin (Life Technologies) and 0.25% (w/vol) Hysoy (Sheffield Bioscience). Cells were sun down at 400 rpm to form an EB and incubated for 24 h with 6 µM CHIRR99021 (Selleck, US), 7.5 µM Y27632 (Selleck, US) and 50 µg/ml Matrigel® (BD, UK) at 37° C. and 5% $CO_2$ to allow EB formation. The medium was refreshed thereafter and the CHIR99021 concentration was lowered to 1.5 µM. 24 h later the cells were supplied with fresh bSFS medium. On day 2 or 3 EBs were stimulated with the respective inhibitor compounds (Table 1) in equal amounts of DMSO (1 µl DMSO/ml of media) (Sigma-Aldrich) for 5 days.

On day 14 Microscopic images of each EB were captured via a camera mounted on a Nikon Eclipse Ti microscope platform in phase contrast mode and with fluorescence imaging. Images were analyzed to objectively identify and quantify green florescence areas, and embryoid body size with Image J®. The cultures on the platform were kept at 37° C. with 5% $CO_2$ via an on-stage incubator.

Differentiation in 12-Well Ultra-Low Attachment Plates (FIG. 10)

hESC (H7) and IPS (Donor 11, IMR-90) were harvested in 100 µm clumps and seeded at $2.2 \times 10^6$ cells/well as EBs in ultra-low attachment 12-well plates (Nunc) in bSFS medium: DMEM (Life Technologies) supplemented with 2 mM L-glutamine (Life Technologies), 0.182 mM sodium pyruvate (Life Technologies), 1% non-essential amino acids (Life Technologies), 0.1 mM β-mercaptoethanol, 5.6 mg/L transferrin (Life Technologies), 20 g/L sodium selenite (Sigma), 0.5% (w/vol) Bovine Serum Albumin (Life Technologies) and 0.25% (w/vol) Hysoy (Sheffield Bioscience). Cells were incubated for 24 h with 6 µM CHIRR99021 (Shelleck, US) at 37° C. and 5% $CO_2$ to allow EB formation. The medium was refreshed thereafter and the CHIR99021 concentration was lower to 1.5 µM. 24 h later we supplied the cells with fresh bSFS medium, cells were stimulated with the respective TA compounds in equal amounts of DMSO (11 DMSO/ml of media) (Sigma-Aldrich) for 6 days.

EBs were harvested 14 days after differentiation induction and dissociated in a single suspension by incubation for 8-12 min in TrypLE (Invitrogen). Cell number and viability was evaluated with Nucleocount according to the manufacturer's protocol. The harvested single suspension cells were fixed and permeabilized (FIX&PERM, BD).

Cells were incubated with cardiac Troponin T (dilution at 1:400, Pierce) and cardiac atrium antibody MLC2a (dilution 1:800, SYSY Synaptic Systems) antibodies for 30 min, and detected with an appropriate secondary antibody Alexa fluor 647 (1:500, Life Technology) on flow cytometer Guava (Millipore) using Flowjo software.

Differentiation on Microcarriers (FIG. 11)

HES-3 were seeded at $2 \times 10^5$ cells/ml in the 50 ml spinner flask that contained 25 ml hESC medium and 200 mg PLL+LN-coated MC (poly-L-lysine and laminin coated microcarrier). The sample was incubated at 37° C./5% carbon dioxide for 24 hours in static conditions, after which another 25 ml hESC medium were added and the culture was then agitated at 30 rpm for 6 days. Eighty percent of the spent medium was replaced daily with fresh hESC medium. The cell concentration and cell viability were determined daily using a Nucleocounter NC-3000 (Chemometec, Davis, Calif., USA). Pluripotent markers were measured by flow cytometry on day 7. The size of the hESC/MC aggregates was measured from images taken using an Olympus IX70 microscope (Olympus, Shinjuku-ku, Tokoyo, Japan), with average dimensions determined using NIH image J software.

About 50 hESC/MC aggregates from spinner cultures were incubated in a 12-well ultra-low attachment plate (Nunc, Rochester, N.Y., USA) and directly subjected to cardiac differentiation simply by changing the hESC medium into 15 µM CHIRR99021 containing DMEM or RPMI with B27 supplements based differentiation medium. After 24 hours the differentiation medium was replenished, and 5 µM IWP-2 or TA-01 was added at day 3. This IWP-2 and TA-01 was removed during the medium exchange on day 5. Cells were then maintained in differentiation medium with insulin from day 11 until day 20 followed by IWP-2, TA-01 treatment. On day 20 of the differentiation protocol, cells from all cultures were harvested and analyzed by fluorescence-activated cell sorting (FACS) for cardiac markers MLC2a and Tropoin T (cTnt) and MF20.

Example 2: Synthesis of Compounds

The target compounds were synthesized using routes outlined in FIGS. 1 to 5. All of the synthesized imidazoles with unsubstituted N1 nitrogen were obtained as a mixture of annular tautomers which rapidly interconvert in solution. For compounds containing a chiral centre, they were synthesized as a racemic mixture of stereoisomers and applied in the biological studies as a racemic mixture. Details of the synthesis of the compounds are as follows:

All of the synthesized compounds (except IM-44) possess the 2,4,5-tri-substitution pattern on the azole core structure and can be classified according to the general structures shown in FIG. 1.

Compounds 1a-1c and other compounds containing the vicinal pyridin-4-yl/4-fluorophenyl moiety similar to SB203580 were synthesized according to FIG. 2. Sonogashira coupling between 4-fluorophenylacetylene 6 and 4-bromopyridine 7 gave 1,2-disubstituted alkyne 8 which was oxidized to 1,2-diketone 9 using potassium permanganate under slightly basic conditions. Diketone 9 was then condensed with the appropriate aldehydes and ammonium acetate under acidic conditions to give imidazoles 1a-1c. Diketone 9 was also condensed with the appropriate aldehydes and ammonium acetate under acidic conditions to give imidazoles ZQX-14-23 and ZQX-25-32.

The synthesis of compounds 2a-2e containing the vicinal pyridin-4-yl/3-tolyl moiety had been reported in Low, J. L. et al. Bioorg Med Chem Lett 2013, 23, 3300. Other compounds containing the vicinal pyridin-4-yl/3-tolyl moiety (2f-2t) were synthesized as shown in FIG. 3. Imidazoles 2f-2h and 2t were obtained through the condensation reaction of 1,2-diketone 10a and 10b respectively with the various aldehydes and ammonium acetate in acetic acid. Condensation of 1,2-diketone 10a with 4-formylbenzonitrile gave 2i following which reaction with hydroxylamine in refluxing ethanol gave 2j. Compound 2k was obtained through condensation of 1,2-diketone 10a with 4-formylbenzoic acid. Reaction of 2k with thionyl chloride generates the acid chloride which was then reacted with aqueous ammonia and methanol to give amide 2l and ester 2m respectively. Imidazole 2o was obtained through the condensation of 4-nitrobenzaldehyde with 1,2-diketone 10a to give 2n, followed by reduction using palladium on carbon.

For imidazoles containing non-aromatic substituents at the C-2 position 1,2-diketone 10a was first reacted with formaldehyde and ammonium acetate in acetic acid under microwave conditions to give 4,5-disubstituted imidazole 2p. Heating 2p with formaldehyde and dimethyl amine in ethanol resulted in 2q. Iodination of 2p at the imidazole C-2 position with N-iodosuccinimide gave compound 11 following which Sonogashira coupling with 3-butyn-1-ol gave 2r. Compound 2s was synthesized by first protecting the imidazole N-1 nitrogen of 2p with trityl chloride to give compound 12 followed by nucleophilic addition to 1-cyclohexene-1-carbaldehyde to give compound 13. Subsequent trityl deprotection of compound 13 gave compound 2s.

With regards to the compounds containing a pyran-4-yl substituent at the imidazole C-5 position, they were synthesized according to FIG. 4. The preparation of imidazoles 3a and 4a had been reported in Low, J. L. et al. Bioorg Med Chem Lett 2013, 23, 3300, and they were not included in the scheme. Compounds 3b-3e and 3f were synthesized via condensation of 1,2-diketone 14a and 14b respectively with the appropriate aldehydes and ammonium acetate in acetic acid. Similarly compounds 4b-4k were obtained by reacting 1,2-diketone 15 with the respective aldehydes and ammonium acetate in acetic acid.

Oxazoles OZ-06 and OZ-12 were synthesized via the sequence shown in FIG. 5. The first step involved a regioselective C4 bromination of 5-substituted oxazoles 16a and 16b to give 4,5-disubstituted oxazoles 17a and 17b. A Suzuki cross-coupling reaction then installs the desired aryl group at the C4 position of oxazoles 17a and 17b to give 4,5-diaryl oxazoles 18a and 18b which then underwent direct arylation at the oxazole C2 position to give 2,4,5-triaryl oxazoles 19a and 19b. The thiomethyl group of oxazole 19a and 19b was then oxidized to the methyl sulfoxide group in oxazoles OZ-06 (5a) and OZ-12 (5b) respectively using potassium persulfate under acidic conditions.

General Procedures for the Synthesis of 2,4,5-Trisubstituted Imidazoles.

Unless otherwise stated, the procedures for the synthesis of the 2,4,5-trisubstituted imidazoles are as follows:

Method A

To a solution of the 1,2-dione (1 equiv) in glacial acetic acid was added $NH_4OAc$ (10 equiv) followed by aldehyde (1.1-1.3 equiv). The reaction mixture was then heated to 115° C. in an oil bath and left to stir overnight. After the reaction was cooled to room temperature, the pH of the reaction mixture was adjusted to 8 with saturated $NaHCO_3$ solution and solid $NaHCO_3$ and extracted with ethyl acetate. The organic extracts were dried over anhydrous $Na_2SO_4$, filtered and the solvent was removed in vacuo to give the crude product which was purified by silica gel chromatography to afford the final product.

Method B

To a solution of the 1,2-dione (1 equiv) in glacial acetic acid was added $NH_4OAc$ (10 equiv), aldehyde (1.1-1.3 equiv) and $Cu(OAc)_2 \cdot H_2O$ (0.3-2.0 equiv). The reaction mixture was then heated to 80° C. in an oil bath and left to stir overnight. After the reaction was cooled to room temperature, the pH of the reaction mixture was adjusted to 8 with saturated $NaHCO_3$ solution and solid $NaHCO_3$ and extracted with ethyl acetate. The organic extracts were dried over anhydrous $Na_2SO_4$, filtered and the solvent was removed in vacuo to give the crude product which was purified by silica gel chromatography to afford the final product.

The following compounds have been synthesized accordingly:

4-(2-(2,6-difluorophenyl)-4(5)-(4-fluorophenyl)-1H-imidazol-5(4)-yl)pyridine (1a, IM-31, TA-01)

Synthesized according to general procedure A using 9 and 2,6-difluorobenzaldehyde. 1a was obtained as a white solid in 97% yield (74 mg). $^1$H NMR (400 MHz, $CD_3OD/DMSO$-$d_6$ 3:1): δ=8.51 (d, J=6.1 Hz, 2H), 7.66-7.56 (m, 5H), 7.31-7.23 (m, 4H); HRMS-ESI m/z [M+H]$^+$ calcd for $C_{20}H_{13}F_3N_3$: 352.1056, found: 352.1065.

4-(2-(2-fluorophenyl)-4(5)-(4-fluorophenyl)-1H-imidazol-5(4)-yl)pyridine (1b, IM-30, TA-02)

Synthesized according to general procedure A using 9 and 2-fluorobenzaldehyde. 1b was obtained as an off-white solid in 68% yield (36 mg). $^1$H NMR (400 MHz, $CD_3OD/DMSO$-$d_6$ 4:1): δ=8.48 (d, J=4.4 Hz, 2H), 8.06 (td, J=7.6, 1.5 Hz, 1H), 7.60-7.57 (m, 4H), 7.55-7.51 (m, 1H), 7.40-7.32 (m, 2H), 7.26 (t, J=8.7 Hz, 2H); HRMS-ESI m/z [M+H]$^+$ calcd for $C_{20}H_{14}F_2N_3$: 334.1150, found: 334.1156.

4-(2-(1-fluoronaphthalen-2-yl)-4(5)-(4-fluorophenyl)-1H-imidazol-5(4)-yl)pyridine (1c, IM-29)

Synthesized according to general procedure A using 9 and 1-fluoro-2-naphthaldehyde. 1c was obtained as an off-white solid in 56% yield (50 mg). $^1$H NMR (400 MHz, DMSO-$d_6$/$CD_3OD$ 4:1): δ=8.50 (d, J=5.7 Hz, 2H), 8.18-8.12 (m, 2H), 8.03 (d, J=8.0 Hz, 1H), 7.88 (d, J=8.7 Hz, 1H), 7.71-7.64 (m, 2H), 7.60 (dd, J=8.8, 5.5 Hz, 2H), 7.50 (dd, J=4.6, 1.6 Hz, 2H), 7.30 (t, J=8.7 Hz, 2H); HRMS-ESI m/z [M+H]$^+$ calcd for $C_{24}H_{16}F_2N_3$: 384.1307, found: 384.1313.

4-(2-(naphthalen-2-yl)-4(5)-(m-tolyl)-1H-imidazol-5(4)-yl)pyridine (2f, IM-01)

Synthesized according to general procedure B using 10a and 2-naphthaldehyde. 2f was obtained as a pale yellow solid in 49% yield (39 mg). $^1$H NMR (400 MHz, DMSO-d$_6$): δ=13.08 (s, 1H), 8.63 (s, 1H), 8.48 (s, 2H), 8.26 (dd, J=8.6, 1.7 Hz, 1H), 8.03 (d, J=8.7 Hz, 1H), 8.00-7.90 (m, 2H), 7.62-7.50 (m, 4H), 7.49-7.21 (m, 4H), 2.38 (s, 3H); HRMS-ESI m/z [M+H]$^+$ calcd for $C_{25}H_{20}N_3$: 362.16517, found: 362.16574.

4-(2-(4-(methylsulfonyl)phenyl)-4(5)-(m-tolyl)-1H-imidazol-5(4)-yl)pyridine (2g, IM-33)

Synthesized according to general procedure A using 10a and 4-(methylsulfonyl)benzaldehyde. 2g was obtained as a light-yellow solid in 45% yield (43 mg). $^1$H NMR (400 MHz, CD$_3$OD): δ=8.40 (s, 2H), 8.23 (d, J=8 Hz, 2H), 8.04 (d, J=8 Hz, 2H), 7.58 (d, J=4 Hz, 2H), 7.35-7.27 (m, 3H), 3.17 (s, 3H), 2.37 (s, 3H); HRMS-ESI m/z [M+H]$^+$ calcd for $C_{22}H_{20}N_3O_2S$: 390.1271, found: 390.1269.

N-(4-(5(4)-(pyridin-4-yl)-4(5)-(m-tolyl)-1H-imidazol-2-yl)phenyl)methanesulfonamide (2h, IM-35)

Synthesized according to general procedure A using 10a and N-(4-formylphenyl)methanesulfonamide. 2h was obtained as a yellow solid in 52% yield (76.8 mg). $^1$H NMR (400 MHz, DMSO-d$_6$): δ=12.83 (s, br, 1H), 9.98 (s, br, 1H), 8.54-8.44 (m, 2H), 8.03 (d, J=8.1 Hz, 2H), 7.49 (s, 2H), 7.38 (s, 2H), 7.31-7.29 (m, 4H), 3.06 (s, 3H), 2.37 (s, 3H); HRMS-ESI m/z [M+H]$^+$ calcd for $C_{22}H_{21}N_4O_2S$: 405.1380, found: 405.1383.

4-(5(4)-(pyridin-4-yl)-4(5)-(m-tolyl)-1H-imidazol-2-yl)benzonitrile (2i, IM-36)

Synthesized according to general procedure A using 10a and 4-formylbenzonitrile. 2i was obtained as a white solid in 80% yield (62 mg). $^1$H NMR (400 MHz, CD$_3$OD): δ=8.44 (d, J=4 Hz, 2H), 8.19 (d, J=8 Hz, 2H), 7.85 (d, J=8 Hz, 2H), 7.60 (d, J=4 Hz, 2H), 7.38-7.29 (m, 4H), 2.39 (s, 3H); HRMS-ESI m/z [M+H]$^+$ calcd for $C_{22}H_{17}N_4$: 337.1448, found: 337.1458.

(Z)—N'-hydroxy-4-(5(4)-(pyridin-4-yl)-4(5)-(m-tolyl)-1H-imidazol-2-yl)benzimidamide (2j, IM-37)

To a solution of 2i (40 mg, 0.12 mmol, 1 equiv) in ethanol (10 mL) was added hydroxylamine hydrochloride (26 mg, 0.37 mmol, 3 equiv) and triethylamine (37 mg, 0.37 mmol, 3 equiv). The reaction mixture was heated to reflux at 95° C. and left to stir overnight. The solvent was removed in vacuo to give the crude product which was purified by silica gel column chromatography (petroleum ether/ethyl acetate/methanol 20:20:1) to afford 2j as a light yellow solid in 61% yield (42 mg). $^1$H NMR (400 MHz, CD$_3$OD): δ=8.41 (s, 2H), 8.04 (d, J=8 Hz, 2H), 7.78 (d, J=8 Hz, 2H), 7.57 (d, J=4 Hz, 2H), 7.36-7.26 (m, 4H), 2.38 (s, 3H); HRMS-ESI m/z [M+H]$^+$ calcd for $C_{22}H_{20}N_5O$: 370.1662, found: 370.1665.

4-(5(4)-(pyridin-4-yl)-4(5)-(m-tolyl)-1H-imidazol-2-yl)benzoic acid (2k, IM-38)

Synthesized according to general procedure A using 10a and 4-formylbenzoic acid. 2k was obtained as a light yellow solid in 45% yield (222 mg). $^1$H NMR (400 MHz, CD$_3$OD): δ=8.42 (s, J=4 Hz, 2H), 8.07 (d, J=8 Hz, 2H), 8.01 (d, J=8 Hz, 2H), 7.59 (d, J=4 Hz, 2H), 7.38-7.26 (m, 4H), 2.39 (s, 3H); HRMS-ESI m/z [M+H]$^+$ calcd for $C_{22}H_{18}N_3O_2$: 356.1394, found: 356.1399.

4-(5(4)-(pyridin-4-yl)-4(5)-(m-tolyl)-1H-imidazol-2-yl)benzamide (2l, IM-39)

Compound 2k (36.5 mg, 0.10 mmol, 1 equiv) was dissolved in thionyl chloride (8 mL) and the reaction mixture was heated up to 80° C. and stirred for 3 h. Thionyl chloride was removed in vacuo, the resulting residue was dissolved in dichloromethane (5 mL) and added dropwise to (28-30%) ammonium hydroxide solution (10 mL) at 0° C. and stirred for 30 min during which the product precipitates out of solution. The crude product was collected by filtration and purification by silica gel column chromatography (dichloromethane/methanol 40:1) afforded 2l as a yellow solid in 72% yield (25.5 mg). $^1$H NMR (400 MHz, DMSO-d$_6$): δ=13.08 (s, br, 1H), 8.48 (s, 2H), 8.17 (d, J=8 Hz, 2H), 8.04 (s, 1H), 7.99 (d, J=8 Hz, 2H), 7.52 (d, J=4 Hz, 2H), 7.41-7.27 (m, 5H), 2.36 (s, 3H); HRMS-ESI m/z [M+H]$^+$ calcd for $C_{22}H_{19}N_4O$: 355.1553, found: 355.1554.

Methyl 4-(5(4)-(pyridin-4-yl)-4(5)-(m-tolyl)-1H-imidazol-2-yl)benzoate (2m, IM-40)

Compound 2k (40 mg, 0.11 mmol, 1 equiv) was dissolved in thionyl chloride (8 mL) and the reaction mixture was then heated up to 80° C. and stirred for 3 h. Thionyl chloride was removed in vacuo and the resulting residue was dissolved in methanol (5 mL) and stirred for 30 min at room temperature. Removal of solvent afforded the crude product which was purified by silica gel column chromatography (dichloromethane/methanol 20:1) afforded 2m as a yellow solid in 74% yield (30 mg). $^1$H NMR (400 MHz, DMSO-d$_6$): δ=8.48 (s, 2H), 8.23 (d, J=8 Hz, 2H), 8.07 (d, J=8 Hz, 2H), 7.52 (d, J=4 Hz, 2H), 7.41-7.31 (m, 4H), 3.88 (s, 3H), 2.36 (s, 3H); HRMS-ESI m/z [M+H]$^+$ calcd for $C_{23}H_{20}N_3O_2$: 370.1550, found: 370.1552.

4-(2-(4-nitrophenyl)-4(5)-(m-tolyl)-1H-imidazol-5(4)-yl)pyridine (2n, IM-32)

Synthesized according to general procedure A using 10a and 4-nitrobenzaldehyde. 2n was obtained as a light yellow solid in 40% yield (35 mg). $^1$H NMR (400 MHz, DMSO-d$_6$): δ=8.49 (s, 2H), 8.38-8.33 (m, 4H), 7.53 (s, 2H), 7.42-7.33 (m, 4H), 2.38 (s, 3H); HRMS-ESI m/z [M+H]$^+$ calcd for $C_{21}H_{17}N_4O_2$: 357.1346, found: 357.1347.

4-(5(4)-(pyridin-4-yl)-4(5)-(m-tolyl)-1H-imidazol-2-yl)aniline (2o, IM-34)

To a solution of 2n (21 mg, 0.06 mmol, 1 equiv) in methanol was added 10% palladium on carbon (3.2 mg, 0.003 mmol, 0.05 equiv). Hydrogen gas was introduced into the solution via a balloon and the reaction mixture was stirred at room temperature for 12 h. The reaction mixture was filtered over celite and methanol was removed in vacuo to give the crude product. Purification by silica gel column chromatography (petroleum ether/ethyl acetate 1:5) afforded 2o as a yellow solid in 55% yield (10.8 mg). $^1$H NMR (400 MHz, CD$_3$OD): δ=8.39 (s, 2H), 7.74 (d, J=8 Hz, 2H), 7.54

(d, J=4 Hz, 2H), 7.34-7.23 (m, 4H), 6.78 (d, J=8 Hz, 2H), 2.37 (s, 3H); HRMS-ESI m/z [M+H]+ calcd for $C_{21}H_{19}N_4$: 327.1604, found: 327.1604.

4-(4(5)-(m-tolyl)-1H-imidazol-5(4)-yl)pyridine (2p, IM-44)

Compound 10a (68 mg, 0.30 mmol, 1 equiv), 37% formaldehyde solution (25 µL, 0.33 mmol, 1.1 equiv), $NH_4OAc$ (231 mg, 3.0 mmol, 10 equiv) and glacial acetic acid (1.5 mL) were combined in a microwave reaction vial and sealed. The reaction mixture was then heated in a microwave reactor for 6 min at 180° C. After cooling, the reaction mixture was added dropwise to concentrated ammonium hydroxide solution at 0° C. The yellow precipitate obtained was collected by filtration, washed with water, and dried to afford 2p in 44% yield (31 mg) which was used without further purification. $^1$H NMR (400 MHz, $CD_3OD$): δ=8.40 (d, J=6.4 Hz, 2H), 7.85 (s, 1H), 7.50 (d, J=5.6 Hz, 2H), 7.32-7.22 (m, 4H), 2.36 (s, 3H); HRMS-ESI m/z [M+H]+ calcd for $C_{15}H_{14}N_3$: 236.1182, found: 236.1190.

N,N-dimethyl-1-(5(4)-(pyridin-4-yl)-4(5)-(m-tolyl)-1H-imidazol-2-yl)methanamine (2q, IM-42)

To a solution of 2p (52 mg, 0.22 mmol, 1 equiv) in ethanol was added 37% formaldehyde solution (19 µL, 0.26 mmol, 1.2 equiv) and dimethylamine (29 mg, 0.89 mmol, 1.2 equiv). The reaction mixture was heated up to 70° C. and stirred for 15 h. After cooling down to room temperature the solvent was removed in vacuo to give the crude product. Purification by silica gel column chromatography (dichloromethane/methanol 10:1) afforded 2q as a light yellow solid in 64% yield (41 mg). $^1$H NMR (400 MHz, $CD_3OD$): δ=8.40 (s, 2H), 7.50 (s, 2H), 7.33-7.21 (m, 4H), 3.67 (s, 3H), 2.38 (s, 6H), 2.35 (s, 3H); HRMS-ESI m/z [M+H]+ calcd for $C_{18}H_{21}N_4$: 293.1761, found: 293.1761.

4-(5(4)-(pyridin-4-yl)-4(5)-(m-tolyl)-1H-imidazol-2-yl)but-3-yn-1-ol (2r, IM-41)

Compound 2p (180 mg, 0.77 mmol, 1 equiv) was dissolved in THF (5 mL) followed by the addition of N-iodosuccinimide (207 mg, 0.92 mmol, 1.2 equiv) in two portions at 30 min intervals. The solution was allowed to stir at room temperature for another 3 h in darkness. Upon completion, the reaction mixture was quenched with saturated $Na_2S_2O_3$ solution and extracted with ethyl acetate. The organic layer was washed with brine, dried over anhydrous $Na_2SO_4$ and filtered. Removal of the solvent in vacuo afforded the crude product which was purified by silica gel column chromatography (dichloromethane/methanol 10:1) to afford 11 as a yellow solid in 80% yield (226 mg).

Dry triethylamine (1.7 mL) was first degassed by bubbling $N_2$ through the solution for 15 min. To this was added 11 (47 mg, 0.13 mmol, 1.0 equiv), $Pd(PPh_3)_4$ (7.5 mg, 0.0065 mmol, 0.05 equiv), CuI (2.5 mg, 0.013 mmol, 0.1 equiv), and 3-butyn-1-ol (11 mg, 0.16 mmol, 1.2 equiv) in this order under $N_2$. The solution was then stirred at room temperature for 6 h. Upon reaction completion, triethylamine was removed in vacuo and the residue obtained was dissolved in ethyl acetate and filtered through celite. The filtrate was washed with brine and the organic extracts were dried over anhydrous $Na_2SO_4$ and filtered. Removal of the solvent in vacuo afforded the crude product which was purified by silica gel column chromatography (dichloromethane/methanol 100:5) to afford 2r as a yellow oil in 37% yield (15 mg). $^1$H NMR (400 MHz, $CD_3OD$): δ=8.58 (d, J=4 Hz, 2H), 8.03 (d, J=8 Hz, 2H), 7.45-7.36 (m, 3H), 7.31 (d, J=7.3 Hz, 1H), 3.78 (t, J=8 Hz, 2H), 2.71 (t, J=8 Hz, 2H), 2.41 (s, 3H); HRMS-ESI m/z [M+H]+ calcd for $C_{19}H_{18}N_3O$: 304.1444, found: 304.1444.

Cyclohex-1-en-1-yl(5(4)-(pyridin-4-yl)-4(5)-(m-tolyl)-1H-imidazol-2-yl)methanol (2s, IM-43)

To a solution of 2p (50 mg, 0.21 mmol, 1 equiv) in dichloromethane (5 mL) was added triethylamine (43 mg, 0.42 mmol, 2 equiv) and triphenylmethyl chloride (59 mg, 0.21 mmol, 1 equiv). The reaction mixture was allowed to stir at room temperature for 12 h. Upon completion water was added to quench the reaction and extracted with dichloromethane. The combined organic extracts were washed with brine and dried over anhydrous $Na_2SO_4$. After filtration, the solvent was removed in vacuo to give the crude product. Purification by silica gel column chromatography (dichloromethane/methanol 20:1) afforded 12 as a white solid in 85% yield (86 mg).

To a solution of 12 (40 mg, 0.084 mmol, 1 equiv) in anhydrous THF was added a solution of n-BuLi (1.15M in hexanes, 100 uL, 0.12 mmol, 1.2 equiv) at 0° C. under $N_2$. The reaction mixture was allowed to warm up to room temperature and stirred for 30 min after which it was cooled down again to 0° C. and 1-cyclohexene-1-carboxaldehyde (11 mg, 0.1 mmol, 1.2 equiv) was added. The reaction mixture was allowed to warm up to room temperature again and stirred for another 6 h. Upon completion, the reaction mixture was diluted with ethyl acetate and washed with brine. Removal of the solvent in vacuo gave the crude product which was purified by silica gel column chromatography (dichloromethane/methanol 20:1) to afford 13 as a pale yellow oil containing a 1.4:1 mixture of atropisomers in 60% combined yield (29 mg).

To a solution of 13 (40 mg, 0.07 mmol, 1 equiv) in THF (2 mL) was added trifluoroacetic acid (23 mg, 0.2 mmol, 3 equiv) and deionized water (8 mg, 0.42 mmol, 6 equiv). The reaction mixture was allowed to stir at room temperature overnight. The reaction mixture was then diluted with ethyl acetate and washed with brine. Removal of the solvent in vacuo gave the crude product which was purified by silica gel column chromatography (dichloromethane/methanol 60:1) to afford 2s as a pale yellow oil in 80% yield (19 mg). $^1$H NMR (400 MHz, $CDCl_3$): δ=8.46 (d, J=4.8 Hz, 2H), 7.49 (d, J=4.4 Hz, 2H), 7.32-7.20 (m, 4H), 5.95 (s, 1H), 5.28 (s, 1H), 2.37 (s, 3H), 2.17 (s, 4H), 1.91-1.57 (m, 4H) HRMS-ESI m/z [M+H]+ calcd for $C_{22}H_{24}N_3O$: 346.1914, found: 346.1914.

4-(2-(1-fluoronaphthalen-2-yl)-4(5)-(3-(trifluoromethyl)phenyl)-1H-imidazol-5(4)-yl)pyridine (2t, IM-02)

Synthesized according to general procedure B using 10b and 1-fluoro-2-naphthaldehyde. 2t was obtained as a pale yellow solid in 32% yield (32 mg). $^1$H NMR (400 MHz, $CDCl_3$): δ=10.21 (s, 1H, NH), 8.67 (s, br, 1H), 8.44 (dd, J=11.1, 5.2 Hz, 1H), 8.20-8.13 (m, 2H), 7.90 (d, J=7.5 Hz, 1H), 7.84-7.36 (m, 9H); HRMS-ESI m/z [M+H]+ calcd for $C_{25}H_{16}F_4N_3$: 434.12749, found: 434.12802.

2-(2,6-difluorophenyl)-5(4)-(3,6-dihydro-2H-pyran-4-yl)-4(5)-(4-fluorophenyl)-1H-imidazole (3b, IM-23)

Synthesized according to general procedure A using 14a and 2,6-difluorobenzaldehyde. 3b was obtained as a pale yellow solid in 55% yield (31 mg). $^1$H NMR (400 MHz, CD$_3$OD): δ=7.58 (dd, J=8.4, 5.5 Hz, 2H), 7.55-7.47 (m, 1H), 7.16-7.09 (m, 4H), 5.98 (s, 1H), 4.23 (d, J=2.6 Hz, 2H), 3.84 (t, J=5.4 Hz, 2H), 2.35 (s, 2H); HRMS-ESI m/z [M+H]$^+$ calcd for C$_{20}$H$_{16}$F$_3$N$_2$O: 357.1209, found: 357.1208.

4-(5(4)-(3,6-dihydro-2H-pyran-4-yl)-4(5)-(4-fluorophenyl)-1H-imidazol-2-yl)phenol (3c, IM-24)

Synthesized according to general procedure B using 14a and 4-hydroxybenzaldehyde. 3c was obtained as an off-white solid in 63% yield (50 mg). $^1$H NMR (400 MHz, CD$_3$OD): δ=7.75 (d, J=8.9 Hz, 2H), 7.57 (dd, J=8.9, 5.4 Hz, 2H), 7.13 (t, J=8.9 Hz, 2H), 6.86 (d, J=8.9 Hz, 2H), 6.08-5.82 (m, 1H), 4.24 (q, J=2.8 Hz, 2H), 3.84 (t, J=5.4 Hz, 2H), 2.32 (td, J=5.2, 2.6 Hz, 2H); HRMS-ESI m/z [M+H]$^+$ calcd for C$_{20}$H$_{18}$FN$_2$O$_2$: 337.1347, found: 337.1345.

5(4)-(3,6-dihydro-2H-pyran-4-yl)-2-(2-fluorophenyl)-4(5)-(4-fluorophenyl)-1H-imidazole (3d, IM-20)

Synthesized according to general procedure B using 14a and 2-fluorobenzaldehyde. 3d was obtained as an off-white solid in 46% yield (25 mg). $^1$H NMR (400 MHz, CD$_3$OD): δ=7.91 (td, J=7.6, 1.6 Hz, 1H), 7.60-7.57 (m, 2H), 7.47-7.41 (m, 1H), 7.31-7.23 (m, 2H), 7.14 (t, J=8.4 Hz, 2H), 5.98 (s, 1H), 4.23 (d, J=2 Hz, 2H), 3.84 (t, J=5.2 Hz, 2H), 2.34 (s, 2H); HRMS-ESI m/z [M+H]$^+$ calcd for C$_{20}$H$_{17}$F$_2$N$_2$O: 339.1303, found: 339.1300.

5(4)-(3,6-dihydro-2H-pyran-4-yl)-2-(1-fluoronaphthalen-2-yl)-4(5)-(4-fluorophenyl)-1H-imidazole (3e, IM-22)

Synthesized according to general procedure A using 14a and 1-fluoro-2-naphthaldehyde. 3e was obtained as a pale yellow solid in 90% yield (49 mg). $^1$H NMR (400 MHz, CD$_3$OD): δ=8.17-8.15 (m, 1H), 7.98 (dd, J=8.6, 7.4 Hz, 1H), 7.93-7.91 (m, 1H), 7.75 (d, J=8.7 Hz, 1H), 7.62-7.56 (m, 4H), 7.14 (t, J=8.7 Hz, 2H), 6.00 (s, 1H), 4.24 (d, J=2.2 Hz, 2H), 3.85 (t, J=5.4 Hz, 2H), 2.36 (s, 2H); HRMS-ESI m/z [M+H]$^+$ calcd for C$_{24}$H$_{19}$F$_2$N$_2$O: 389.1460, found: 389.1455.

5(4)-(3,6-dihydro-2H-pyran-4-yl)-2-(2-fluorophenyl)-4(5)-(p-tolyl)-1H-imidazole (3f, IM-21)

To a solution of 1-ethynyl-4-methylbenzene (460 mg, 4 mmol, 2 equiv) in dry THF (8 mL) at room temperature was added a solution of n-BuLi (4 mmol, 2 equiv) in hexanes (2.4 M) dropwise while stirring. The solution was stirred for an additional 5 min after which anhydrous LiBr (695 mg, 8 mmol, 4 equiv) was added and the mixture was stirred at room temperature for a further 30 min. Following which, the mixture was cooled to −78° C. and transferred dropwise to a pre-cooled solution of tetrahydro-4H-pyran-4-one (200 mg, 2 mmol, 1 equiv) in dry THF (6 mL) at −78° C. The cooling bath was then removed and the reaction was allowed to warm up to room temperature. Stirring was continued for another 40 min after which the reaction was diluted with diethyl ether, washed with saturated NH$_4$Cl solution and dried over anhydrous Na$_2$SO$_4$. Removal of the solvent in vacuo gave the crude product which was purified by silica gel column chromatography to give 4-(p-tolylethynyl)tetrahydro-2H-pyran-4-ol as a white solid in quantitative yield (580 mg).

A solution of 4-(p-tolylethynyl)tetrahydro-2H-pyran-4-ol (550 mg, 2.5 mmol, 1 equiv) in a 6:1 mixture of 1,4-dioxane/H$_2$O was cooled to 0° C. KMnO$_4$ (1.6 g, 10.2 mmol, 4 equiv) was then added portionwise and the reaction was stirred at 0° C. for 5 min after which the ice bath was removed and the reaction stirred at room temperature. The reaction was monitored by TLC every 5 min and when TLC indicated the disappearance of the starting alkyne, the reaction was quenched with saturated NaHSO$_3$ solution at 0° C. The reaction was extracted with ethyl acetate and the organic extracts dried with anhydrous Na$_2$SO$_4$. Removal of the solvent in vacuo gave the crude product which was purified by silica gel column chromatography to give 14b as a yellow viscous liquid in 52% yield (320 mg).

Compound 3f was synthesized according to general procedure A using 14b and 2-fluorobenzaldehyde. 3f was obtained as an off-white solid in 79% yield. $^1$H NMR (400 MHz, CD$_3$OD): δ=7.90 (td, J=7.6, 2 Hz, 1H), 7.45-7.39 (m, 3H), 7.29-7.25 (m, 1H), 7.25-7.20 (m, 3H), 5.97 (m, 1H), 4.22 (dd, J=5.6, 2.8 Hz, 2H), 3.81 (t, J=5.2 Hz, 2H), 2.35 (s, 3H), 2.33 (m, 2H); HRMS-ESI m/z [M+H]$^+$ calcd for C$_{21}$H$_{20}$FN$_2$O: 335.1554, found: 335.1555.

2-(2,6-difluorophenyl)-5(4)-(3,6-dihydro-2H-pyran-4-yl)-4(5)-(m-tolyl)-1H-imidazole (4b, IM-18)

Synthesized according to general procedure B using 15 and 2,6-difluorobenzaldehyde. 4b was obtained as an off-white solid in 52% yield (60 mg). $^1$H NMR (400 MHz, CDCl$_3$): δ=9.65 (s, 1H), 7.52-7.41 (m, 1H), 7.33-7.26 (m, 3H), 7.16-7.11 (m, 1H), 7.05-6.98 (m, 2H), 6.09 (m, 1H), 4.26 (s, 2H), 3.83 (t, J=5.6 Hz, 2H), 2.43 (m, 2H), 2.39 (s, 3H); HRMS-ESI m/z [M+H]$^+$ calcd for C$_{21}$H$_{19}$F$_2$N$_2$O: 353.1460, found: 353.1456.

2-(2-bromophenyl)-5(4)-(3,6-dihydro-2H-pyran-4-yl)-4(5)-(m-tolyl)-1H-imidazole (4c, IM-13)

Synthesized according to general procedure A using 15 and 2-bromobenzaldehyde. 4c was obtained as an off-white solid in 84% yield (105 mg). $^1$H NMR (400 MHz, CD$_3$OD): δ=7.73 (dd, J=8, 0.8 Hz, 1H), 7.62 (dd, J=7.6, 2 Hz, 1H), 7.46 (td, J=7.2, 1.2 Hz, 1H), 7.40 (s, 1H), 7.38-7.34 (m, 2H), 7.28 (t, J=7.6 Hz, 1H), 7.14 (d, J=7.6 Hz, 1H), 5.99 (m, 1H), 4.24 (dd, J=5.6, 2.8 Hz, 2H), 3.83 (t, J=5.6 Hz, 2H), 2.37 (s, 3H), 2.36 (m, 2H); HRMS-ESI m/z [M+H]$^+$ calcd for C$_{21}$H$_{20}$BrN$_2$O: 395.0754, found: 395.0751.

5(4)-(3,6-dihydro-2H-pyran-4-yl)-2-(4-nitrophenyl)-4(5)-(m-tolyl)-1H-imidazole (4d, IM-17)

Synthesized according to general procedure A using 15 and 4-nitrobenzaldehyde. 4d was obtained as an orange solid in 54% yield (92 mg). $^1$H NMR (400 MHz, CD$_3$OD): δ=8.27 (d, J=8.8 Hz, 2H), 8.10 (d, J=8.8 Hz, 2H), 7.41 (s, 1H), 7.36 (d, J=7.6 Hz, 1H), 7.30 (t, J=7.2 Hz, 1H), 7.17 (d, J=6.8 Hz, 1H), 6.02 (s, 1H), 4.25 (s, 2H), 3.83 (t, J=5.2 Hz, 2H), 2.39 (s, 3H), 2.34 (s, 2H); HRMS-ESI m/z [M+H]$^+$ calcd for C$_{21}$H$_{20}$N$_3$O$_3$: 362.1499, found: 362.1510.

4-(5(4)-(3,6-dihydro-2H-pyran-4-yl)-4(5)-(m-tolyl)-1H-imidazol-2-yl)phenol (4e, IM-15)

Synthesized according to general procedure A using 15 and 4-hydroxybenzaldehyde. 4e was obtained as an off-white solid in 74% yield (28 mg). $^1$H NMR (400 MHz, CD$_3$OD): δ=7.76 (d, J=8.8 Hz, 2H), 7.38 (s, 1H), 7.33 (d, J=8 Hz, 1H), 7.26 (t, J=7.6 Hz, 1H), 7.12 (d, J=7.2 Hz, 1H), 6.86 (d, J=8.4 Hz, 2H), 5.97 (m, 1H), 4.24 (dd, J=5.6, 2.8 Hz, 2H), 3.82 (t, J=5.2 Hz, 2H), 2.37 (s, 3H), 2.32 (m, 2H); HRMS-ESI m/z [M+H]$^+$ calcd for $C_{21}H_{21}N_2O_2$: 333.1598, found: 333.1613.

2-(2-chlorophenyl)-5(4)-(3,6-dihydro-2H-pyran-4-yl)-4(5)-(m-tolyl)-1H-imidazole (4f, IM-12)

Synthesized according to general procedure A using 15 and 2-chlorobenzaldehyde. 4f was obtained as an off-white solid in 91% yield (100 mg). $^1$H NMR (400 MHz, CD$_3$OD): δ=7.70-7.67 (m, 1H), 7.55-7.53 (m, 1H), 7.45-7.39 (m, 3H), 7.36 (d, J=7.6 Hz, 1H), 7.28 (t, J=7.6 Hz, 1H), 7.14 (d, J=7.6 Hz, 1H), 5.99 (s, 1H), 4.24 (d, J=2.8 Hz, 2H), 3.83 (t, J=5.2 Hz, 2H), 2.38 (s, 5H); HRMS-ESI m/z [M+H]$^+$ calcd for $C_{21}H_{20}ClN_2O$: 351.1259, found: 351.1270.

5(4)-(3,6-dihydro-2H-pyran-4-yl)-2-(2-fluorophenyl)-4(5)-(m-tolyl)-1H-imidazole (4g, IM-06)

Synthesized according to general procedure A using 15 and 2-fluorobenzaldehyde. 4g was obtained as an off-white solid in 70% yield (66 mg). $^1$H NMR (400 MHz, CDCl$_3$): δ=9.62 (s, 1H), 8.34 (q, J=8 Hz, 1H), 7.54-7.43 (m, 1H), 7.35-7.24 (m, 4H), 7.18-7.10 (m, 2H), 6.10 (s, 1H), 4.30 (s, 2H), 3.85 (t, J=5.2 Hz, 2H), 2.40 (m, 5H); HRMS-ESI m/z [M+H]$^+$ calcd for $C_{21}H_{20}FN_2O$: 335.1554, found: 335.1572.

5(4)-(3,6-dihydro-2H-pyran-4-yl)-2-(1-fluoronaphthalen-2-yl)-4(5)-(m-tolyl)-1H-imidazole (4h, IM-03)

Synthesized according to general procedure A using 15 and 1-fluoro-2-naphthaldehyde. 4h was obtained as a pale yellow solid in 45% yield (28 mg). $^1$H NMR (400 MHz, CD$_3$OD): δ=8.19-8.17 (m, 1H), 8.00 (dd, J=8.6, 7.3 Hz, 1H), 7.94 (dt, J=8.3, 1.9 Hz, 1H), 7.77 (d, J=8.6 Hz, 1H), 7.65-7.56 (m, 2H), 7.44 (s, 1H), 7.39 (d, J=7.7 Hz, 1H), 7.30 (t, J=7.6 Hz, 1H), 7.16 (d, J=7.5 Hz, 1H), 6.03 (s, 1H), 4.26 (d, J=2.5 Hz, 2H), 3.85 (t, J=5.4 Hz, 2H), 2.39 (m, 5H); HRMS-ESI m/z [M+H]$^+$ calcd for $C_{25}H_{22}FN_2O$: 385.1711, found: 385.1682.

5(4)-(3,6-dihydro-2H-pyran-4-yl)-2-phenyl-4(5)-(m-tolyl)-1H-imidazole (4i, IM-11)

Synthesized according to general procedure A using 15 and benzaldehyde. 4i was obtained as an off-white solid in 67% yield (23 mg). $^1$H NMR (400 MHz, CD$_2$Cl$_2$): δ=7.90-7.88 (m, 2H), 7.44-7.40 (m, 3H), 7.37-7.33 (m, 2H), 7.26 (t, J=7.6 Hz, 1H), 7.12 (d, J=7.6 Hz, 1H), 6.00 (m, 1H), 4.23 (dd, J=5.4, 2.7 Hz, 2H), 3.81 (t, J=5.6 Hz, 2H), 2.37 (s, 3H), 2.33 (s, 2H); HRMS-ESI m/z [M+H]$^+$ calcd for $C_{21}H_{21}N_2O$: 317.1648, found: 317.1663.

5(4)-(3,6-dihydro-2H-pyran-4-yl)-2-(6-methoxynaphthalen-2-yl)-4(5)-(m-tolyl)-1H-imidazole (4j, IM-09)

Synthesized according to general procedure A using 15 and 6-methoxy-2-naphthaldehyde. 4j was obtained as an off-white solid in 92% yield (170 mg). $^1$H NMR (400 MHz, CD$_3$OD): δ=8.31 (s, 1H), 7.99 (dd, J=8.4, 1.2 Hz, 1H), 7.84-7.79 (m, 2H), 7.42 (s, 1H), 7.37 (d, J=7.6 Hz, 1H), 7.29 (t, J=7.2 Hz, 1H), 7.25 (d, J=2 Hz, 1H), 7.17-7.15 (m, 2H), 6.02 (s, 1H), 4.26 (dd, J=4.8, 2.4 Hz, 2H), 3.91 (s, 3H), 3.84 (t, J=5.6 Hz, 2H), 2.39 (s, 3H), 2.35 (m, 2H); HRMS-ESI m/z [M+H]$^+$ calcd for $C_{26}H_{25}N_2O_2$: 397.1911, found: 397.1913.

2-(5(4)-(3,6-dihydro-2H-pyran-4-yl)-4(5)-(m-tolyl)-1H-imidazol-2-yl)phenol (4k, IM-14)

Synthesized according to general procedure A using 15 and 2-hydroxybenzaldehyde. 4k was obtained as an off-white solid in 97% yield (91 mg). $^1$H NMR (400 MHz, CD$_3$OD): δ=7.77 (dd, J=7.6, 1.2 Hz, 1H), 7.40 (s, 1H), 7.36 (d, J=8H, 1H), 7.27 (t, J=7.6 Hz, 1H), 7.21 (ddd, J=8.4, 7.2, 1.6 Hz, 1H), 7.14 (d, J=7.6H, 1H), 6.94 (dd, J=8.4, 1.2 Hz, 1H), 6.88 (ddd, J=8, 7.2, 1.2 Hz, 1H), 6.01 (m, 1H), 4.23 (dd, J=5.6, 2.8 Hz, 2H), 3.83 (t, J=5.2 Hz, 2H), 2.37 (s, 3H), 2.36 (m, 2H); HRMS-ESI m/z [M+H]$^+$ calcd for $C_{21}H_{21}N_2O_2$: 333.1598, found: 333.1610.

5-(4-fluorophenyl)-2-(4-(methylsulfinyl)phenyl)-4-(pyridin-4-yl)oxazole (5b, OZ-12)

To a microwave vial containing a stirrer bar was added pivalic acid (17 mg, 0.2 mmol, 40 mol %), K$_2$CO$_3$ (170 mg, 1.3 mmol, 3 equiv), Pd(OAc)$_2$ (9 mg, 0.04 mmol, 10 mol %), 2-dicyclohexylphosphino-2',6'-diisopropoxy biphenyl (RuPhos, 39 mg, 0.08 mmol, 20 mol %) and 18b (100 mg, 0.4 mmol, 1 equiv). The microwave vial was capped, evacuated and backfilled with argon three times. Dry, degassed toluene (2.1 mL) was added via syringe followed by 4-bromothioanisole (130 mg, 0.6 mmol, 1.5 equiv). The microwave vial was sealed with parafilm and heated in an oil bath at 115° C. overnight. After cooling, the reaction mixture was diluted with ethyl acetate and washed with water. The organic phase was dried with anhydrous Na$_2$SO$_4$ and filtered. Removal of solvent in vacuo afforded the crude product which was purified by silica gel chromatography to give 19b as an off-white solid in 90% yield (140 mg).

To a solution of 19b (74 mg, 0.2 mmol, 1 equiv) in a mixture of glacial acetic acid (2.7 mL) and water (1.8 mL) was added K$_2$S$_2$O$_8$ (66 mg, 0.25 mmol, 1.2 equiv) at room temperature. The mixture was left to stir for 2 days at room temperature (44 hr). The reaction mixture was quenched with sat. NaHCO$_3$ and extracted with ethyl acetate. The combined organic phase was dried with anhydrous Na$_2$SO$_4$, and filtered. Removal of solvent in vacuo afforded the crude product. Purification by silica gel column chromatography (dichloromethane/methanol 100:3) afforded 5b as a white solid in 85% yield (66 mg). $^1$H NMR (400 MHz, CD$_3$OD) δ 8.57 (dd, J=4.6, 1.6 Hz, 2H), 8.34 (d, J=8.6 Hz, 2H), 7.88 (d, J=8.6 Hz, 2H), 7.76-7.72 (m, 4H), 7.27 (t, J=8.8 Hz, 2H), 2.87 (s, 3H); HRMS-ESI m/z [M+H]$^+$ calcd for $C_{21}H_{16}FN_2O_2S$: 379.0911, found: 379.0911.

The following compounds have been additionally synthesized and found to be cardiogenic in the same way. These 2,4,5-trisubstituted azoles also promote cardiac differentiation across several embryonic and iPS cell lines, and also on microcarriers:

4-[4(5)-(4-fluorophenyl)-2-phenyl-1H-imidazol-5(4)-yl]pyridine (ZQX-14)

Synthesized according to general method A for 2,4,5-trisubstituted imidazoles. A solution of 1-(4-fluorophenyl)-2-(pyridin-4-yl)ethane-1,2-dione (20 mg, 0.1 mmol, 1 equiv), NH$_4$OAc (72 mg, 0.9 mmol 10 equiv), and benzaldehyde (12 mg, 0.11 mmol, 1.1 equiv) in glacial acetic acid (3 mL) was stirred at 115° C. overnight. Purification by silica gel column chromatography (dichloromethane/methanol 20:1) afforded ZQX-14 as a light yellow solid in 46% yield (13 mg). $R_f$=0.2 (dichloromethane/methanol 20:1); mp: 232-233° C. decomposed; $^1$H NMR (400 MHz, CD$_3$OD): δ 8.45 (s, 2H), 8.00 (d, J=8.8 Hz, 2H), 7.54 (d, J=8.8 Hz, 2H), 7.52-7.42 (m, 5H), 7.20 (apparent t, J=8.4 Hz, 2H); $^{13}$C NMR (100 MHz, CD$_3$OD): δ 164.39 (d, J=245.5 Hz), 150.1, 149.3, 132.17 (d, J=8.4 Hz), 130.9, 130.4, 130.0, 127.1, 123.4, 117.0, 116.78 (d, J=22 Hz); HRMS-ESI m/z [M+H]$^+$ calcd for C$_{20}$H$_{14}$FN$_3$+H$^+$: 316.1250, found: 316.1252. HPLC purity: >99%.

4-[2-(2,6-dichlorophenyl)-4(5)-(4-fluorophenyl)-1H-imidazol-5(4)-yl]pyridine (ZQX-15)

Synthesized according to general method A for 2,4,5-trisubstituted imidazoles. A solution of 1-(4-fluorophenyl)-2-(pyridin-4-yl)ethane-1,2-dione (23 mg, 0.1 mmol, 1 equiv), NH$_4$OAc (77.8 mg, 1 mmol 10 equiv), and 2,6-dichlorobenzaldehyde (19.3 mg, 0.11 mmol, 1.1 equiv) in glacial acetic acid (3 mL) was stirred at 115° C. overnight. Purification by silica gel column chromatography (dichloromethane/methanol 20:1) afforded ZQX-15 as a pale solid in 55% yield (21 mg). $R_f$=0.3 (dichloromethane/methanol 20:1); mp: 258-260° C. $^1$H NMR (400 MHz, CD$_3$OD): δ 8.45 (s, 2H), 7.67-7.50 (m, 7H), 7.21 (br s, 2H); $^{13}$C NMR (100 MHz, CD$_3$OD): δ 164.39 (d, J=246 Hz) 150.3, 137.8, 133.77 (d, J=3 Hz), 133.3, 133.1, 133.0, 131.88 (d, J=9 Hz), 130.8, 129.97 (d, J=12 Hz), 129.4, 123.1, 117.05 (d, J=22 Hz); HRMS-ESI m/z [M+H]$^+$ calcd for C$_{20}$H$_{12}$Cl$_2$FN$_3$+H$^+$: 384.0471, found: 384.0481, HPLC purity: >96%.

4-[2-(2-methoxyphenyl)-4(5)-(4-fluorophenyl)-1H-imidazol-5(4)-yl]pyridine (ZQX-16)

Synthesized according to general method A for 2,4,5-trisubstituted imidazoles. A solution of 1-(4-fluorophenyl)-2-(pyridin-4-yl)ethane-1,2-dione (32 mg, 0.14 mmol, 1 equiv), NH$_4$OAc (108.9 mg, 1.4 mmol 10 equiv), and 2-methoxybenzaldehyde (22 mg, 0.16 mmol, 1.1 equiv) in glacial acetic acid (3 mL) was stirred at 115° C. overnight. Purification by silica gel column chromatography (dichloromethane/methanol 20:1) afforded ZQX-16 as a pale solid in 62.5% yield (30 mg). $R_f$=0.2 (dichloromethane/methanol 20:1); mp: 184-185° C.; $^1$H NMR (400 MHz, CD$_3$OD): δ 8.41 (s, 2H), 8.03 (d, J=9.2 Hz, 1H), 7.53-7.49 (m, 4H), 7.45-7.41 (m, 1H), 7.21-7.15 (m, 3H), 7.10 (apparent t, J=7.6 Hz 1H), 3.98 (s, 3H); $^{13}$C NMR (100 MHz, CD$_3$OD) δ 164.36 (d, J=245.5), 158.1, 150.1, 132.05 (d, J=30.1 Hz), 130.5, 123.2, 122.0, 119.3, 116.83 (d, J=21.9 Hz), 112.5, 56.2; HRMS-ESI m/z [M+H]$^+$ calcd for C$_{21}$H$_{16}$FN$_3$O+H$^+$: 346.1356, found: 346.1363, HPLC purity: >96%.

4-[2-(2-chlorophenyl)-4(5)-(4-fluorophenyl)-1H-imidazol-5(4)-yl]pyridine (ZQX-17)

Synthesized according to general method A for 2,4,5-trisubstituted imidazoles. A solution of 1-(4-fluorophenyl)-2-(pyridin-4-yl)ethane-1,2-dione (23 mg, 0.1 mmol, 1 equiv), NH$_4$OAc (77.8 mg, 1 mmol 10 equiv), and 2-chlorobenzaldehyde (15.5 mg, 0.11 mmol, 1.1 equiv) in glacial acetic acid (3 mL) was stirred at 115° C. overnight. Purification by silica gel column chromatography (dichloromethane/methanol 20:1) afforded ZQX-17 as a white solid in 51% yield (17.8 mg). $R_f$=0.2 (dichloromethane/methanol 20:1); mp: 220-221° C. $^1$H NMR (400 MHz, CD$_3$OD): δ 8.43 (d, J=4.8 Hz, 2H), 7.77-7.74 (m, 1H), 7.59-7.57 (m, 1H), 7.55-7.51 (m, 4H), 7.49-7.45 (m, 2H), 7.20 (apparent t, 2H); $^{13}$C NMR (100 MHz, CD$_3$OD) δ=164.35 (d, J=245.8 Hz), 150.2, 146.7, 134.1, 132.9, 132.1, 132.01 (d, J=8.2 Hz), 131.3, 130.8, 128.3, 123.1, 116.97 (d, J=21.9 Hz); HRMS-ESI m/z [M+H]$^+$ calcd for C$_{20}$H$_{13}$ClFN$_3$+H$^+$: 350.0860, found: 350.0869, HPLC purity: >96%.

4-[2-(2,6-dimethoxyphenyl)-4(5)-(4-fluorophenyl)-1H-imidazol-5(4)-yl]pyridine (ZQX-18)

Synthesized according to general method A for 2,4,5-trisubstituted imidazoles. A solution of 1-(4-fluorophenyl)-2-(pyridin-4-yl)ethane-1,2-dione (35 mg, 0.15 mmol, 1 equiv), NH$_4$OAc (116.7 mg, 1.5 mmol 10 equiv), and 2,6-dimethoxybenzaldehyde (28 mg, 0.17 mmol, 1.1 equiv) in glacial acetic acid (3 mL) was stirred at 115° C. overnight. Purification by silica gel column chromatography (dichloromethane/methanol 20:1) afforded ZQX-18 as a pale solid in 38% yield (21.4 mg). $R_f$=0.2 (dichloromethane/methanol 20:1); mp: 199-200° C. decomposed. $^1$H NMR (400 MHz, CD$_3$OD): δ 8.41 (s, 2H), 7.53-7.50 (m, 4H), 7.44 (t, J=8.4 Hz, 1H), 7.18 (m, 2H), 6.77 (d, J=8.4 Hz, 2H), 3.81 (s, 6H), $^{13}$C NMR (100 MHz, CD$_3$OD) δ 164.19 (d, J=245.2 Hz), 161.0, 151.0, 143.6, 132.8, 131.85 (d, J=8.2 Hz), 123.0, 116.84 (d, J=21.8 Hz), 109.6, 105.0, 61.5, 56.4; HRMS-ESI m/z [M+H]$^+$ calcd for C$_{22}$H$_{18}$FN$_3$O$_2$+H$^+$: 376.1461, found: 376.1473, HPLC purity: >96%.

4-[2-(2-chloro-6-fluorophenyl)-4(5)-(4-fluorophenyl)-1H-imidazol-5(4)-yl]pyridine (ZQX-19)

Synthesized according to general method A for 2,4,5-trisubstituted imidazoles. A solution of 1-(4-fluorophenyl)-2-(pyridin-4-yl)ethane-1,2-dione (40 mg, 0.18 mmol, 1 equiv), NH$_4$OAc (140.0 mg, 1.8 mmol 10 equiv), and 2-chloro-6-fluorobenzaldehyde (30 mg, 0.20 mmol, 1.1 equiv) in glacial acetic acid (5 mL) was stirred at 115° C. overnight. Purification by silica gel column chromatography (dichloromethane/methanol 20:1) afforded ZQX-19 as light yellow solid in 45% yield (30 mg). $R_f$=0.2 (dichloromethane/methanol 20:1); mp: 274-276° C. $^1$H NMR (400 MHz, CD$_3$OD) δ 8.45 (s, 2H), 7.59-7.52 (m, 5H), 7.46 (d, J=8.0 Hz, 1H), 7.32-7.27 (m, 1H), 7.21 (m, 2H); $^{13}$C NMR (100 MHz, CD$_3$OD) δ 162.95 (d, J=250 Hz), 150.3, 136.88 (d, J=3 Hz), 133.51 (d, J=9 Hz), 131.93 (d, J=8 Hz), 126.92 (d, J=4 Hz), 123.1, 120.2, 120.0, 117.0, 115.8, 115.6; HRMS-ESI m/z [M+H]$^+$ calcd for C$_{20}$H$_{12}$ClF$_2$N$_3$+H$^+$: 368.0766, found: 368.0761, HPLC purity: >98%.

4-[2-(2-fluoro-6-methoxyphenyl)-4(5)-(4-fluorophenyl)-1H-imidazol-5(4)-yl]pyridine (ZQX-20)

Synthesized according to general method A for 2,4,5-trisubstituted imidazoles. A solution of 1-(4-fluorophenyl)-2-(pyridin-4-yl)ethane-1,2-dione (40 mg, 0.18 mmol, 1 equiv), NH$_4$OAc (140.0 mg, 1.8 mmol 10 equiv), and 2-fluoro-6-methoxybenzaldehyde (30 mg, 0.20 mmol, 1.1 equiv) in glacial acetic acid (5 mL) was stirred at 115° C. overnight. Purification by silica gel column chromatography (dichloromethane/methanol 20:1) afforded ZQX-20 as light yellow solid in 38% yield (25 mg). $R_f$=0.2 (dichloromethane/methanol 20:1); mp: 203-205° C. $^1$H NMR (400 MHz, CD$_3$OD) δ 8.42 (d, J=4.9 Hz, 2H), 7.53-7.45 (m, 5H), 7.20 (br s, 2H), 6.98 (d, J=8.5 Hz, 1H), 6.93-6.88 (t, J=8.0 Hz, 1H), 3.88 (s, 3H); $^{13}$C NMR (100 MHz, CD$_3$OD) δ 162.88 (d, J=246 Hz), 160.8 (d, J=6 Hz), 150.2, 133.04 (d, J=10 Hz), 131.96 (d, J=8 Hz), 123.1, 116.83, 109.2, 109.0, 108.20

(d, J=3 Hz), 56.8. HRMS-ESI m/z [M+H]$^+$ calcd for C$_{21}$H$_{15}$F$_2$N$_3$O+H$^+$: 364.1261, found: 364.1256, HPLC purity: >97%.

4-[2-(2-bromo-6-fluorophenyl)-4(5)-(4-fluorophenyl)-1H-imidazol-5(4)-yl]pyridine (ZQX-21)

Synthesized according to general method A for 2,4,5-trisubstituted imidazoles. A solution of 1-(4-fluorophenyl)-2-(pyridin-4-yl)ethane-1,2-dione (40 mg, 0.18 mmol, 1 equiv), NH$_4$OAc (140.0 mg, 1.8 mmol 10 equiv), and 2-chloro-6-bromobenzaldehyde (43 mg, 0.20 mmol, 1.1 equiv) in glacial acetic acid (5 mL) was stirred at 115° C. overnight. Purification by silica gel column chromatography (dichloromethane/methanol 20:1) afforded ZQX-21 as light yellow solid in 37% yield (25 mg). R$_f$=0.2 (dichloromethane/methanol 20:1); mp: 266-268° C. $^1$H NMR (400 MHz, CD$_3$OD) δ 8.45 (d, J=4.6 Hz, 2H), 7.66-7.59 (m, 1H), 7.59-7.44 (m, 5H), 7.37-7.30 (m, 1H), 7.21 (apparent t, J=8.7 Hz, 2H); $^{13}$C NMR (100 MHz, CD$_3$OD) δ 164.39 (d, J=245.9 Hz), 162.89 (d, J=250.2 Hz), 150.27, 142.16, 133.95 (d, J=9.2 Hz), 131.91 (d, J=8.4 Hz), 130.06 (d, J=3.6 Hz), 126.15 (d, J=2.2 Hz), 123.23, 122.04, 122.14 (d, J=18.4 Hz), 117.03 (d, J=22.0 Hz), 116.27, 116.04. HRMS-ESI m/z [M+H]$^+$ calcd for C$_{20}$H$_{12}$BrF$_2$N$_3$+H$^+$: 412.0261, found: 412.0246, HPLC purity: >95%.

4-[2-(2-bromophenyl)-4(5)-(4-fluorophenyl)-1H-imidazol-5(4)-yl]pyridine (ZQX-22)

Synthesized according to general method A for 2,4,5-trisubstituted imidazoles. A solution of 1-(4-fluorophenyl)-2-(pyridin-4-yl)ethane-1,2-dione (40 mg, 0.18 mmol, 1 equiv), NH$_4$OAc (140.0 mg, 1.8 mmol 10 equiv), and 2-bromobenzaldehyde (25 ml, 0.20 mmol, 1.1 equiv) in glacial acetic acid (5 mL) was stirred at 115° C. overnight. Purification by silica gel column chromatography (dichloromethane/methanol 20:1) afforded ZQX-22 as white solid in 34% yield (24 mg). R$_f$=0.3 (dichloromethane/methanol 20:1). mp: 198-200° C. $^1$H NMR (400 MHz, CD$_3$OD) δ 8.44 (d, J=5.4 Hz, 2H), 7.77 (dd, J=8.0, 1.1 Hz, 1H), 7.69 (dd, J=7.6, 1.7 Hz, 1H), 7.56-7.49 (m, 5H), 7.43-7.39 (m, 1H), 7.20 (apparent t, J=8.8 Hz, 2H); $^{13}$C NMR (100 MHz, CD$_3$OD) δ 164.36 (d, J=246 Hz), 150.21, 148.04, 134.54, 133.08, 132.33, 132.02, 131.94, 128.77, 123.74, 123.13, 117.09, 116.87. HRMS-ESI m/z [M+H]$^+$ calcd for C$_{20}$H$_{13}$BrFN$_3$+H$^+$: 394.0355, found: 394.0340, HPLC purity: >96%.

4-[2-(2H-1,3-benzodioxol-5-yl)-4(5)-(4-fluorophenyl)-1H-imidazol-5(4)-yl]pyridine (ZQX-23)

Synthesized according to general method A for 2,4,5-trisubstituted imidazoles. A solution of 1-(4-fluorophenyl)-2-(pyridin-4-yl)ethane-1,2-dione (40 mg, 0.18 mmol, 1 equiv), NH$_4$OAc (140.0 mg, 1.8 mmol 10 equiv), and piperonal (32 mg, 0.20 mmol, 1.1 equiv) in glacial acetic acid (5 mL) was stirred at 115° C. overnight. Purification by silica gel column chromatography (dichloromethane/methanol 20:1) afforded ZQX-23 as yellow solid in 56% yield (35 mg). R$_f$=0.2 (dichloromethane/methanol 20:1). mp: 260-262° C. $^1$H NMR (400 MHz, CD$_3$OD) δ 8.43 (d, J=5.1 Hz, 2H), 7.54-7.49 (m, 4H), 7.20 (apparent t, J=8.7 Hz, 2H), 6.94 (d, J=8.0 Hz, 1H), 6.03 (s, 2H). $^{13}$C NMR (100 MHz, CDCl$_3$) δ 164.01 (d, J=246 Hz), 149.86, 149.38, 149.06, 131.76 (d, J=8.2 Hz), 129.51, 124.58, 121.16, 116.73 (d, J=21 Hz), 109.36, 107.24, 102.56. HRMS-ESI m/z [M+H]$^+$ calcd for C$_{21}$H$_{14}$FN$_3$O$_2$+H$^+$: 360.1182, found: 360.1139, HPLC purity: >96%.

4-[2-(2-chloro-6-nitrophenyl)-4(5)-(4-fluorophenyl)-1H-imidazol-5(4)-yl]pyridine (ZQX-25)

Synthesized according to general method for 2,4,5-trisubstituted imidazoles. A solution of 1-(4-fluorophenyl)-2-(pyridin-4-yl)ethane-1,2-dione (40 mg, 0.18 mmol, 1 equiv), NH$_4$OAc (140.0 mg, 1.8 mmol 10 equiv), and 2-chloro-6-nitrobenzaldehyde (40 mg, 0.20 mmol, 1.1 equiv) in glacial acetic acid (5 mL) was stirred at 115° C. overnight. Purification by silica gel column chromatography (dichloromethane/methanol 20:1) afforded ZQX-25 as light yellow solid in 58% yield (40 mg). R$_f$=0.2 (dichloromethane/methanol 20:1). mp: 268-270° C. $^1$H NMR (400 MHz, CD$_3$OD) δ 8.44 (s, 2H), 8.12 (dd, J=8.2, 0.9 Hz, 1H), 7.97 (dd, J=8.2, 0.9 Hz, 1H), 7.78 (t, J=8.2 Hz, 1H), 7.56-7.50 (m, 4H), 7.24-7.18 (m, 2H); $^{13}$C NMR (100 MHz, Acetone-D$_6$) δ 163.62 (d, J=245 Hz), 152.47, 150.78, 140.39, 136.69, 134.81, 132.53, 131.52, 126.03, 123.92, 121.97, 116.77, 116.56. HRMS-ESI m/z [M+H]$^+$ calcd for C$_{20}$H$_{12}$ClFN$_4$O$_2$+H$^+$: 395.0711, found: 395.0720, HPLC purity: >97%.

2-[4(5)-(4-fluorophenyl)-5(4)-(pyridin-4-yl)-1H-imidazol-2-yl]-3,5-dimethoxyphenol (ZQX-26)

Synthesized according to general method A for 2,4,5-trisubstituted imidazoles. A solution of 1-(4-fluorophenyl)-2-(pyridin-4-yl)ethane-1,2-dione (40 mg, 0.18 mmol, 1 equiv), NH$_4$OAc (140.0 mg, 1.8 mmol 10 equiv), and 2-hydroxy-4,6-dimethoxybenzaldehyde (40 mg, 0.20 mmol, 1.1 equiv) in glacial acetic acid (5 mL) was stirred at 115° C. overnight. Purification by silica gel column chromatography (dichloromethane/methanol 20:1) afforded ZQX-26 as yellow solid in 44% yield (30 mg). R$_f$=0.2 (dichloromethane/methanol 20:1). mp: 204-206° C. $^1$H NMR (400 MHz, CD$_3$OD) δ 8.41 (d, J=6.0 Hz, 2H), 7.56-7.53 (m, 2H), 7.51-7.49 (m, 2H), 7.22 (apparent t, J=8.0 Hz, 2H), 6.21 (dd, J=12.3, 2.3 Hz, 2H), 3.97 (s, 3H), 3.82 (s, 3H). $^{13}$C NMR (100 MHz, CD$_3$OD) δ 164.47 (d, J=245 Hz), 163.50, 161.76, 159.78, 150.13, 147.21, 132.37, 122.59, 117.03, 116.81, 97.03, 95.38, 91.17, 56.37, 55.86. HRMS-ESI m/z [M+H]$^+$ calcd for C$_{22}$H$_{18}$FN$_3$O$_3$+H$^+$: 392.1410, found: 392.1405, HPLC purity: >97%.

4-[4(5)-(4-fluorophenyl)-2-(2-nitrophenyl)-1H-imidazol-5(4)-yl]pyridine (ZQX-27)

Synthesized according to general method A for 2,4,5-trisubstituted imidazoles. A solution of 1-(4-fluorophenyl)-2-(pyridin-4-yl)ethane-1,2-dione (100 mg, 0.44 mmol, 1 equiv), NH$_4$OAc (342.0 mg, 4.4 mmol 10 equiv), and 2-nitrobenzaldehyde (80 mg, 0.53 mmol, 1.2 equiv) in glacial acetic acid (5 mL) was stirred at 115° C. overnight. Purification by silica gel column chromatography (dichloromethane/methanol 20:1) afforded ZQX-27 as yellow solid in 34% yield (53.8 mg). R$_f$=0.2 (dichloromethane/methanol 20:1). mp: 227-230° C. $^1$H NMR (400 MHz, CD$_3$OD) δ 8.43 (s, 2H), 8.09 (d, J=8.1 Hz, 1H), 7.86-7.80 (m, 2H), 7.74-7.70 (m, 1H), 7.55-7.52 (m, 4H), 7.21 (apparent t, J=8.3 Hz, 2H). $^{13}$C NMR (100 MHz, CDCl$_3$) δ 163.49 (d, J=247 Hz), 149.30, 148.92, 144.03, 133.47, 132.22, 131.14, 131.06, 130.83, 125.50, 125.22, 122.32, 116.55, 116.33. MS-ESI m/z [M+H]$^+$ calcd for C$_{20}$H$_{13}$FN$_4$O$_2$: 360.1, found: 361.4, HPLC purity: >97%.

4-[2-(2,6-dimethylphenyl)-4(5)-(4-fluorophenyl)-1H-imidazol-5(4)-yl]pyridine (ZQX-28)

Synthesized according to general A method for 2,4,5-trisubstituted imidazoles. A solution of 1-(4-fluorophenyl)-2-(pyridin-4-yl)ethane-1,2-dione (85 mg, 0.37 mmol, 1 equiv), NH$_4$OAc (288 mg, 3.7 mmol 10 equiv), and 2,6-dimethybenzaldehyde (60 mg, 0.45 mmol, 1.2 equiv) in glacial acetic acid (5 mL) was stirred at 115° C. overnight. Purification by silica gel column chromatography (dichloromethane/methanol 20:1) afforded ZQX-28 as light red solid in 40.5% yield (50 mg). R$_f$=0.2 (dichloromethane/methanol 20:1). mp: 285-287° C. $^1$H NMR (400 MHz, CD$_3$OD) δ 8.42 (d, J=8 Hz, 2H), 7.56-7.52 (m, 4H), 7.31-7.27 (m, 1H) 7.22-7.16 (m, 4H), 2.24 (s, 6H). $^{13}$C NMR (100 MHz, CD$_3$OD) δ 164.25 (d, J=245 Hz), 150.23, 148.59, 143.46, 139.67, 131.82 (d, J=8.2 Hz), 130.73, 128.51, 122.95, 116.98 (d, J=22 Hz), 20.21. MS-ESI m/z [M+H]$^+$ calcd for C$_{22}$H$_{18}$FN$_3$: 343.2, found: 344.1, HPLC purity: >99%.

4-[4(5)-(4-fluorophenyl)-2-(2-methylphenyl)-1H-imidazol-5(4)-yl]pyridine (ZQX-29)

Synthesized according to general method A for 2,4,5-trisubstituted imidazoles. A solution of 1-(4-fluorophenyl)-2-(pyridine-4-yl)ethane-1,2-dione (58 mg, 0.26 mmol, 1 equiv), NH$_4$OAc (202 mg, 2.6 mmol 10 equiv), and 2-methylbenzaldehyde (40 mg, 0.31 mmol, 1.2 equiv) in glacial acetic acid (5 mL) was stirred at 115° C. overnight. Purification by silica gel column chromatography (dichloromethane/methanol 20:1) afforded ZQX-29 as light yellow solid in 21% yield (18 mg). R$_f$=0.2 (dichloromethane/methanol 20:1); mp: 218-219° C. $^1$H NMR (400 MHz, CD$_3$OD) δ 8.43 (s, 2H), 7.58-7.53 (m, 5H), 7.38-7.30 (m, 3H), 7.20 (apparent t, J=8.7 Hz, 2H), 2.54 (s, 3H). $^{13}$C NMR (100 MHz, CD$_3$OD) δ 164.32 (d, J=245 Hz), 150.17, 149.62, 138.53, 132.03, 131.96, 131.18, 130.64 (d, J=11.2 Hz), 126.99, 123.06, 116.94 (d, J=22 Hz), 20.55. MS-ESI m/z [M+H]$^+$ calcd for C$_{21}$H$_{16}$FN$_3$: 329.1, found: 330.4, HPLC purity: >97%.

4-[2-(2-fluoro-6-iodophenyl)-4(5)-(4-fluorophenyl)-1H-imidazol-5(4)-yl]pyridine (ZQX-30)

Synthesized according to general method A for 2,4,5-trisubstituted imidazoles. A solution of 1-(4-fluorophenyl)-2-(pyridin-4-yl)ethane-1,2-dione (64 mg, 0.28 mmol, 1 equiv), NH$_4$OAc (218 mg, 2.8 mmol 10 equiv), and 2-fluoro-6-iodobenzaldehyde (84 mg, 0.34 mmol, 1.2 equiv) in glacial acetic acid (5 mL) was stirred at 115° C. overnight. Purification by silica gel column chromatography (dichloromethane/methanol 20:1) afforded ZQX-30 as light yellow solid in 16% yield (20 mg). R$_f$=0.2 (dichloromethane/methanol 20:1); mp: 250-253° C. $^1$H NMR (400 MHz, CD$_3$OD/CDCl$_3$ 1:1) δ 8.40 (s, 2H), 7.78-7.76 (m, 1H), 7.54-7.47 (m, 4H), 7.22-7.17 (m, 2H), 7.11 (apparent t, J=8 Hz). $^{13}$C NMR (100 MHz, CD$_3$OD) δ 163.26 (d, J=247 Hz) 160.96 (d, J=252 Hz), 148.88, 143.31, 135.54 (d, J=3.6 Hz), 133.03 (d, J=8.7 Hz), 130.88 (d, J=8.2 Hz), 124.95 (d, J=17.4 Hz), 122.30, 116.40, 116.19, 116.12, 115.90, 99.81. MS-ESI m/z [M+H]$^+$ calcd for C$_{20}$H$_{12}$F$_2$IN$_3$: 459.0, found: 460.2, HPLC purity: >97%.

4-[2-(2-aminophenyl)-4(5)-(4-fluorophenyl)-1H-imidazol-5(4)-yl]pyridine (ZQX-31)

To a solution of ZQX-27 (30 mg, 0.08 mol) in methanol and DCM (1:1, 5 ml) was added palladium on charcoal (10%, 6 mg) under the protection of N$_2$. Hydrogen gas was introduced into the solution via a balloon and the reaction mixture was stirred at room temperature for 12 hours. The reaction mixture was filtered over celite and methanol was removed in vacuo to give the crude product. Purification by silica gel column chromatography afforded ZQX-31 as light yellow oil in 57% yield (15 mg). R$_f$=0.4 (dichloromethane/methanol 20:1). $^1$H NMR (400 MHz, CD$_3$OD/CDCl$_3$ 1:1) 8.32 (d, J=6.2 Hz, 2H), 7.64 (d, J=6.2 Hz, 2H), 7.57 (dd, J=7.9, 1.2 Hz, 1H), 7.48-7.44 (m, 2H), 7.13-7.08 (m, 3H), 6.78 (d, J=7.5 Hz, 1H), 6.71-6.67 (m, 1H). $^{13}$C NMR (100 MHz, CD$_3$OD/CDCl$_3$ 1:1) δ 163.46 (d, J=248 Hz), 148.66, 146.36, 146.04, 131.24 (d, J=8.3 Hz), 130.31, 126.84, 121.88, 117.57, 117.26, 116.45 (d, J=21 Hz), 112.49. MS-ESI m/z [M+H]$^+$ calcd for C$_{20}$H$_{15}$FN$_4$: 330.1, found: 331.4, HPLC purity: >97%.

4-[2-(2-methoxy-5-nitrophenyl)-4(5)-(4-fluorophenyl)-1H-imidazol-5(4)-yl]pyridine (ZQX-32)

Synthesized according to general method A for 2,4,5-trisubstituted imidazoles. A solution of 1-(4-fluorophenyl)-2-(pyridin-4-yl)ethane-1,2-dione (40 mg, 0.17 mmol, 1 equiv), NH$_4$OAc (140 mg, 1.7 mmol 10 equiv), and 2-methoxyl-5-nitrobenzaldehyde (40 mg, 0.20 mmol, 1.2 equiv) in glacial acetic acid (5 mL) was stirred at 115° C. overnight. Purification by silica gel column chromatography (dichloromethane/methanol 20:1) afforded ZQX-32 as light yellow oil in 57% yield (38 mg). R$_f$=0.3 (dichloromethane/methanol 20:1). $^1$H NMR (400 MHz, CD$_3$OD) δ 9.01 (d, J=2.8 Hz, 1H), 8.46 (s, 2H), 8.31 (dd, J=9.2, 2.8 Hz, 1H), 7.78 (s, 2H), 7.56-7.53 (m, 3H), 7.28 (d, J=9.2 Hz, 1H), 7.22 (apparent, J=8.6 Hz, 2H), 4.11 (s, 4H). $^{13}$C NMR (100 MHz, CD$_3$OD) δ 164.21 (d, J=248 Hz) 161.91, 146.32, 144.29, 142.58, 131.96 (d, J=8.4 Hz), 126.91, 125.81, 119.69, 117.03, 116.81, 112.64, 57.21. MS-ESI m/z [M+H]$^+$ calcd for C$_{21}$H$_{15}$FN$_4$O$_3$: 390.1, found: 391.1; HPLC purity: >96%.

Known commercial compounds were used as shown in Table 1

TABLE 1

| Compound | Company | Concentration used (μM) | IC$_{50}$ (published by companies) |
| --- | --- | --- | --- |
| BIRB 796 (Doramapimod) | Selleckchem | 1-10 | 0.1 nM (p38 MAPK inhibition) |
| CHIR99021 | R&D Systems (Tocris) | 3 | 10 nM (p38α MAPK inhibition) 6.7 nM (p38β MAPK inhibition) |
| D4476 | Cayman Chemical | 5 | 200 nM (CK1 inhibition) 9.1 μM (PKD1 inhibition) 5.8 μM (p38α MAPK inhibition) |

TABLE 1-continued

| Compound | Company | Concentration used (μM) | IC$_{50}$ (published by companies) |
|---|---|---|---|
| IWP-2 | Stemgent | 5 | 27 nM (porcupine/Wnt inhibition) |
| SB202190 | Sigma-Aldrich | 5 | 50 nM (p38α MAPK inhibition) |
| | | | 100 nM (p38β MAPK inhibition) |
| SB203580 | Sigma-Aldrich | 1-10 | 0.3-0.5 μM (p38 MAPK inhibition) |
| | | | 3-5 μM (PKB phosphorylation) |
| SB431542 | Sigma-Aldrich | 5 | 94 nM (ALK5) |
| Skepinone-L | ShangHai Biochempartner | 1-10 | 5 nM (p38-MAPK inhibition) |
| | | | 40 nM (TNF-a inhibition) |
| TAK 715 | R&D Systems | 5 | 7.1 nM (p38α MAPK inhibition) |
| VX-745 | Selleckchem | 1-10 | 10 nM (p38α MAPK inhibition) |
| | | | 220 nM (p38β MAPK inhibition) |

Example 3: Kinase Assay to Determine IC$_{50}$ Values Against p38alpha Mitogen-Activated Protein Kinase (p38α MAPK), Casein Kinase 1 Epsilon (CK1ε) and 1 Delta (CK1δ)

The p38 MAPK IC$_{50}$ values of selected compounds except IM-32 to IM-44 were determined using the HitHunter™ p38 MAP kinase binding assay from DiscoveRx Corporation (Fremont, Calif., USA). The p38 MAPK IC$_{50}$ values of IM-32 to IM-44 and the CK1 IC$_{50}$ values of selected compounds were determined using LanthaScreen™ Eu kinase binding assay from Invitrogen (Life Technologies, Carlsbad, Calif., USA). The assays were performed following the manufacturers' protocols in white 384-well plates (Cat. No. 3572; Corning Incorporated, Corning, N.Y., USA). SB203580 was used as the control in all assays. For the HitHunter™ p38 MAP kinase binding assay the compounds were dissolved in DMSO (5 mM stocks) and diluted to a final concentration of 2% (vol/vol) DMSO for all assays. Recombinant GST-tagged active p38α MAP kinase enzyme (Millipore, Billerica, Mass., USA) was used for the HitHunter™ p38 MAP kinase binding assay. For the LanthaScreen™ Eu kinase binding assay the compounds were dissolved in DMSO (5 mM stocks) and diluted to a final concentration of 1% (vol/vol) DMSO for all assays. Each data point was done in triplicate. The assay was run using JANUS Automated Workstation according to the protocol developed using WinPREP software (Perkin Elmer Inc., Waltham, Mass., USA). Tecan Infinite® M1000 microplate reader (Tecan Group Ltd., Minnedorf, Switzerland) was used for luminescence measurements (HitHunter™ p38 MAP kinase binding assay) and fluorescence measurements (LanthaScreen™ Eu kinase binding assay; ex=340 nm, em=665, 615 nm). All data analysis was performed using GraphPad Prism 5 software (GraphPad Software Inc.). Inhibition curves and IC$_{50}$ values were generated by nonlinear regression analysis and data represent mean±SEM.

Table 2 shows the structures of 2,4,5-tri-substituted azole compounds synthesized or obtained as mentioned in Example 2, (previously published compounds are indicated with *) and their IC$_{50}$ values against p38α MAPK, CK1δ, and CK1ε. The in vitro IC$_{50}$ values of the synthesized compounds against the relevant kinase targets are summarized. The IC$_{50}$ values were determined using either the HitHunter™ p38 MAPK binding assay from DiscoveRx or the LanthaScreen™ Eu kinase binding assay (for p38alpha MAPK, CK1delta, and CK1epsilon) from Invitrogen.

TABLE 2

| Compound | Structure | Concentration (μM) | p38α MAPK IC$_{50}$ ± SEM (nM) | CK1δ IC$_{50}$ ± SEM (nM) | CK1ε IC$_{50}$ ± SEM (nM) |
|---|---|---|---|---|---|
| SB203580 | 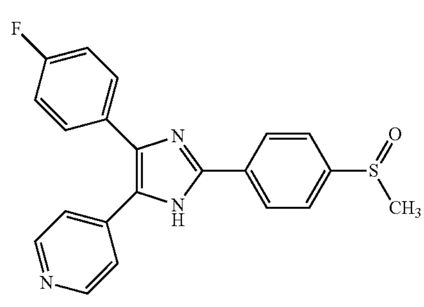 [SMILES: CS(=O)c1ccc(-c2nc(-c3ccc(F)cc3)c(-c3ccncc3)[nH]2)cc1] | 1-10 | 24 ± 4 | 43 ± 2 | 63 ± 5 |

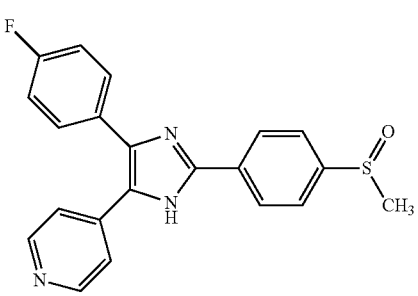

TABLE 2-continued
| Compound | Structure | Concentration (μM) | p38α MAPK IC$_{50}$ ± SEM (nM) | CK1δ IC$_{50}$ ± SEM (nM) | CK1ε IC$_{50}$ ± SEM (nM) |
|---|---|---|---|---|---|
| SB202190 | 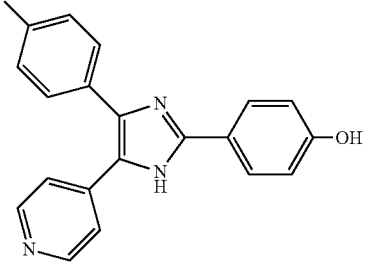 | 5 | 24 ± 8 | 53 ± 7 | 83 ± 4 |
| 1a (IM-31) | 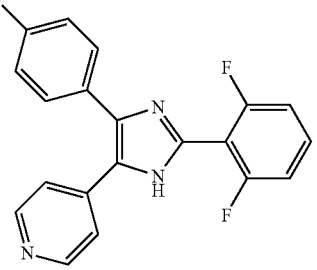 | 0.5-5 | 6.7 ± 1.5 | 6.8 ± 0.9 | 6.4 ± 0.4 |
| 1b (IM-30) | 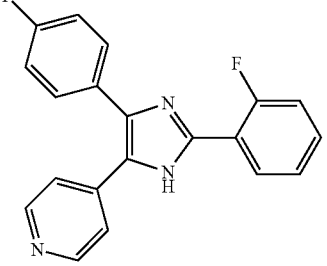 | 1-10 | 20 ± 4 | 32 ± 4 | 32 ± 4 |
| 1c (IM-29) | 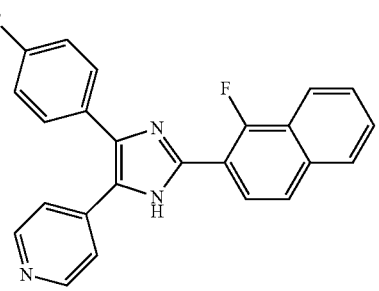 | 5 | 73 ± 17 | 15 ± 3 | 16 ± 3 |
| 2a (IM-26)* | 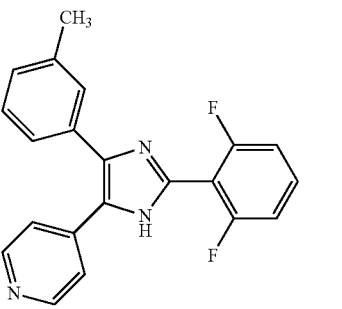 [SMILES: Cc1cccc(-c2nc(-c3c(F)cccc3F)[nH]c2-c2ccncc2)c1] | 1-10 | 4.3 ± 1.7 | 78 ± 20 | 44 ± 5 |

TABLE 2-continued

| Compound | Structure | Concentration (μM) | p38α MAPK IC$_{50}$ ± SEM (nM) | CK1δ IC$_{50}$ ± SEM (nM) | CK1ε IC$_{50}$ ± SEM (nM) |
| --- | --- | --- | --- | --- | --- |
| 2b (IM-19)* | 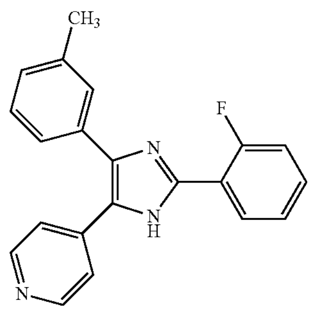 [SMILES: Cc1cccc(-c2nc(-c3ccccc3F)[nH]c2-c2ccncc2)c1] | 0.5-10 | 4.7 ± 1.2 | 454 ± 28 | 150 ± 89 |
| 2c (IM-27)* | 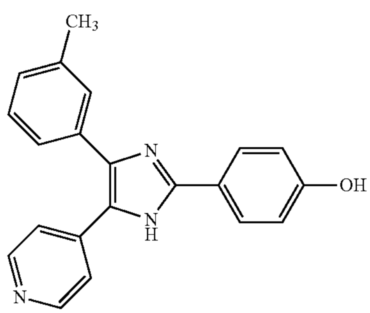 | 1-10 | 8.4 ± 3.0 | 1285 ± 828 | 411 ± 120 |
| 2d (IM-04)* | 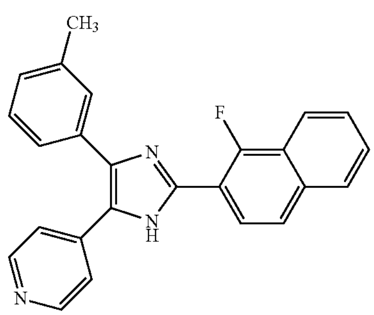 [SMILES: Cc1cccc(-c2nc(-c3ccc4ccccc4c3F)[nH]c2-c2ccncc2)c1] | 5 | 20 ± 7 | 490 ± 66 | 277 ± 40 |
| 2e (IM-28)* | 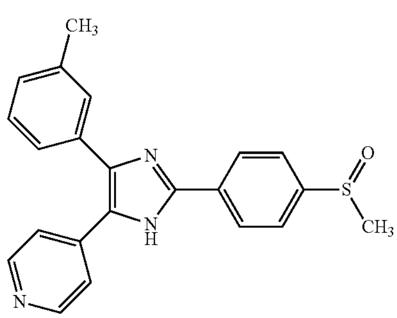 [SMILES: Cc1cccc(-c2nc(-c3ccc(S(C)=O)cc3)[nH]c2-c2ccncc2)c1] | 1-10 | 24 ± 9 | 708 ± 43 | 274 ± 7 |

TABLE 2-continued
| Compound | Structure | Concentration (μM) | p38α MAPK IC$_{50}$ ± SEM (nM) | CK1δ IC$_{50}$ ± SEM (nM) | CK1ε IC$_{50}$ ± SEM (nM) |
| --- | --- | --- | --- | --- | --- |
| 2f (IM-01) | 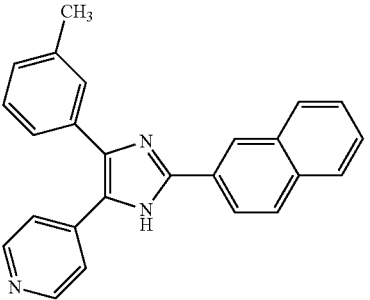 [SMILES: Cc1cccc(-c2nc(-c3ccc4ccccc4c3)[nH]c2-c2ccncc2)c1] | 5 | 98 ± 11 | 5% inhibition at 1 μM | 6% inhibition at 1 μM |
| 2g (IM-33) | 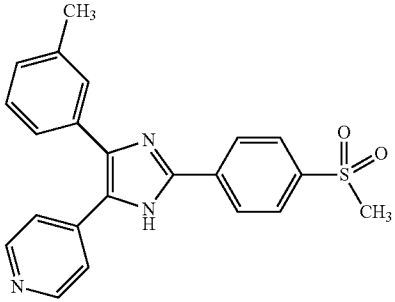 [SMILES: Cc1cccc(-c2nc(-c3ccc(S(C)(=O)=O)cc3)[nH]c2-c2ccncc2)c1] | 5 | 9.5 ± 2.8 | 23% inhibition at 1 μM | 36% inhibition at 1 μM |
| 2h (IM-35) | 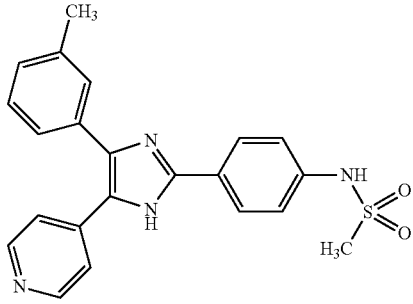 [SMILES: Cc1cccc(-c2nc(-c3ccc(NS(C)(=O)=O)cc3)[nH]c2-c2ccncc2)c1] | 5 | 5.0 | 13% inhibition at 1 μM | 40% inhibition at 1 μM |
| 2i (IM-36) | 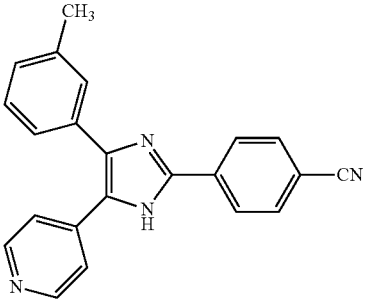 [SMILES: Cc1cccc(-c2nc(-c3ccc(C#N)cc3)[nH]c2-c2ccncc2)c1] | 5 | 5.3 ± 0.5 | 11% inhibition at 1 μM | 36% inhibition at 1 μM |

TABLE 2-continued

| Compound | Structure | Concentration (μM) | p38α MAPK IC$_{50}$ ± SEM (nM) | CK1δ IC$_{50}$ ± SEM (nM) | CK1ε IC$_{50}$ ± SEM (nM) |
| --- | --- | --- | --- | --- | --- |
| 2j (IM-37) | 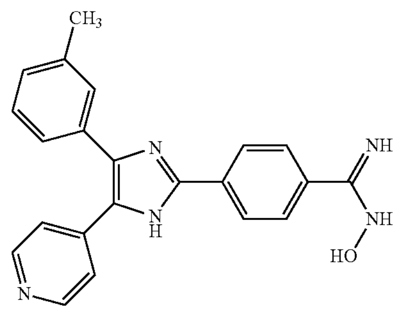 [SMILES: Cc1cccc(-c2nc(-c3ccc(C(=N)NO)cc3)[nH]c2-c2ccncc2)c1] | 5 | 3.2 ± 0.3 | 889 ± 290 | 295 ± 48 |
| 2k (IM-38) | 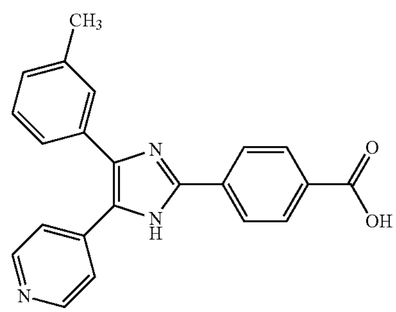 [SMILES: Cc1cccc(-c2nc(-c3ccc(C(=O)O)cc3)[nH]c2-c2ccncc2)c1] | 5 | 3.3 ± 1.1 | 4713 ± 1625 | 1061 ± 108 |
| 2l (IM-39) | 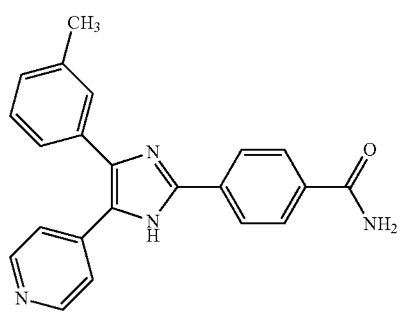 [SMILES: Cc1cccc(-c2nc(-c3ccc(C(N)=O)cc3)[nH]c2-c2ccncc2)c1] | 5 | 2.7 ± 0.3 | 787 ± 98 | 300 ± 16 |
| 2m (IM-40) | 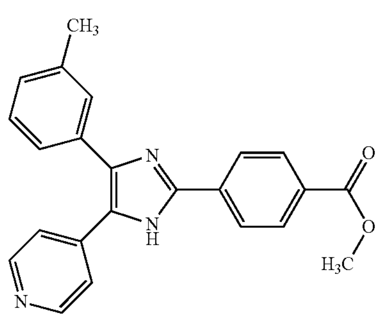 [SMILES: COC(=O)c1ccc(-c2nc(-c3cccc(C)c3)c(-c3ccncc3)[nH]2)cc1] | 5 | 3.7 ± 0.7 | 10% inhibition at 1 μM | 43% inhibition at 1 μM |

TABLE 2-continued
| Compound | Structure | Concentration (μM) | p38α MAPK IC$_{50}$ ± SEM (nM) | CK1δ IC$_{50}$ ± SEM (nM) | CK1ε IC$_{50}$ ± SEM (nM) |
|---|---|---|---|---|---|
| 2n (IM-32) | 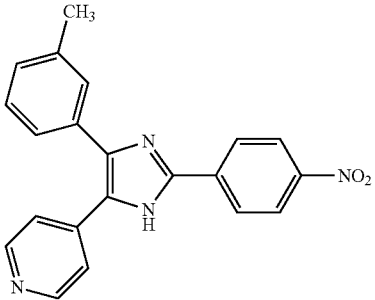 | 5 | 4.4 ± 2.4 | 31% inhibition at 1 μM | 47% inhibition at 1 μM |
| 2o (IM-34) | 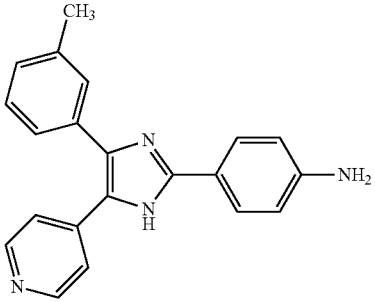 [SMILES: Cc1cccc(-c2nc(-c3ccc([N+](=O)[O-])cc3)[nH]c2-c2ccncc2)c1] | 5 | 2.8 ± 2.0 | 24% inhibition at 1 μM | 28% inhibition at 1 μM |
| 2p (IM-44) | 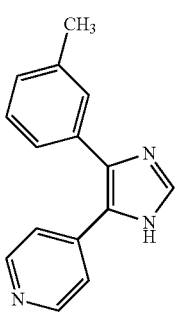 [SMILES: Cc1cccc(-c2nc[nH]c2-c2ccncc2)c1] | 5 | 45 ± 8 | 4% inhibition at 1 μM | 42% inhibition at 1 μM |
| 2q (IM-42) | 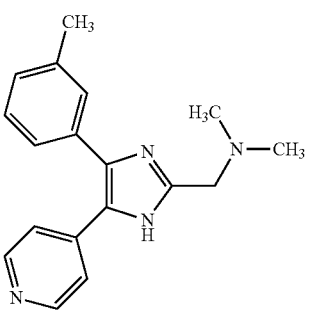 [SMILES: Cc1cccc(-c2nc(CN(C)C)[nH]c2-c2ccncc2)c1] | 5 | 26 ± 3 | 3% inhibition at 1 μM | 29% inhibition at 1 μM |

TABLE 2-continued

| Compound | Structure | Concentration (µM) | p38α MAPK IC$_{50}$ ± SEM (nM) | CK1δ IC$_{50}$ ± SEM (nM) | CK1ε IC$_{50}$ ± SEM (nM) |
| --- | --- | --- | --- | --- | --- |
| 2r (IM-41) | 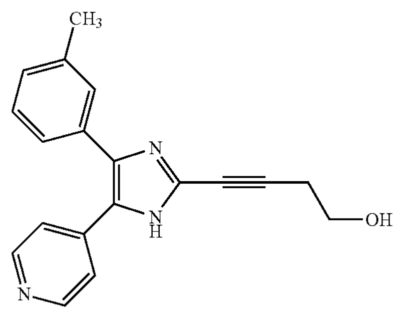 [SMILES: Cc1cccc(-c2nc(C#CCCO)[nH]c2-c2ccncc2)c1] | 5 | 47 ± 5 | 11% inhibition at 1 µM | 38% inhibition at 1 µM |
| 2s (IM-43) | 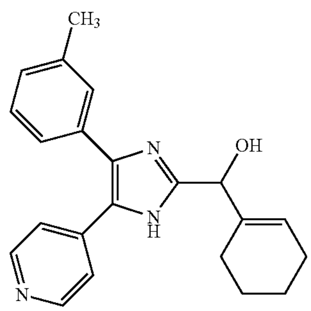 [SMILES: Cc1cccc(-c2nc(C(O)C3=CCCCC3)[nH]c2-c2ccncc2)c1] | 5 | 11 ± 2 | No inhibition at 1 µM | 22% inhibition at 1 µM |
| 2t (IM-02) | 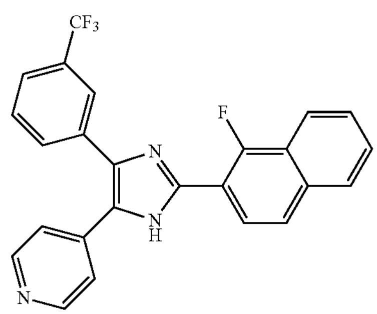 [SMILES: Fc1c(-c2nc(-c3cccc(C(F)(F)F)c3)c(-c3ccncc3)[nH]2)ccc2ccccc12] | 5 | 2655 ± 466 | No inhibition at 1 µM | No inhibition at 1 µM |
| 3a (IM-25)* | 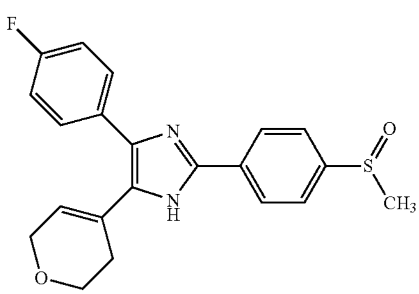 [SMILES: CS(=O)c1ccc(-c2nc(-c3ccc(F)cc3)c(C3=CCOCC3)[nH]2)cc1] | 1-20 | 454 ± 67 | 1494 ± 285 | 5891 ± 180 |
| 3b (IM-23) | 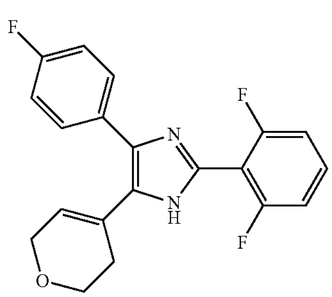 [SMILES: Fc1ccc(-c2nc(-c3c(F)cccc3F)[nH]c2C2=CCOCC2)cc1] | 5 | 55 ± 14 | 548 ± 116 | 751 ± 168 |

TABLE 2-continued

| Compound | Structure | Concentration (µM) | p38α MAPK IC$_{50}$ ± SEM (nM) | CK1δ IC$_{50}$ ± SEM (nM) | CK1ε IC$_{50}$ ± SEM (nM) |
| --- | --- | --- | --- | --- | --- |
| 3c (IM-24) | 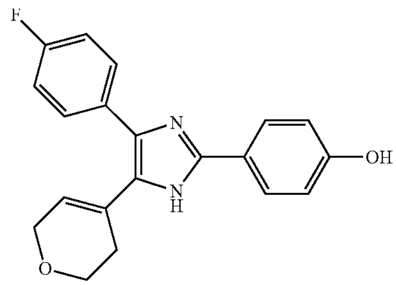 [SMILES: Oc1ccc(-c2nc(-c3ccc(F)cc3)c(C3=CCOCC3)[nH]2)cc1] | 5 | 149 ± 33 | 14% inhibition at 1 µM | No inhibition at 1 µM |
| 3d (IM-20) | 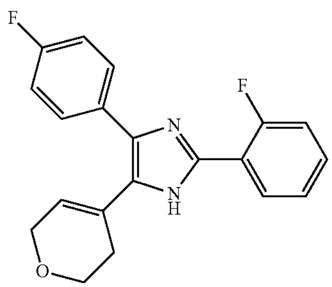 [SMILES: Fc1ccc(-c2nc(-c3ccccc3F)[nH]c2C2=CCOCC2)cc1] | 5 | 561 ± 141 | 1523 ± 825 | 1145 ± 287 |
| 3e (IM-22) | 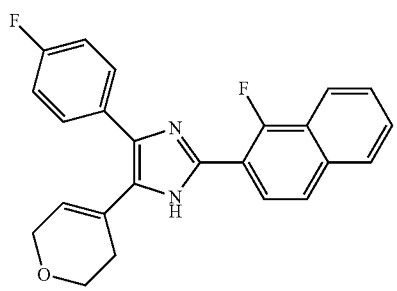 [SMILES: Fc1ccc(-c2nc(-c3ccc4ccccc4c3F)[nH]c2C2=CCOCC2)cc1] | 5 | 2314 ± 714 | 14% inhibition at 1 µM | No inhibition at 1 µM |
| 3f (IM-21) | 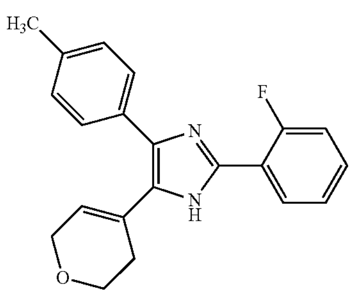 [SMILES: Cc1ccc(-c2nc(-c3ccccc3F)[nH]c2C2=CCOCC2)cc1] | 5 | 3372 ± 824 | No inhibition at 1 µM | No inhibition at 1 µM |
| 4a (IM-16)* | 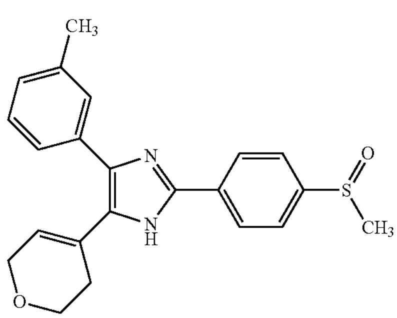 [SMILES: Cc1cccc(-c2nc(-c3ccc(S(C)=O)cc3)[nH]c2C2=CCOCC2)c1] | 1-10 | 73 ± 21 | 2539 | 5610 ± 319 |

TABLE 2-continued

| Compound | Structure | Concentration (μM) | p38α MAPK IC$_{50}$ ± SEM (nM) | CK1δ IC$_{50}$ ± SEM (nM) | CK1ε IC$_{50}$ ± SEM (nM) |
|---|---|---|---|---|---|
| 4b (IM-18) | 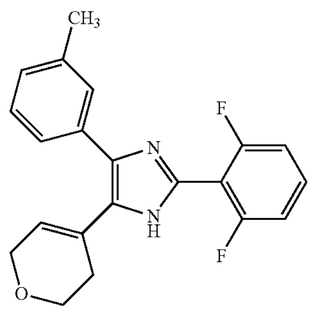 [SMILES: Cc1cccc(-c2nc(-c3c(F)cccc3F)[nH]c2C2=CCOCC2)c1] | 5 | 14 ± 2 | 3% inhibition at 1 μM | 1235 ± 437 |
| 4c (IM-13) | 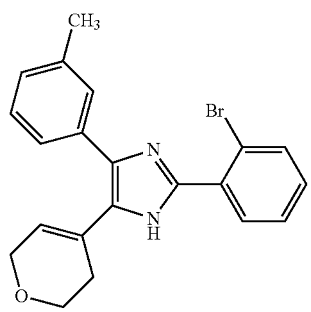 [SMILES: Cc1cccc(-c2nc(-c3ccccc3Br)[nH]c2C2=CCOCC2)c1] | 5 | 19 ± 2 | 23% inhibition at 1 μM | 23% inhibition at 1 μM |
| 4d (IM-17) | 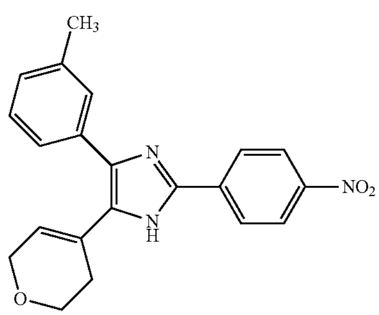 [SMILES: Cc1cccc(-c2nc(-c3ccc([N+](=O)[O-])cc3)[nH]c2C2=CCOCC2)c1] | 5 | 20 ± 2 | 17% inhibition at 1 μM | No inhibition at 1 μM |
| 4e (IM-15) | 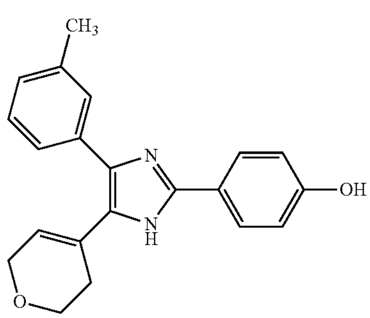 [SMILES: Cc1cccc(-c2nc(-c3ccc(O)cc3)[nH]c2C2=CCOCC2)c1] | 5 | 33 ± 2 | No inhibition at 1 μM | No inhibition at 1 μM |

TABLE 2-continued

| Compound | Structure | Concentration (μM) | p38α MAPK IC$_{50}$ ± SEM (nM) | CK1δ IC$_{50}$ ± SEM (nM) | CK1ε IC$_{50}$ ± SEM (nM) |
| --- | --- | --- | --- | --- | --- |
| 4f (IM-12) | 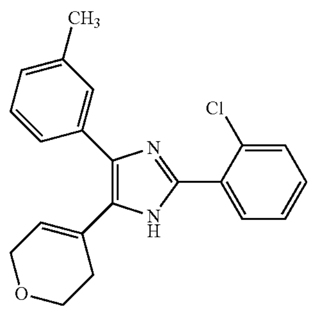 [SMILES: Cc1cccc(-c2nc(-c3ccccc3Cl)[nH]c2C2=CCOCC2)c1] | 5 | 43 ± 2 | 23% inhibition at 1 μM | 10% inhibition at 1 μM |
| 4g (IM-06) | 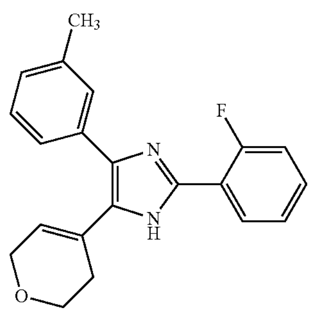 [SMILES: Cc1cccc(-c2nc(-c3ccccc3F)[nH]c2C2=CCOCC2)c1] | 5 | 90 ± 20 | 3% inhibition at 1 μM | No inhibition at 1 μM |
| 4h (IM-03) | 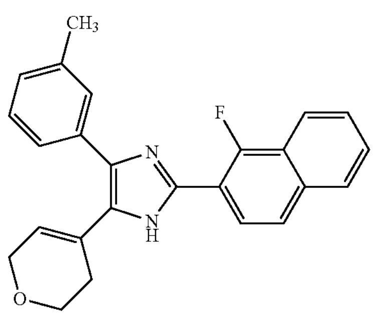 [SMILES: Cc1cccc(-c2nc(-c3ccc4ccccc4c3F)[nH]c2C2=CCOCC2)c1] | 5 | 262 ± 73 | No inhibition at 1 μM | No inhibition at 1 μM |
| 4i (IM-11) | 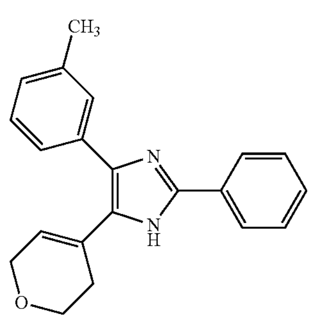 [SMILES: Cc1cccc(-c2nc(-c3ccccc3)[nH]c2C2=CCOCC2)c1] | 5 | 526 ± 137 | No inhibition at 1 μM | No inhibition at 1 μM |

TABLE 2-continued

| Compound | Structure | Concentration (μM) | p38α MAPK IC$_{50}$ ± SEM (nM) | CK1δ IC$_{50}$ ± SEM (nM) | CK1ε IC$_{50}$ ± SEM (nM) |
| --- | --- | --- | --- | --- | --- |
| 4j (IM-09) | 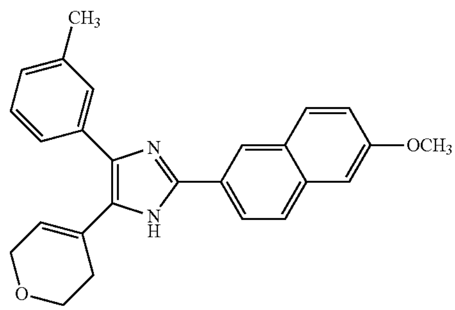 [SMILES: COc1ccc2cc(-c3nc(-c4cccc(C)c4)c(C4=CCOCC4)[nH]3)ccc2c1] | 5 | 2346 ± 374 | 13% inhibition at 1 μM | No inhibition at 1 μM |
| 4k (IM-14) | 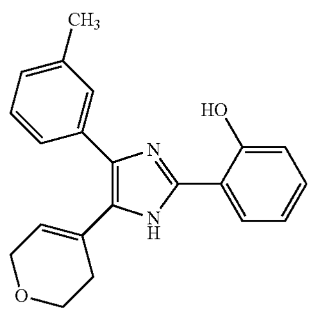 [SMILES: Cc1cccc(-c2nc(-c3ccccc3O)[nH]c2C2=CCOCC2)c1] | 5 | >5 μM | No inhibition at 1 μM | 3% inhibition at 1 μM |
| 5a (OZ-06)* | 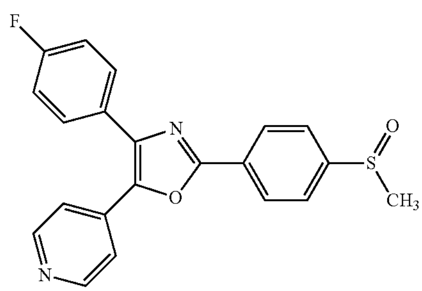 [SMILES: CS(=O)c1ccc(-c2nc(-c3ccc(F)cc3)c(-c3ccncc3)o2)cc1] | 5 | 314 ± 44 | 46% inhibition at 1 μM | 54% inhibition at 1 μM |
| 5b (OZ-12) | 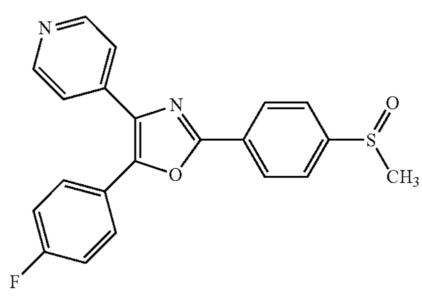 [SMILES: CS(=O)c1ccc(-c2nc(-c3ccncc3)c(-c3ccc(F)cc3)o2)cc1] | 5 | >5 μM | 34% inhibition at 1 μM | 51% inhibition at 1 μM |

Example 4: Differentiation of Cardiomyocytes with 2,4,5-Tri-Substituted Azole Compounds Initial studies with the 2,4,5-tri-substituted azole compounds were done at a fixed concentration of 5 μM. The 44 small molecules in table 2 were applied to hESC3 Nkx2.5e$^{GFP/w}$ cells after EB formation until day 8 of differentiation. On day 16 of differentiation, EBs were dissociated and analyzed with flow cytometry for green florescence protein (GFP) expression as a marker for cardiomyocyte differentiation. The results obtained are presented as GFP fold over DMSO control in FIG. 6a, where 1 represents an effect similar to DMSO. Only compounds for which the GFP expression fold over DMSO exceeded 2 are significantly cardiogenic. The initial screen identified one novel compound (IM-30) with similar cardiogenic properties as SB203580 and SB202190, which are established compounds for cardiomyocyte differentiation. Interestingly, a highly similar compound, IM-31 showed complete inhibition of cardiomyocyte development. The reliability of GFP expression as a cardiomyocyte marker was confirmed by co-staining with cardiomyocyte antibodies such as troponin T (FIG. 6b). The robustness of the differentiation protocol was demonstrated with an additional human embryonic stem cell line hESC7 (FIG. 6c) and human induced pluripotent stem cells (hiPSC) (FIG. 6d). Cyto-immunofluorescence staining of day 16 EBs derived from hiPSC, and grown on attachment plates showed characteristic cardio markers of typical cytoskeletal cardiac actin sarcomeres such as troponin T (cTnT), myosin light chain 2a (MLC2a) and sarcomeric actinin (SA). The mesoderm origin was confirmed with nuclear marker MEF2C (FIG. 6e).

Cardiomyocyte differentiation was also repeated with a selection of small molecules at a concentration range of 0.5-20 µM (FIG. 6f). The results showed that IM-31 can induce cardiomyocyte differentiation, when applied at a lower dose. Moreover, we showed that 1 µM of IM-31 has the same cardiogenic effect as 5 µM of SB203580 (FIG. 6g). IM-31 can be applied at a 5-times lower concentration than other comparable SB203580 analogues to induce cardiomyocyte differentiation. Therefore IM-31 is the most potent compound according to the invention.

Furthermore, a time course study of the differentiation process showed that the tested compounds can be applied either between days 1-8 or even more effectively between days 4-8 (FIG. 6h). The example included 2,4,5-tri-substituted imidazoles (SB203580, D4476, IM-. . . ) and thiazole (TAK715). The time course study revealed several false negative compounds such as IM-31, TAK715, and D4476 as they failed to induced cardiomyogenesis when applied at a concentration of 5 µM between days 1-8 but were found to be good inducers when applied at the same concentration between days 4-8. A set time frame between days 4-8 allows a wider range of compounds to be tested without changing the concentration of the compounds. This is a great advantage, which will reduce the number of experiments to one concentration and one time course in order to investigate the correlations between a compound's in vitro effect on target protein(s) and its cardiomyogenic activity. Moreover the effect of 2,4,5-tri-substituted azoles on cardiomyogenesis in the days 4-8 time course indicates that late (post mesoderm) development of cardiomyocytes can be influenced with the method according to the invention.

Example 5: Correlation of CK1 $IC_{50}$ Values with Cardiomyocyte Differentiation Small molecules were tested for their inhibitory activities towards casein kinase 1 delta (CK1δ) and 1 epsilon (CK1ε). The in vitro LanthaScreen Eu kinase binding assay was used to determine the $IC_{50}$ values for 15 of the synthesized compounds and 5 commercial inhibitors including SB203580 (Table 3). Tested compounds displayed a wide range of affinity between 6.8 nM (high affinity=strong inhibition) to values over 1000 nM (low affinity=very weak inhibition). Further the list includes 2,4,5-tri-substituted azole of three classes, thiazole (TAK-715), oxazoles (OZ-06, OZ-12) and imidazoles (all other compounds). These selected compounds were used to differentiate hESC3 at fix doses of 5 µM and they were applied during the differentiation process between days 4-8. All three classes of 2,4,5-tri-substituted azole are able to induce cardiac differentiation (FIG. 7a). The Nkx2.5 GFP expression on day 11 was measured with flow cytometry and compared to the DMSO control. Values are expressed as fold over DMSO control (FIG. 7a). Results from FIG. 7a (CK1ε/δ $IC_{50}$ values) and FIG. 7b (GFP expression fold over DMSO) were plotted against each other in FIG. 7b. A strong correlation between the CK1δ/ε affinity and the differentiation results are shown with a log curve fit. We show here that CK1 inhibition correlates with cardiomyocyte differentiation.

Table 3 shows the differentiation of hESC3 into cardiomyocytes with 20 small molecules for which the CK1 IC50 values were determined using a LanthaScreen Eu kinase binding assay.

TABLE 3

| Compound | $IC_{50}$ (nM) | |
|---|---|---|
| | CK1δ | Ck1ε |
| SB203580 | 43 | 63 |
| SB202190 | 53 | 83 |
| IM-4 | 490 | 277 |
| IM-16 | 2539 | 5610 |
| IM-19 | 454 | 150 |
| IM-20 | 1523 | 1145 |
| IM-23 | 548 | 751 |
| IM-25 | 1494 | 5891 |
| IM-26 | 78 | 44 |
| IM-27 | 1285 | 411 |
| IM-28 | 708 | 274 |
| IM-29 | 15 | 16 |
| IM-30 | 32 | 32 |
| IM-31 | 6.8 | 6.4 |
| IM-37 | 889 | 295 |
| IM-38 | 4713 | 1061 |
| IM-39 | 787 | 300 |
| OZ-06 | | |
| OZ-12 | | |
| TAK-715 | 78 | 107 |
| D4476 | 157 | 88 |
| SB431542 | 174 | 147 |

Example 6: High Yield Production of Cardiomyocytes

To investigate if the yield of cardiomyocytes could be further improved, H3 hESCs Nkx2.5$^{eGFP/w}$ were seeded at 2.5×10$^6$ cells/12-ULA well and treated with 3 µM CHIR99021 for 24 h. Thereafter the medium was changed and small molecules SB203580, IM-30 and IM-31 were added on two separate time courses, one from days 1-8 days and the other from days 4-8 at a concentration of 5 µM. A known Wnt inhibitor, IWP-2, was also added on a time course from days 4-8 at the same concentration. The generated cardiomyocytes on day 11 were analyzed with flow cytometry and showed an average of 30% Nkx2.5 population for CHIR99021 only treatment and a 50% Nkx2.5 population when combined with small molecules (FIG. 8a, left). The total cell count showed that the combination of CHIR99021 and IM-31 (applied at the late time course of days 4-8) has the greatest effect on cell expansion (2 fold increase, FIG. 8a, center). The yield of cardiomyocytes shown in FIG. 8a, right was calculated based on the following equation.

$$\text{yield} = \frac{\text{cell number day 11} * \text{cardiomyocyte } (GFP) \text{ precentage day 11}}{\text{initial seeding number}} \quad \text{[Equation 1]}$$

The results showed that the use of CHIR99021 and IM-31 (4-8 days) gave the best cardiomyocyte yield on day 11 where almost 1.2 cardiomyocytes per hESC seeded was obtained (FIG. 8a, right). The combination of IM-31 with CHIR99021 showed a twofold increase in cardiomyocyte yield when compared to other Wnt inhibitor compounds such as IWP-2. IWP-2 showed comparable Nkx2.5 expressions, but a strongly reduced cell growth (FIGS. 8a, center and 8a, right). IM-31 is not only a cardiac inducer, but it promotes cell growth at the same time.

The differentiated embryoid bodies were also visually analysed to determine cardiomyocyte functionality using parameters such as beat count (percentage of EBs which display contracting movements within 10 s time frame), beating area (mm$^2$), and beat frequency (s$^{-1}$ measured EB contraction within 10 s time frame, FIG. 8b). The functionality analyses shows similar results for CHIR99021 only treatment and CHIR99021 with SB203580 (days 1-8) or IM-31 (days 4-8) treatments. Under these treatments, beating counts were over 75% with >5 mm$^2$ beating area and showed an average beating frequency of 25-30 beats per minute (0.5s$^{-1}$). However, the combination of CHIR99021 and IWP-2 displayed reduced functionality compared to the rest. IM-31 (days 1-8) showed inhibition of cardiomyocytes development which is in line with earlier observations that IM-31 applied at 5 μM between days 1-8 inhibit cardiomyogenesis. The results verify a high functionality of the generated cardiomyocytes.

Example 7: Alternative High Yield Production of Cardiomyocytes

Studies with the 2,4,5-tri-substituted azole compounds were done at a fixed concentration of 5 μM at an induction day 2 and alternatively at day 3. The small molecules in Table 4 (Structures and CK1δ kinase affinities of the molecules also shown) were applied to hESC3 Nkx2.5$^{eGFP/w}$ cells after 24 h EB formation with 6 μM CHIR99021 until day 6 of differentiation. On day 14 of differentiation, EBs were visually analysed for cardiomyocyte differentiation. The green fluorescence protein (GFP) expression area (μm$^2$) was measured against the total embryoid body size (μm$^2$). The ratio of these measurements indicates the percentage of generated cardiomyocytes (Table 5). The initial screen identified novel compounds (TA-01, ZQX-19 and TA-02, ZQX-20) with higher cardiogenic properties as SB203580 and IWP-2, which are established compounds for cardiomyocyte differentiation at specific time course (FIG. 9). The robustness of the differentiation protocol cardiac marker expression and cell growth was demonstrated with an additional human embryonic stem cell line H7 and 2 human induced pluripotent stem cells (IMR-90, Donor11) (FIG. 10). Technology transfer of IM-31 (TA-01) from embryoid body differentiation to microcarrier platform differentiation is feasible and can produce same amounts of cardiomyocytes (cell numbers) when compared to IWP-2, which is an established compound for cardiomyocyte differentiation (FIGS. 11a, b and c).

TABLE 4

| Name | Structure | MW | CK1δ |
|---|---|---|---|
| Zqx-32 | 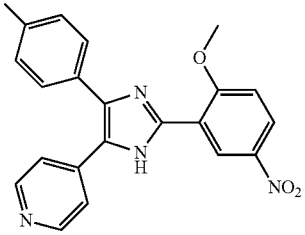 | 390.1128 | 51.90 |
| Zqx-31 | 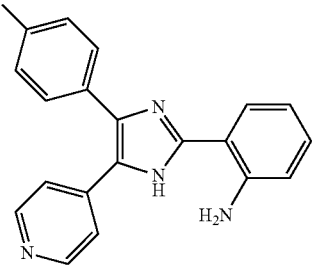 | 330.1281 | 1753 |
| Zqx-30 | 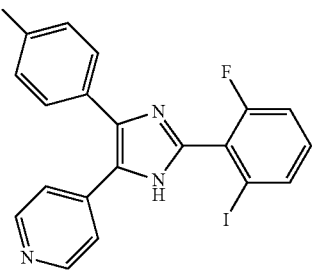 | 459.0044 | 25.64 |
| Zqx-29 | 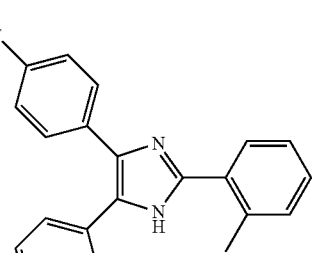 | 329.1328 | 46.06 |
| Zqx-28 | 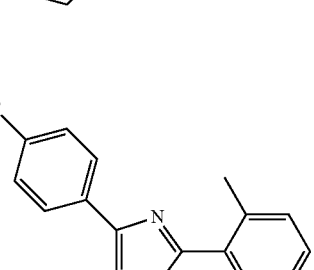 | 343.1485 | 25.58 |
| Zqx-27 | 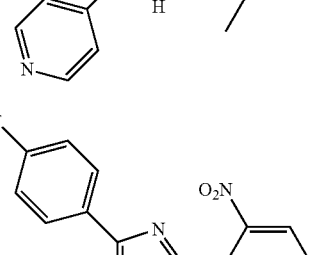 | 360.1203 | 14.19 |

TABLE 4-continued

| Name | Structure | MW | CK1δ |
|---|---|---|---|
| Zqx-26 | 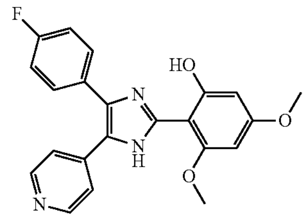 [SMILES: COc1cc(O)c(-c2nc(-c3ccc(F)cc3)c(-c3ccncc3)[nH]2)c(OC)c1] | 391.4024 | 4932 |
| Zqx-25 | 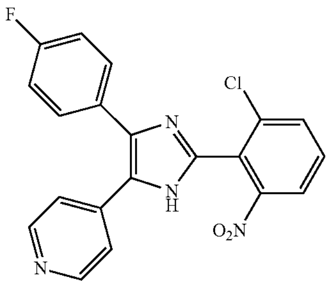 [SMILES: O=[N+]([O-])c1cccc(Cl)c1-c1nc(-c2ccc(F)cc2)c(-c2ccncc2)[nH]1] | 394.7904 | 74.39 |
| Zqx-23 | 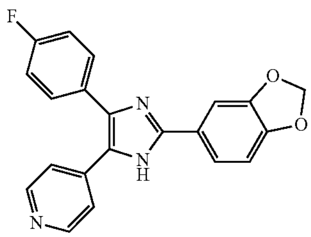 [SMILES: Fc1ccc(-c2nc(-c3ccc4c(c3)OCO4)[nH]c2-c2ccncc2)cc1] | 359.3604 | 554.6 |
| Zqx-22 | 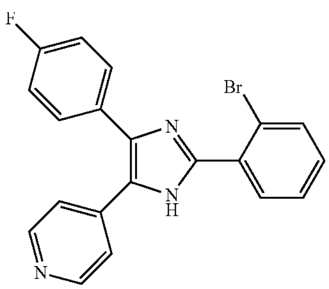 [SMILES: Fc1ccc(-c2nc(-c3ccccc3Br)[nH]c2-c2ccncc2)cc1] | 394.2474 | 10.83 |
| Zqx-21 | 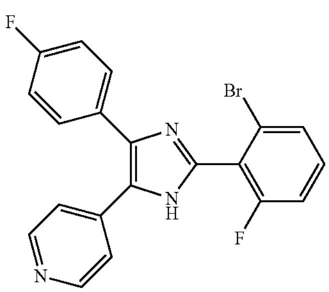 [SMILES: Fc1ccc(-c2nc(-c3c(F)cccc3Br)[nH]c2-c2ccncc2)cc1] | 412.2378 | 9.995 |
| Zqx-20 | 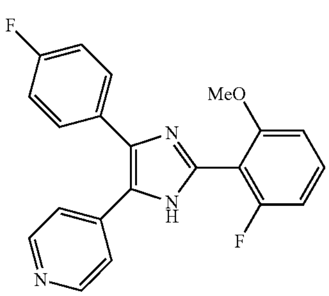 [SMILES: COc1cccc(F)c1-c1nc(-c2ccc(F)cc2)c(-c2ccncc2)[nH]1] | 363.3678 | 26.53 |
| Zqx-19 | | 367.7838 | 17.84 |
| Zqx-18 | | 375.4034 | 448.2 |
| Zqx-17 | | 349.7934 | 49.74 |
| Zqx-16 | | 345.3774 | 120.5 |
| Zqx-15 | | 384.2354 | 31.48 |

TABLE 4-continued

| Name | Structure | MW | CK1δ |
|---|---|---|---|
| Zqx-14 | (structure) | 315.3514 | 192.8 |

TABLE 5

| | Average GFP % | STD GFP % | Average GFP μm² | STD GFP μm² | Average Area μm² | STD Area μm² |
|---|---|---|---|---|---|---|
| Induction Day 2 | | | | | | |
| ZQX-14 | 42.4% | 8.3% | 335.6 | 29.3 | 810.7 | 227.9 |
| ZQX-15 | 0.0% | 0.0% | 0.0 | 0.0 | 129.4 | 18.6 |
| ZQX-16 | 32.8% | 4.8% | 184.7 | 20.2 | 576.1 | 139.7 |
| SB203580 | 34.6% | 7.7% | 217.8 | 41.8 | 655.4 | 230.2 |
| Control (DMSO) | 18.2% | 10.6% | 154.5 | 101.8 | 795.5 | 126.8 |
| IWR-1 | 41.3% | 14.0% | 308.9 | 79.1 | 763.0 | 97.6 |
| IWP-2 | 4.8% | 4.1% | 19.6 | 18.6 | 362.9 | 121.6 |
| TA-01 | 1.5% | 2.9% | 19.1 | 38.2 | 814.7 | 423.6 |
| TA-02 | 32.8% | 10.2% | 250.1 | 38.6 | 816.0 | 251.1 |
| ZQX-17 | 30.4% | 9.2% | 183.0 | 73.8 | 586.7 | 114.5 |
| ZQX-18 | 27.5% | 18.7% | 207.3 | 140.1 | 579.4 | 352.8 |
| ZQX-19 | 2.4% | 4.8% | 46.4 | 92.7 | 903.3 | 733.4 |
| ZQX-27 | 15.1% | 13.5% | 258.6 | 104.5 | 1469.4 | 672.9 |
| ZQX-28 | 0.0% | 0.0% | 0.0 | 0.0 | 302.4 | 230.5 |
| ZQX-29 | 28.6% | 14.4% | 277.1 | 120.3 | 876.4 | 829.7 |
| ZQX-30 | 4.6% | 5.3% | 60.9 | 72.2 | 1361.8 | 335.4 |
| ZQX-31 | 28.9% | 6.6% | 258.3 | 69.4 | 891.2 | 116.3 |
| ZQX-32 | 32.8% | 8.6% | 157.6 | 41.7 | 483.6 | 58.9 |
| ZQX-20 | 26.0% | 6.5% | 286.8 | 55.5 | 1145.3 | 348.1 |
| ZQX-21 | 0.0% | 0.0% | 0.0 | 0.0 | 1383.8 | 109.6 |
| ZQX-22 | 26.2% | 7.6% | 166.5 | 72.8 | 623.0 | 213.4 |
| ZQX-25 | 0.0% | 0.0% | 0.0 | 0.0 | 544.3 | 51.2 |
| ZQX-26 | 30.9% | 5.4% | 233.9 | 75.9 | 757.8 | 198.8 |
| Induction Day 3 | | | | | | |
| ZQX-27 | 3.4% | 6.8% | 57.9 | 115.7 | 1758.3 | 263.5 |
| ZQX-28 | 2.1% | 4.1% | 6.1 | 12.1 | 271.7 | 30.9 |
| ZQX-29 | 2.7% | 5.4% | 39.9 | 79.7 | 1296.6 | 182.9 |
| ZQX-30 | 12.6% | 10.6% | 128.3 | 73.7 | 1142.4 | 334.3 |
| ZQX-31 | 5.1% | 6.2% | 96.0 | 64.4 | 1662.3 | 472.0 |
| ZQX-32 | 4.6% | 4.3% | 41.0 | 25.9 | 790.4 | 145.8 |
| ZQX-20 | 37.3% | 16.1% | 331.1 | 21.8 | 996.2 | 390.2 |
| ZQX-21 | 3.4% | 6.7% | 16.9 | 33.7 | 974.3 | 437.5 |
| ZQX-22 | 24.4% | 6.3% | 284.4 | 84.9 | 1165.0 | 252.5 |
| ZQX-25 | 15.6% | 10.1% | 163.6 | 105.0 | 1105.4 | 130.7 |
| ZQX-26 | 8.3% | 6.0% | 88.2 | 48.7 | 1152.7 | 261.9 |
| ZQX-14 | 5.9% | 6.1% | 91.6 | 94.9 | 1474.4 | 200.4 |
| ZQX-15 | 0.0% | 0.0% | 0.0 | 0.0 | 384.0 | 208.7 |
| ZQX-16 | 14.5% | 5.8% | 125.6 | 51.8 | 950.3 | 447.7 |
| SB203580 | 3.7% | 4.7% | 40.2 | 35.4 | 814.2 | 236.5 |
| Control (DMSO) | 8.9% | 6.7% | 95.5 | 68.8 | 1088.6 | 46.4 |
| IWR-1 | 51.1% | 3.2% | 426.3 | 46.6 | 831.4 | 77.6 |
| IWP-2 | 38.4% | 17.8% | 216.9 | 38.3 | 604.5 | 180.6 |
| TA-01 | 31.1% | 1.0% | 476.6 | 10.1 | 1529.1 | 82.8 |
| TA-02 | 36.5% | 6.9% | 354.1 | 135.5 | 968.7 | 307.6 |
| ZQX-17 | 24.6% | 12.3% | 232.7 | 134.4 | 971.6 | 535.9 |
| ZQX-18 | 15.4% | 15.5% | 143.4 | 138.4 | 1065.1 | 213.1 |
| ZQX-19 | 32.7% | 7.1% | 511.6 | 110.2 | 1616.9 | 446.8 |

BRIEF DESCRIPTION OF DRAWINGS

The accompanying drawings illustrate a disclosed embodiment and serves to explain the principles of the disclosed embodiment. It is to be understood, however, that the drawings are designed for purposes of illustration only, and not as a definition of the limits of the invention.

FIG. 1 shows the general structures of the 2,4,5-tri-substituted azole compounds synthesized.

FIG. 2 shows schematic synthesis route of imidazoles 1a-1c as well as imidazoles ZQX-14-23 and ZQX-25-32.

FIG. 3 shows schematic synthesis route of imidazoles 2f-2t.

FIG. 4 shows schematic synthesis route of imidazoles 3b-3f and 4b-4k.

FIG. 5 shows schematic synthesis route of oxazoles 5a and 5b.

FIG. 6a shows the hESCs differentiation with the 44 small molecules.

FIG. 6b shows the co-staining of green fluorescence protein expression and cardiac marker troponin T on hESC3.

FIG. 6c shows the differentiation of hESC7.

FIG. 6d shows the differentiation of human induced pluripotent stem cells.

FIG. 6e shows an IF staining of differentiated human induced pluripotent stem cells.

FIG. 6f shows hESC3 dose dependent differentiation with small molecules at different concentrations (μM).

FIG. 6(g) shows the Nkx2.5 expression of hESC3 treated with IM-31 (1 μM), IM-30 and SB203580 (5 μM).

FIG. 6(h) shows the hESC3 time course dependent differentiation with small molecules.

FIGS. 7a and b show a correlation between CK1 inhibition and cardiomyogenesis.

FIGS. 8a and b show a high efficiency in cardiomyocyte differentiation.

FIG. 9 in combination with Table 4 shows the time dependance of 2,4,5-tri-substituted azoles with CHIR99021 for cardiomyocyte differentiation.

FIG. 10 shows the stem cells robustness of high efficiency cardiomyocyte differentiation with 3 human induced pluripotent stem cells.

FIG. 11a shows the technical application of IM-31 (TA-01) on microcarrier platform technologies for large scale cardiac differentiation FIG. 11b shows the stem cell pluripotency on microcarrier platform technologies prior to differentiation FIG. 11c shows the cardiac differentiation efficiency of IM-31 (TA-01) on microcarrier platform technologies

DETAILED DESCRIPTION OF DRAWINGS

Referring to FIG. 6, a detailed showing of the pluripotent stem cell differentiation into cardiomyocytes with small molecules is made. The drawings are explained in more detail: (a) Differentiation of hESC3 into cardiomyocytes with 44 compounds at 5 μM applied between days 1-8 during differentiation. (b) Nkx2.5 green fluorescence protein (GFP) expression measured with flow cytometry and compared to DMSO control expressed as fold over DMSO. Representative flow cytometry analyses with GFP (green) and troponin T stain (red2) shows the absolute values of cardiac population. Process robustness was demonstrated with (c) hESC7 and (d) hiPSCs. (e) Cyto-immunofluorescence of differentiated cells shows structural segments of the cardiac sarcomeres with cTnT, MLC2a and sarcomeric actinin (SA), as well as nuclear mesoderm marker MEF2c on differentiated embryoid bodies. Nuclear stain is DAPI. (f) Titration of selected small molecules during the days 1-8 of the differentiation protocol shows concentration dependent GFP expression peaks, and identifies IM-31 as the strongest cardiomyocyte inducer. (g) Representative flow analyses of IM-31, IM-30 and SB203580 is shown in flow cytometer dot plot (h) Time course differentiation results with selected small compounds at 5 µM induction for 24 h, 0-3, 0-8 and 4-8 days illustrates late stage (post mesoderm) efficiency of small molecules. GFP was measured as fold over DMSO control in (a), (f), and (g).

Referring to FIG. 7, the drawings are explained in more detail: (a) compounds were dosed at 5 µM during days 4-8 of the differentiation process. Green fluorescence protein (GFP) expression was measured with flow cytometry and compared to DMSO control showed in fold increase over DMSO. (b) IC50 values for CK 1 delta and 1 epsilon from (Table 3) were plotted against the GFP expression fold (a), and a strong correlation was demonstrated.

Referring to FIG. 8a, the drawings are explained in more detail: (left) Differentiation of hESC3 into cardiomyocyte with 24 h incubation of 3 µM CHIR99021 followed by small molecules SB203580, IM-30, IM-31 and IWP-2 at 5 µM delivered during days 1-8 and days 4-8 during a 11 day differentiation process. Green fluorescence protein (GFP) expression measured with flow cytometry is displayed in percentage over the whole population. (center) The viable cell number was measured on day 11 after EB dissociation with Nucleocounter. (right) The cardiomyocyte yields obtained with the small molecules combination protocol. The values were calculated using the flow cytometry data (left) and the cell count (center).

Referring to FIG. 8b, the drawings are explained in more detail: A Nikon Eclipse Ti microscope with an automated Time Resolved Video Analysis for cardiomyocyte contraction was used to calculate EB beating and frequency. Images show EBs in 12 Well plates after 16 days of differentiation. The percentage of beating EBs as well as the beating area was calculated with the analytical software and displayed in the table below the pictures. The beating contraction and frequency ($s^{-1}$) was analyzed from a sample of 16 EBs. Three representative images of a 10 s time frame of contractile movement video analyses are shown in the lowest part of the figure.

Referring to FIG. 9, the drawing shows the GFP are measurements of EBs after 14 days of differentiation with 2,4,5-tri-substituted azoles induced either on day 2 or day 3. Compounds groups (dark=day 3 high cardiac inducers; less dark, small=day 2 high cardiac inducers; light colour=control and other commercial inhibitors for cardiac differentiation). The grey box means that there is no significant difference to control in this area of the graph.

Referring to FIG. 10, the top part of the drawing shows the expression of cardiac markers (cTnt, MLC2a) of differentiated human embryonic stem cells (H7) and induced pluripotent stem cells (IMR-90, Donor 11) with CHIR99021 and IM-31 (TA-01) on day 14; and the lower part shows the cell count of differentiated human embryonic stem cells (H7) and induced pluripotent stem cells (IMR-90, Donor 11) with CHIR99021 and IM-31 (TA-01) on day 14.

Referring to FIG. 11a of the drawing shows hPSC expanded on microcarriers and differentiated into beating cardiomyocytes aggregates (scale bar 500 µM); left: HES-3 freshly seeded on microcarriers (100 µm in diameter), center: hPSC expansion on microcarriers to embryoid bodies (500 µm), right: cardiac differentiation with TA-01 on microcarriers to beating aggregates (>1 mm). FIG. 11b shows pluripotency marker expression of hPSC on microcarriers during cell expansion, and FIG. 11c shows expression of cardiac markers (cTnt, MLC2a, MF20) of differentiated microcarrier-embryoid bodies with IM-31 (TA-01) and IWP-2 commercial wnt inhibitor for cardiac differentiation.

INDUSTRIAL APPLICABILITY

The method and novel compounds as defined above may find multiple number of applications in which new ways for efficient stem cell differentiation are desirable. For example, the methods as defined above may be used to provide cardiomyocytes in higher efficiency by using small molecules or combinations of small molecules at different differentiation stages. The invention, therefore, provides an improved method and new compounds to be used in such methods in order to generate cells that can be potentially used in regenerative medicine for treating heart diseases. It is of technological significance that higher cardiomyocyte yields can be achieved with small molecules according to the invention. Especially with the presented embryoid body based protocol in suspension culture the method of the invention may be scaled up for the production of cardiomyocytes with bioprocessing technologies to a magnitude of therapeutic significance.

It will be apparent that various other modifications and adaptations of the invention will be apparent to the person skilled in the art after reading the foregoing disclosure without departing from the spirit and scope of the invention and it is intended that all such modifications and adaptations come within the scope of the appended claims.

What is claimed is:

1. A compound selected from the following compounds, or a tautomer, or a salt thereof:

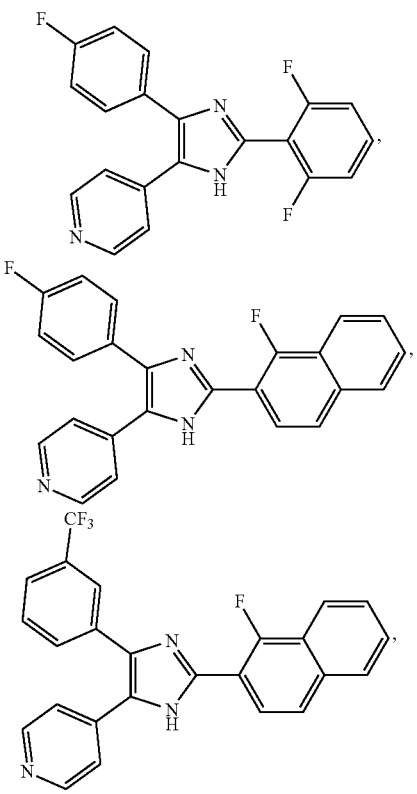

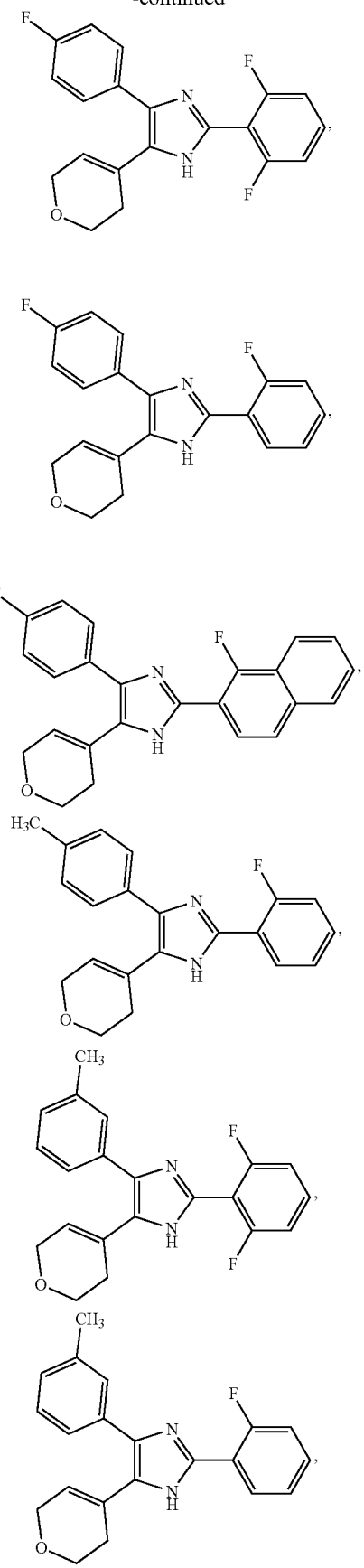
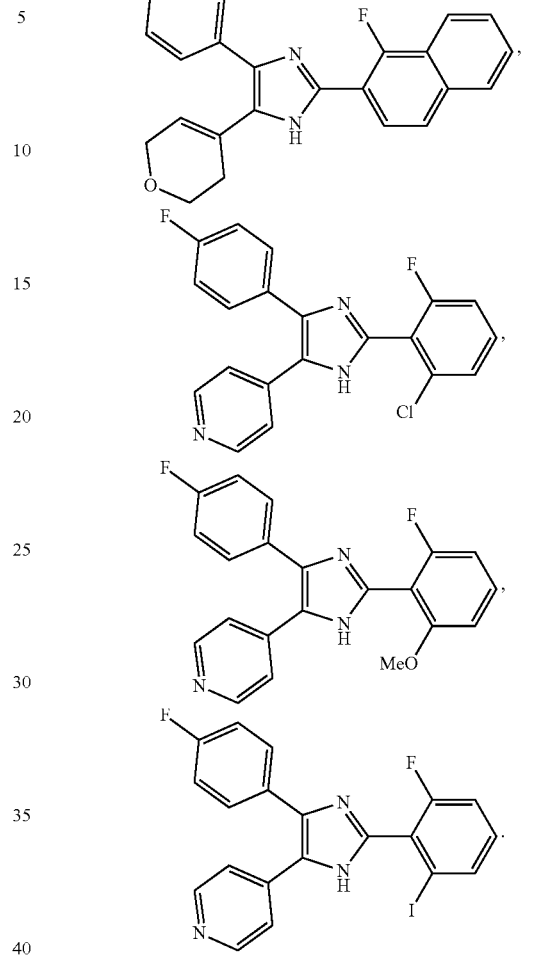
2. The compound according to claim 1, wherein the compound is:
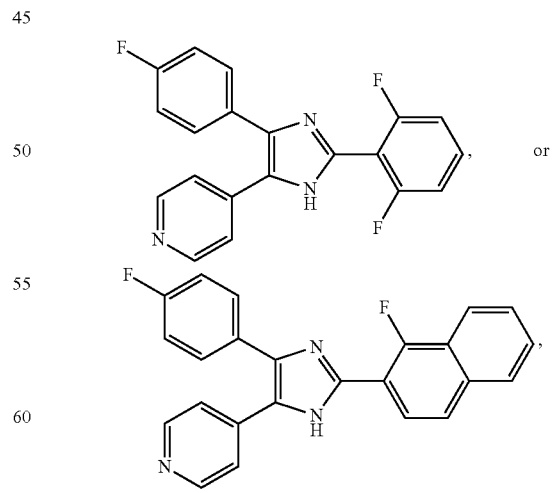
or a tautomer or a salt thereof.
3. A compound or a tautomer or a salt thereof, wherein the compound is:

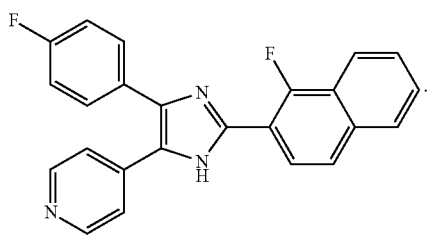 [SMILES: Fc1ccc(-c2nc(-c3ccc4ccccc4c3F)[nH]c2-c2ccncc2)cc1]
* * * * *